US012616672B2

(12) United States Patent
Dalli et al.

(10) Patent No.: US 12,616,672 B2
(45) Date of Patent: May 5, 2026

(54) METHODS FOR ASSESSING RISK OF CARDIOVASCULAR DISEASE AND METHODS AND COMPOUNDS FOR USE IN TREATING OR PREVENTING CARDIOVASCULAR DISEASE

(71) Applicant: Queen Mary University of London, London (GB)

(72) Inventors: Jesmond Dalli, London (GB); Romain Alexandre Colas, London (GB); Patricia Regina Souza, London (GB)

(73) Assignee: Queen Mary University of London, London (GB)

( * ) Notice: Subject to any disclaimer, the term of this patent is extended or adjusted under 35 U.S.C. 154(b) by 695 days.

(21) Appl. No.: 16/648,342

(22) PCT Filed: Sep. 19, 2018

(86) PCT No.: PCT/EP2018/075326

§ 371 (c)(1),
(2) Date: Mar. 18, 2020

(87) PCT Pub. No.: WO2019/057756

PCT Pub. Date: Mar. 28, 2019

(65) Prior Publication Data

US 2020/0215014 A1 Jul. 9, 2020

(30) Foreign Application Priority Data

Sep. 19, 2017 (GB) ..................................... 1715115
Feb. 1, 2018 (GB) ..................................... 1801694

(51) Int. Cl.

| | |
|---|---|
| ***A61K 31/202*** | (2006.01) |
| ***A61K 9/00*** | (2006.01) |
| ***A61P 9/00*** | (2006.01) |
| ***G01N 33/569*** | (2006.01) |
| ***G01N 33/92*** | (2006.01) |
| ***G16H 10/40*** | (2018.01) |
| ***G16H 20/10*** | (2018.01) |
| ***G16H 50/30*** | (2018.01) |

(52) U.S. Cl.
CPC .......... *A61K 31/202* (2013.01); *A61K 9/0053* (2013.01); *A61P 9/00* (2018.01); *G01N 33/56972* (2013.01); *G01N 33/92* (2013.01); *G16H 10/40* (2018.01); *G16H 20/10* (2018.01); *G16H 50/30* (2018.01); *G01N 2800/32* (2013.01); *G01N 2800/52* (2013.01)

(58) Field of Classification Search
CPC ....... A61K 31/202; A61K 9/0053; A61P 9/00; A61P 9/10; G01N 33/56972; G01N 2800/32
See application file for complete search history.

(56) References Cited

U.S. PATENT DOCUMENTS

2009/0318394 A1* 12/2009 Nauroth ................. A61K 31/22 514/549

FOREIGN PATENT DOCUMENTS

| | | |
|---|---|---|
| WO | 2002024194 | 3/2002 |
| WO | 2007127377 | 11/2007 |
| WO | 2009053523 | 4/2009 |
| WO | 2011116128 | 9/2011 |
| WO | 2014193652 | 12/2014 |
| WO | 2017015271 | 1/2017 |
| WO | 2018197650 | 11/2018 |

OTHER PUBLICATIONS

Endreyni, "Metrics for the Evaluation of Bioequivalence of Modified-Release Formulations", The AAPS Journal, vol. 14, No. 4, December, pp. 813-819. (Year: 2012).*

Abdulnour et al., "Aspirin-triggered resolvin D1 is produced during self-resolving gram-negative bacterial pneumonia and regulates host immune responses for the resolution of lung inflammation", Mucosal Immunol, 2016, 9(5), pp. 1278-1287.

Akagi et al., "Systemic delivery of proresolving lipid mediators resolvin D2 and maresin 1 attenuates intimal hyperplasia in mice", FASEB J, 2015, 29(6), pp. 2504-2513.

Akiba et al., "Involvement of lipoxygenase pathway in docosapentaenoic acid-induced inhibition of platelet aggregation", Biol Pharm Bull, 2000, 23, pp. 1293-1297.

Arnardottir et al., "Resolvin D3 Is Dysregulated in Arthritis and Reduces Arthritic Inflammation", J Immunol, 2016, 197(6), pp. 2362-2368.

(Continued)

*Primary Examiner* — Sahar Javanmard
(74) *Attorney, Agent, or Firm* — Armstrong Teasdale LLP

(57) ABSTRACT

A method of treating or preventing cardiovascular disease which comprises administering a therapeutically effective amount of at least one n-3 DPA-derived resolvin and/or upregulating or increasing the biosynthesis or activity of at least one n-3 DPA-derived resolvin. n-3 DPA-derived resolvins are normally regulated diurnally in the body and are linked to activation of platelets and leucocytes and formation of platelet-leukocyte aggregates. Dysfunctional regulation of n-3 DPA-derived resolvins may lead to systemic inflammation because of excessive inflammation-inducing eicosanoids, especially in the early hours of the morning. Further, decreased 5-LOX/15-LOX expression and increased systemic adenosine concentrations are found to be associated with reduced resolvin levels and increased risk of cardiovascular disease. n-3 DPA-derived resolvins are administered to achieve maximum absorption in the early hours. Also disclosed are n-3 DPA-derived resolvins for use in the treatment or prevention of cardiovascular disease, and methods for measuring the levels of n-3 DPA-derived resolvins and/or the expression or activity of adenosine or 5-LOX/15-LOX in biological samples obtained from a subject for assessing the subject's risk of cardiovascular disease.

6 Claims, 25 Drawing Sheets

(56) References Cited

OTHER PUBLICATIONS

Birnbaum et al., "Augmentation of Myocardial Production of 15-Epi-Lipoxin-A4 by Pioglitazone and Atorvastatin in the Rat", Circulation, 2006, 114, pp. 929-935.
Brancaleone et al., "A vasculo-protective circuit centered on lipoxin A4 and aspirin-triggered 15-epi-lipoxin A4 operative in murine microcirculation", Blood, 2013, 122(4), pp. 608-617.
Chatterjee et al., "The pro-resolving lipid mediator maresin 1 (MaRI) attenuates inflammatory signaling pathways in vascular smooth muscle and endothelial cells", PLoS One, 2014, 9(11), pp e113480.
Chin et al., "Commercialization of microfluidic point-of-care diagnostic devices", Lab Chip, 2012, 12(12), pp. 2118-2134.
Chin et al., "Microfluidics-based diagnostics of infectious diseases in the developing world", Nature Medicine, 2011, 17, pp. 1015-1019.
Colas et al., "Impaired Production and Diurnal Regulation of Vascular RvD(n-3 DPA) Increase Systemic Inflammation and Cardiovascular Disease", Circulation Research, 2018, 122(6), pp. P855-P863.
Colas et al., "Identification and signature profiles for pro-resolving and inflammatory lipid mediators in human tissue", Am J Physiol Cell Physiol, 2014, 307, pp C39-C54.
Dalli et al., "Elucidation of novel 13-series resolvins that increase with atorvastatin and clear infections", Nature Medicine, 2015, 21(9). pp 1071-1075.
Dalli et al., "Novel n-3 Immunoresolvents: Structures and Actions", Scientific Reports, 2013, 3(1), pp. 8-9.
Dalli et al., "Vagal Regulation of Group 3 Innate Lymphoid Cells and the Immunoresolvent PCTR1 Controls Infection Resolution", Immunity, 2017, 46(1), pp. 92-105.
Dalli et al., "Human Sepsis Eicosanoid and Proresolving Lipid Mediator Temporal Profiles: Correlations With Survival and Clinical Outcomes", Crit Care Med, 2017, 45(1), pp. 58-68.
Dalli et al., "Specific lipid mediator signatures of human phagocytes: microparticles stimulate macrophage efferocytosis and pro-resolving mediators", Blood, 2012, 120(15), pp e60-e72.
Dominguez-Rodriguez et al., "Inflammatory Systemic Biomarkers in Setting Acute Coronary Syndromes—Effects of the Diurnal Variation", Current Drug Targets, 2009, 10(10), pp. 1001-1008.
Dona et al., "Resolvin EI, an EPA-derived mediator in whole blood, selectively counter-regulates leukocytes and platelets", Blood, 2008, 112(3), pp. 848-855.
El Kebir et al., "Resolvin E1 promotes phagocytosis-induced neutrophil apoptosis and accelerates resolution of pulmonary inflammation", Proc Natl Acad Sci USA, 2012, 109(37), pp. 14983-14988.
Fredman et al., "An imbalance between specialized pro-resolving lipid mediators and pro-inflammatory leukotrienes promotes instability of atherosclerotic plaques", Nat Commun, 2016, 7, pp. 12859.
Furman et al., "Circulating monocyte-platelet aggregates are an early marker of acute myocardial infarction", J Am Coll Cardiol, 2001, 38(4), pp. 1002-1006.
Gilbert et al., "Resolvin D1 Reduces Infarct Size Through a Phosphoinositide 3-Kinase/Protein Kinase B Mechanism", J Cardiovasc Pharmacol, 2015, 66(1), pp. 72-79.
Gittens et al., "Methods for Assessing the Effects of Galectins on Leukocyte Trafficking", Methods Mol Biol, 2015, 1207, pp. 133-151.
Gobbetti et al., "Protectin D1 n-3 DPA and resolvin DS n _3 n-3 DPA are effectors of intestinal protection", Proc Natl Acad Sci USA, 2017, 114(15), pp. 3963-3968.
Helgadottir et al., "Association between the gene encoding 5-lipoxygenase-activating protein and stroke replicated in a Scottish population", Am J Hum Genet, 2005, 76(3), pp. 505-509.
Huo et al., "Circulating activated platelets exacerbate atherosclerosis in mice deficient in apolipoprotein E", Nat Med, 2003, 9(1), pp. 61-67.
Huo et al., "Myeloid Bmal1 deletion increases monocyte recruitment and worsens atherosclerosis", FASEB J, 2017, 31(3), pp. 1097-1106.
Ingle et al., "Cardiomyocyte-specific Bmal1 deletion in mice triggers diastolic dysfunction, extracellular matrix response, and impaired resolution of inflammation", Am J Physiol Heart Circ Physiol, 2015, 309(11), pp H1827-H1836.
Kain et al., "Resolvin D1 activates the inflammation resolving response at splenic and ventricular site following myocardial infarction leading to improved ventricular function", J Mol Cell Cardiol, 2015, 84, pp. 24-35.
Khambata et al., "Anti-inflammatory actions of inorganic nitrate stabilize the atherosclerotic plaque", Proc Natt Acad Sci USA, 2017, 114(4), pp E550-E559.
Markworth et al., "Divergent shifts in lipid mediator profile following supplementation with n-3 docosapentaenoic acid and eicosapentaenoic acid", FASEB J, 2016, 30(11), pp. 3714-3725.
Mcalpine et al., "Circadian Influence on Metabolism and Inflammation in Atherosclerosis", Circ Res, 2016, 119(1), pp. 131-141.
Morin et al., "Anti-proliferative effects of a new docosapentaenoic acid monoacylglyceride in colorectal carcinoma cells", Prostaglandins Leukot Essent Fat Acids, 2013, 89, pp. 203-213.
Morin et al., "Docosapentaenoic acid monoacylglyceride reduces inflammation and vascular remodelling in experimental pulmonary hypertension" Am J Physiol Heart Circ Physiol, 2014, 307, pp H574-H586.
Morin et al., "Eicosapentaenoic acid and docosapentaenoic acid monoglycerides are more potent than docosahexaenoic acid monoglyceride to resolve inflammation in a rheumatoid arthritis model", Arthritis Res Ther, 2015, 17(142), pp. 1-12.
Muller et al., "Circadian variation in the frequency of onset of acute myocardial infarction", N Engl J Med, 1985, 313(21), pp. 1315-1322.
Murphy et al., "Dietary menhaden, seal, and corn oils differentially affect lipid and ex vivo eicosanoid and hiobarbituric acid-reactive substances generation in the guinea pig", Lipids, 1999, 34, pp. 115-124.
Murphy et al., "Diets enriched in menhaden fish oil, seal oil, or shark liver oil have distinct effects on the lipid and fatty acid composition of guinea pig heart", Mol Cell Biochem, 1997, 177, pp. 257-269.
Nakashima et al., "Impact of Morning Onset on the Incidence of Recurrent Acute Coronary Syndrome and Progression of Coronary Atherosclerosis in Acute Myocardial Infarction" Circ J, 2017, 81(3), pp. 361-367.
Norling et al., "Proresolving and cartilage-protective actions of resolvin D1 in inflammatory arthritis", JCI Insight, 2016, 1(5), pp e85922.
Norris et al., "A cluster of immunoresolvents links coagulation to innate host defense in human blood", Sci Signal, 2017, 10(490), pp. 1-11.
Pfluecke et al., "Monocyte-platelet aggregates and CD11b expression as markers for thrombogenicity in atrial fibrillation", Clin Res Cardiol, 2016, 105(4), pp. 314-322.
Planaguma et al., "Lovastatin decreases acute mucosal inflammation via 15-epi-lipoxin A 4", Mucosal Immunol, 2010, 3(3), pp. 270-279.
Puttonen et al., "Is shift work a risk factor for rheumatoid arthritis? The Finnish Public Sector study", Ann Rheum Dis, 2010, 69(4), pp. 779-780.
Ramakrishnan et al., "Platelet activating factor: A potential biomarker in acute coronary syndrome?", Cardiovasc Ther, 2017, 35(1), pp. 64-70.
Rathod et al., "Accelerated resolution of inflammation underlies sex differences in inflammatory responses in humans", J Clin Invest, 2017, 127(1), pp. 169-182.
Sakata et al., "Circadian fluctuations of tissue plasminogen activator antigen and plasminogen activator inhibitor-1 antigens in vasospastic angina", Am Heart J, 1992, 124(4), pp. 854-860.
Samuelsson, "Role of basic science in the development of new medicines: examples from the eicosanoid field", J Biol Chem, 2012, 287(13), pp. 10070-10080.

(56) References Cited

OTHER PUBLICATIONS

Scheer et al., "The human endogenous circadian system causes greatest platelet activation during the biological morning independent of behaviors", PLoS One, 2011, 6(9), pp e24549.
Serhan, "Treating inflammation and infection in the 21st century: new hints from decoding resolution mediators and mechanisms", FASEB J, 2017, 31, pp. 1273-1288.
Shea et al., "Existence of an endogenous circadian blood pressure rhythm in humans that peaks in the evening" Circ Res, 2011, 108(8), pp. 980-984.
Shinohara et al., "Cell-cell interactions and bronchoconstrictor eicosanoid reduction with inhaled carbon monoxide and resolvin D1", Am J Physiol Lung Cell Mol Physiol, 2014, 307(10), pp L746-L757.
Superko et al., "Statins personalized", Med Clin North Am, 2012, 96(1), pp. 123-139.
Tsuji et al., "Docosapentaenoic acid (22:5, n-3) suppressed tube-forming activity in endothelial cells induced by vascular endothelial growth factor", Prostaglandins Leukot Essent Fat Acids, 2003, 68, pp. 337-342.
Walker et al., "13-Series resolvins mediate the leukocyte-platelet actions of atorvastatin and pravastatin in inflammatory arthritis", The FASEB Journal, 2017, 31(8), pp. 3636-3648.
Yang et al., "Metabolomics-Lipidomics of Eicosanoids and Docosanoids Generated by Phagocytes", Current Protocols in Immunology, 2011, 95(1), pp. 14.26.1-14.26.26.
Zhang et al., "Resolvin D2 Enhances Postischemic Revascularization While Resolving Inflammation", Circulation, 2016, 134(9), pp. 666-680.

* cited by examiner

METHODS FOR ASSESSING RISK OF CARDIOVASCULAR DISEASE AND METHODS AND COMPOUNDS FOR USE IN TREATING OR PREVENTING CARDIOVASCULAR DISEASE

FIELD OF THE INVENTION

The present invention relates to methods for assessing a risk of cardiovascular disease or myocardial infarction in a human subject, and has particular reference to methods for assessing the risk of cardiovascular disease or myocardial infarction in the early hours of the morning. The invention also provides methods for assessing the efficacy of prophylactic treatments for reducing the risk of cardiovascular disease or myocardial infarction. Further, the present invention provides methods of treating or preventing cardiovascular disease or myocardial infarction, particularly cardiovascular disease or myocardial infarction that occurs in the early hours of the morning, and compounds for use in such methods.

BACKGROUND TO THE INVENTION

Circadian mechanisms are central to regulating a number of physiological functions, including cardiovascular function and the immune system (Ingle K A et al. Cardiomyocyte-specific Bmal1 deletion in mice triggers diastolic dysfunction, extracellular matrix response, and impaired resolution of inflammation. *Am J Physiol Heart Circ Physiol.* 2015; 309(11):H1827-1836; McAlpine C S & Swirski F K. Circadian Influence on Metabolism and Inflammation in Atherosclerosis. *Circ Res.* 2016; 119(1):131-141). Disturbances to these fundamental mechanisms are thought to be responsible for many diseases that are characterised by a dysregulated inflammatory response, including cardiovascular and metabolic disorders (Ingle K A et al., 2015; McAlpine C S & Swirski F K, 2016; Puttonen S et al. Is shift work a risk factor for rheumatoid arthritis? The Finnish Public Sector study. *Ann Rheum Dis.* 2010; 69(4):779-780). Circadian responses have been correlated with several inflammatory conditions, including myocardial infarct (Gilbert K et al. Resolvin D1 Reduces Infarct Size Through a Phosphoinositide 3-Kinase/Protein Kinase B Mechanism. *J Cardiovasc Pharmacol.* 2015; 66(1):72-79; Kain V et al. Resolvin D1 activates the inflammation resolving response at splenic and ventricular site following myocardial infarction leading to improved ventricular function. *J Mol Cell Cardiol.* 2015; 84:24-35).

In the vasculature, platelet activation is at a maximum during the early hours of the day with the upregulation of several activation markers, including CD62P (Scheer F A et al. The human endogenous circadian system causes greatest platelet activation during the biological morning independent of behaviors. *PLoS One.* 2011; 6(9):e24549). This increase in platelet activation is coincident with an increase in plasma plasminogen activator inhibitor-1, a serine protease inhibitor that functions as the principal inhibitor of tissue plasminogen activator and urokinase, thereby increasing the risk of thrombosis (Sakata K et al. Circadian fluctuations of tissue plasminogen activator antigen and plasminogen activator inhibitor-1 antigens in vasospastic angina. *Am Heart J.* 1992; 124(4):854-860).

Platelet CD62P mediates platelet-leukocyte interactions, a process which, in addition to facilitating leukocyte recruitment to the vascular endothelium, is also involved in leukocyte activation and the production of inflammatory mediators, including cysteinyl leukotrienes (Shinohara M et al. Cell-cell interactions and bronchoconstrictor eicosanoid reduction with inhaled carbon monoxide and resolvin D1. *Am J Physiol Lung Cell Mol Physiol.* 2014; 307(10):L746-757), tumour necrosis factor-α and C—C motif ligand-2 (Furman M I et al. Circulating monocyte-platelet aggregates are an early marker of acute myocardial infarction. *J Am Coll Cardiol.* 2001; 38(4):1002-1006; Pfluecke C et al. Monocyte-platelet aggregates and CD11b expression as markers for thrombogenicity in atrial fibrillation. *Clin Res Cardiol.* 2016; 105(4):314-322). CD62P enhances platelet adhesion to endothelial cells expressing fractalkine and triggers the release of Weibel-Palade-bodies in endothelial cells, perpetuating the pro-inflammatory and pro-thrombotic status during the early hours of the day.

Platelet-leukocyte aggregates are also implicated in vascular disease pathogenesis, including atherosclerosis (Huo Y et al. Circulating activated platelets exacerbate atherosclerosis in mice deficient in apolipoprotein E. *Nat Med.* 2003; 9(1):61-67).

Meanwhile, platelet activating factor (PAF) has a reported role in propagating vascular inflammation (Palur Ramakrishnan A V et al. Platelet activating factor: A potential biomarker in acute coronary syndrome? *Cardiovasc Ther.* 2017; 35(1):64-70).

These observations suggest that in healthy individuals endogenous, diurnally regulated, protective mechanisms are engaged that counter-regulate this physiological inflammation to prevent vascular inflammation and thrombus formation.

Studies investigating mechanisms engaged by the host to terminate ongoing inflammation have uncovered a new genus of molecules, produced by leukocytes that reprogram both stromal and leukocyte responses (Dalli J et al. Elucidation of novel 13-series resolvins that increase with atorvastatin and clear infections. *Nat Med.* 2015; 21(9):1071-1075; Dalli J et al. Novel n-3 immunoresolvents: structures and actions. *Sci Rep.* 2013; 3:1940; Fredman G et al. An imbalance between specialized pro-resolving lipid mediators and pro-inflammatory leukotrienes promotes instability of atherosclerotic plaques. *Nat Commun.* 2016; 7:12859; Serhan C N. Treating inflammation and infection in the 21st century: new hints from decoding resolution mediators and mechanisms. *FASEB J.* 2017; El Kebir D et al. Resolvin E1 promotes phagocytosis-induced neutrophil apoptosis and accelerates resolution of pulmonary inflammation. *Proc Natl Acad Sci USA.* 2012; 109(37):14983-14988; Zhang M J et al. Resolvin D2 Enhances Postischemic Revascularization While Resolving Inflammation. *Circulation.* 2016; 134(9):666-680). These molecules, termed specialised pro-resolving mediators (SPM), are produced via the enzymatic conversion of essential fatty acids are classified into four families: the lipoxins, resolvins, protectins and maresins (Serhan C N, 2017).

The structures of SPM have been found to be conserved throughout evolution, including tunicates, mice and baboons as well as humans, facilitating the direct translation of findings made in experimental systems to humans and vice versa.

SPM actively counter-regulate the production of pro-inflammatory mediators, including cytokines and eicosanoids, without interfering with the immune response, and regulate leukocyte trafficking and phenotype following both sterile and infectious challenge (Dalli J et al. 2015; Dalli J et al. 2013; Fredman G et al. 2016; Serhan C N. 2017; El Kebir D et al. 2012; Zhang M J et al. 2016; Dona M et al. Resolvin E1, an EPA-derived mediator in whole blood, selectively counter-regulates leukocytes and platelets. *Blood.* 2008; 112(3):848-855).

In addition to having biological actions in peripheral organs, evidence indicates that these molecules may regulate processes occurring in the vasculature (Zhang M J et al. 2016; Chatterjee A et al. The pro-resolving lipid mediator maresin 1 (MaR1) attenuates inflammatory signaling pathways in vascular smooth muscle and endothelial cells. *PLoS One.* 2014; 9(11):e113480). In this context, the eicosapentaenoic acid-derived resolvin (RvE1) potently regulates platelet activation (Dona M et al. 2008); maresin (MaR)1 and RvD2 protect against neointimal hyperplasia (Chatterjee A et al. 2014; Akagi D, Chen M, Toy R, Chatterjee A, Conte M S. Systemic delivery of proresolving lipid mediators resolvin D2 and maresin 1 attenuates intimal hyperplasia in mice. *FASEB J.* 2015; 29(6):2504-2513); RvD1 promotes plaque stability in murine atherosclerosis (Fredman G et al. 2016). Furthermore, plasma SPM concentrations have been reported to reflect outcome in sepsis (Dalli J et al. Human Sepsis Eicosanoid and Proresolving Lipid Mediator Temporal Profiles: Correlations With Survival and Clinical Outcomes. *Crit Care Med.* 2017; 45(1):58-68) and increased plasma SPM in females are associated with improved endothelial function following challenge when compared with males (Rathod K S et al. Accelerated resolution of inflammation underlies sex differences in inflammatory responses in humans. *J Clin Invest.* 2017; 127(1):169-182).

Pro-resolving mediators are produced via the stereoselective conversion of essential fatty acids by enzymes that in the vasculature are primarily expressed in leukocytes. The n-3 DPA-derived resolvin biosynthetic pathway, for example, is initiated by the conversion of n-3 DPA to 17S-hydroperoxy-docosapentaenoic acid, which is catalysed by leukocyte 15-lipoxygenase (15-LOX), followed by conversion to $RvD_{n\text{-}3\ DPA}$ by leukocyte 5-LOX (Dalli J et al. 2013).

Tissue pro-resolving mediator biosynthesis is also regulated by the vagus nerve via release of the neurotransmitter acetylcholine (ACh), a mechanism that is central in maintaining tissue resolution tone (Dalli J et al. Vagal Regulation of Group 3 Innate Lymphoid Cells and the Immunoresolvent PCTR1 Controls Infection Resolution. *Immunity.* 2017; 46(1):92-105).

n-3 DPA has been characterised as an inhibitor of platelet aggregation (Akiba S et al. Involvement of lipoxygenase pathway in docosapentaenoic acid-induced inhibition of platelet aggregation. *Biol. Pharm. Bull.* 2000; 23:1293-1297; Murphy M G et al. Diets enriched in menhaden fish oil, seal oil, or shark liver oil have distinct effects on the lipid and fatty-acid composition of guinea pig heart. *Mol. Cell. Biochem.* 1997; 177:257-269; Murphy M G et al. Dietary menhaden, seal, and corn oils differentially affect lipid and ex vivo eicosanoid and thiobarbituric acid-reactive substances generation in the guinea pig. *Lipids.* 1999; 34:115-124) and angiogenesis where it acts as a suppressor of expression of the vascular endothelial-cell growth factor receptor 2 (Tsuji M et al. Docosapentaenoic acid (22:5, n-3) suppressed tube-forming activity in endothelial cells induced by vascular endothelial growth factor. *Prostaglandins Leukot. Essent. Fat. Acids.* 2003; 68:337-342).

Furthermore, recent data indicate an anti-inflammatory effect of n-3 DPA in models of pulmonary hypertension (Morin C et al. Docosapentaenoic acid monoacylglyceride reduces inflammation and vascular remodelling in experimental pulmonary hypertension. *Am. J. Physiol. Heart Circ. Physiol.* 2014; 307:H574H586) and arthritis (Morin C et al. Eicosapentaenoic acid and docosapentaenoic acid mono-glycerides are more potent than docosahexaenoic acid mono-glyceride to resolve inflammation in a rheumatoid arthritis model. *Arthritis Res. Ther.* 2015; 17:142) and anti-proliferative effects in colon cancer cells (Morin C et al. Anti-proliferative effects of a new docosapentaenoic acid monoacylglyceride in colorectal carcinoma cells. *Prostaglandins Leukot. Essent. Fat. Acids.* 2013; 89:203-213).

An object of the present invention is to provide a method for assessing whether a patient is at risk of cardiovascular disease, including myocardial infarction. In particular, it is an object of the invention to provide a method for assessing whether a patient is at risk of cardiovascular disease owing to inadequate control of platelet and/or leukocyte activation, especially early in the morning.

Another object of the present invention is to provide a method for assessing the efficacy of a preventative treatment for cardiovascular disease, including myocardial infarction, especially a treatment aimed at reducing cardiovascular inflammation.

A different object of the invention is to provide a method for treating or preventing cardiovascular disease, including myocardial infarction, and compounds for use in such a method, especially cardiovascular disease that is mediated by inadequate diurnal control of platelet and/or leukocyte activation.

SUMMARY OF THE INVENTION

Using lipid mediator profiling and healthy volunteers, as disclosed in Examples 1 and 9 below, diurnal changes in certain D-series resolvins that peak during the early morning hours (e.g. between 7 AM and 9 AM) have been discovered. As disclosed in Examples 5 and 13 below, lipid mediator profiling of plasma from patients at risk of myocardial infarction demonstrated reductions in n-3 docosapentaenoic acid (DPA)-derived resolvins that were associated with increased activation of peripheral blood platelets and leukocytes.

As disclosed in Examples 3, 5, 11 and 13, incubation of patient peripheral blood with n-3 DPA-derived resolvins significantly reduced cellular activation. Furthermore, administration of n-3 DPA-derived resolvins to Apolipoprotein E deficient mice significantly reduced platelet-leukocyte aggregates and vascular disease, as disclosed in Examples 6 and 14.

Using lipid mediator profiling and healthy volunteers we found that plasma n-3 docosapentaenoic acid-derived D-series resolvins ($RvD_{n\text{-}3\ DPA}$) concentrations were selectively regulated in a diurnal manner. Lipid mediator profiling of plasma from patients at risk of myocardial infarct demonstrated reductions in $RvD_{n\text{-}3\ DPA}$ that was associated with a decreased 5-lipoxygenase expression and increased systemic adenosine concentrations. We also found a significant negative correlation between plasma $RvD_{n\text{-}3\ DPA}$ and markers of platelet, monocyte and neutrophil activation including CD63 and CD11b. Incubation of $RvD_{n\text{-}3\ DPA}$ with peripheral blood from healthy volunteers and patients with cardiovascular disease significantly and dose-dependently decreased platelet and leukocyte activation. Furthermore, administration of $RvD5_{n\text{-}3\ DPA}$ to apolipoprotein E deficient mice significantly reduced platelet-leukocyte aggregates, vascular thromboxane B2 concentrations and aortic lesions.

These results demonstrate that peripheral blood $RvD_{n\text{-}3\ DPA}$ are diurnally regulated in humans and dysregulation in the production of these mediators may lead to cardiovascular disease.

The present invention therefore relates to the use of n-3 DPA-derived resolvins for diagnosing, treating or preventing diseases or conditions that are mediated and/or exacerbated by dysfunction in the circadian control of platelet and/or leukocyte activation and for assessing the efficacy of medicines for treating or preventing such diseases or conditions. Such diseases and conditions include, without limitation, cardiovascular disease, including coronary artery disease, vascular inflammation and myocardial infarction.

In accordance with one aspect of the present invention therefore there is provided an n-3 DPA-derived resolvin for use in a method of treating or preventing cardiovascular disease.

In accordance with the present invention, a therapeutically effective amount of one or more n-3 DPA-derived resolvins may be administered to a patient suffering from or at risk of cardiovascular disease.

In accordance with another aspect of the present invention therefore there is provided a method of treating or preventing cardiovascular disease which comprises administering a therapeutically effective amount of at least one n-3 DPA-derived resolvin to a subject in need thereof. The present invention further comprehends a method of treating or preventing cardiovascular disease which comprises upregulating the biosynthesis, expression or activity of at least one n-3 DPA-derived resolvin in a subject in need thereof. In particular, the invention provides a method of treating or preventing cardiovascular disease which comprises reducing adenosine activity or expression in a subject in need thereof, and/or increasing 5-LOX and/or 15-LOX activity or expression in a subject in need thereof.

In accordance with the invention, the n-3 DPA-derived resolvin(s) are administered to the subject and/or the biosynthesis, expression or activity of the n-3 DPA-derived resolvin(s) is upregulated in such a way that peak n-3 DPA-derived resolvin plasma concentration is achieved in the early hours of the morning, at least between about 7 AM and 9 AM, as described in more detail below.

As used herein, "cardiovascular disease" includes coronary heart disease, strokes and transient ischaemic attack, peripheral arterial disease and aortic disease. Coronary heart disease includes angina, myocardial infarction and heart failure. Aortic disease includes aortic aneurysm.

In another aspect, therefore, the present invention comprehends methods of treating or preventing systemic inflammation and/or myocardial infarction by administering a therapeutically effective amount of at least one n-3 DPA-derived resolvin to a subject in need thereof and/or by upregulating the biosynthesis, expression or activity of at least one n-3 DPA-derived resolvin in a subject in need thereof, for example by reducing adenosine activity or expression levels and/or increasing 5-LOX and/or 15-LOX activity or expression levels in the subject.

In yet another aspect, the present invention comprises treating dysfunctional diurnal regulation of n-3 DPA-derived resolvins by administering a therapeutically effective amount of at least one n-3 DPA-derived resolvin to a subject in need thereof and/or by upregulating the biosynthesis, expression or activity of at least one n-3 DPA-derived resolvin in a subject in need thereof, for example by reducing adenosine activity or expression levels and/or by increasing 5-LOX and/or 15-LOX activity or expression levels in the subject.

Suitably, one or more n-3 DPA-derived resolvins are administered to a subject and/or the biosynthesis, expression or activity of one or more n-3 DPA-derived resolvin(s) is upregulated in a subject in accordance with the present invention such that $t_{max}$ occurs in the early hours of the morning. The duration of action should extend through the early hours of the morning; for example, from at least as early as 7 AM until at least as late as 9 AM. Onset of action may occur between about 5:30 AM-7 AM. Termination of action may occur between about 9 AM-10:30 AM, but in some embodiments the n-3 DPA-derived resolvins may continue to be absorbed over a longer period of time, depending on how the n-3 DPA-derived resolvins are formulated for delivery. The duration of action should be at least 90 mins and preferably at least 2 hrs. In some embodiments, the duration of action may be up to 3 hrs, 4 hrs or longer.

The one or more n-3 DPA-derived resolvins may be formulated for immediate release.

Alternatively, the one or more n-3 DPA-derived resolvins may be formulated for delayed and/or controlled release such that the duration of action extends through the early hours of the morning, as described above.

Thus, in some embodiments, the one or more n-3 DPA-derived resolvins may be formulated as a delayed release dosage form, such that the dosage form may be taken before the subject goes to bed, and release of the one or more n-3 DPA-derived resolvins is delayed or substantially delayed until the early hours of the morning.

In some embodiments, the one or more n-3 DPA-derived resolvins may be formulated for controlled release such that the plasma levels of the one or more n-3 DPA-derived resolvins remain above the minimum effective concentration (MEC) throughout the early hours of the morning.

In some embodiments, the one or more n-3 DPA-derived resolvins may be formulated for delayed and controlled release.

Suitably, the one or more n-3 DPA-derived resolvins may be formulated to provide a peak plasma concentration of the one or more n-3 DPA-derived resolvins of at least 10 pg/mL, preferably at least 15 pg/mL or 20 pg/mL, throughout the early hours of the morning.

Whilst the one or more n-3 DPA-derived resolvins may be administered via any accepted mode of administration for agents for treating or preventing cardiovascular disease, including orally, sublingually, intravenously, intranasally, topically, transdermal, intraperitoneally, intramuscularly, intrapulmonary, vaginally or rectally, oral administration may be preferred in some embodiments.

n-3 DPA-derived resolvins are highly soluble by virtue of their hydroxy groups. The person skilled in the art will be aware of numerous suitable formulations for immediate, delayed or controlled release of one or more n-3 DPA-derived resolvins to achieve the desired plasma drug concentration-time profile. Brief details of suitable formulations and dosage forms are described below.

Advantageously, administration of an n-3 DPA-derived resolvin to a subject in accordance with the present invention may result in reduced activation of platelets and/or leucocytes, particularly monocytes. Activation of platelets and white blood cells may be measured by reference to activation markers known to those skilled in the art such, for example, as CD62P, CD11b or CD41.

In yet another aspect of the present invention, therefore, there is provided a method of controlling activation of platelets and/or leukocytes in a subject in need thereof, which comprises administering a therapeutically effective amount of at least one n-3 DPA-derived resolvin.

Advantageously, administration of an n-3 DPA-derived resolvin to a subject in accordance with the present invention may result in reduced formation of platelet-leukocyte aggregates.

Accordingly, in yet another aspect the present invention, therefore, there is provided a method of reducing formation of platelet-leukocyte aggregates in a subject in need thereof, which comprises administering a therapeutically effective amount of at least one n-3 DPA-derived resolvin and/or upregulating the biosynthesis, expression or activity of at least one n-3 DPA-derived resolvin in a subject in need thereof, for example by reducing adenosine activity or expression levels and/or by increasing 5-LOX and/or 15-LOX activity or expression levels in the subject.

The n-3 DPA-derived resolvin for use in accordance with the present invention is derived from omega-3 docosapentaenoic acid (n-3 DPA).

In some embodiments, the n-3 DPA-derived resolvin may be $RvD1_{n\text{-}3\ DPA}$ (7,8,17-trihydroxy-9,11,13,15E,19Z-docosapentaenoic acid) represented by Formula I below:

Formula I

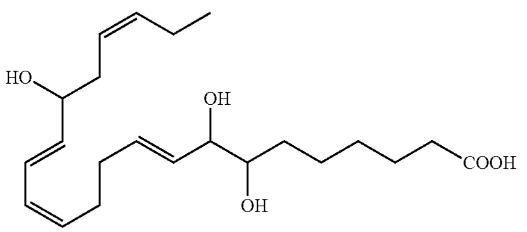

In some embodiments, the n-3 DPA-derived resolvin may be $RvD2_{n\text{-}3DPA}$ (7,16,17-trihydroxy-8,10,12,14E,19Z-docosapentaenoic acid) represented by Formula II below Formula II

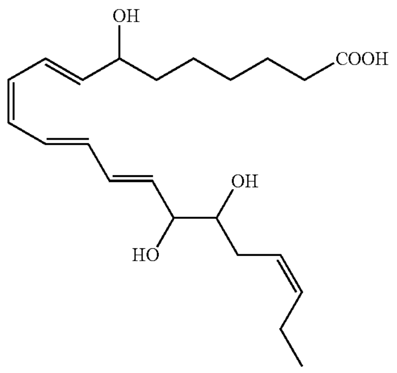

In some embodiments, the n-3 DPA-derived resolvin may be $RvD5_{n\text{-}3\ DPA}$ (7,17-trihydroxy-8E,10,13,15E,19Z-docosapentaenoic acid) represented by Formula III below:

Formula III

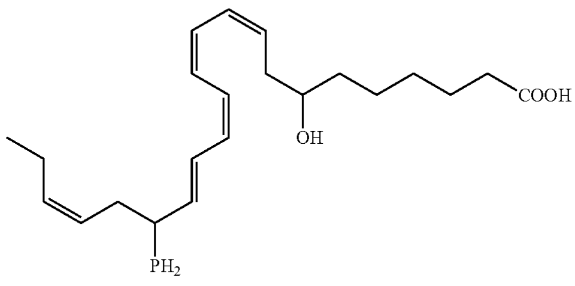

In some embodiments, more than one n-3 DPA-derived resolvin may be administered to the subject. In particular, a combination of two or more n-3 DPA-derived resolvins may be used. Suitably, the n-3 DPA-derived resolvins may all be n-3 DPA-derived resolvins.

In some embodiments, one or more n-3 DPA-derived resolvins may be administered in combination with one or more other active agents, including, for example, one or more other lipid mediators such as resolvins, including DHA-derived resolvins and/or with one or more agents which are capable of increasing the biosynthesis, expression or activity of one or more n-2 DPA-derived resolvins, for example by reducing the expression or activity of adenosine and/or by increasing 5-LOX and/or 15-LOX activity or expression in the subject.

In some embodiments, two or more n-3 DPA-derived resolvins may be administered simultaneously to the subject. Alternatively, two or more n-3 DPA-derived resolvins may be administered separately or sequentially to the subject.

The one or more n-3 DPA-derived resolvins may be formulated with one or more pharmaceutically acceptable excipients.

Accordingly, in yet another aspect of the present invention, there is provided a pharmaceutical composition comprising one or more n-3 DPA-derived resolvins and one or more pharmaceutically acceptable excipients.

As used herein, the term "pharmaceutically acceptable" refers to those excipients which are, within the scope of sound medical judgment, suitable for use in contact with the tissues of human beings and animals without excessive toxicity, irritation or other problem or complication.

As described above, the pharmaceutical composition of the invention may be formulated for immediate, delayed or controlled release of the one or more n-3 DPA-derived resolvins to provide peak plasma concentration of the n-3 DPA-derived resolvins in the subject's blood in the early hours of the morning according to a desired dosage regimen.

Pharmaceutical compositions or formulations of the invention include solid, semi-solid, liquid and aerosol dosage forms such, for example, as tablets, capsules, powders, liquids, suspensions, suppositories and aerosols.

The one or more n-3 DPA-derived resolvins may be administered either alone or in combination with a pharmaceutical carrier or excipient (e.g. mannitol, lactose, starch, magnesium stearate, sodium saccharine, talcum, cellulose, sodium croscarmellose, glucose, gelatin, sucrose or magnesium carbonate). If desired, the pharmaceutical composition may also contain minor amounts of non-toxic auxiliary substances such as wetting agents, emulsifying agents, solubilising agents, pH buffering agents and the like (e.g. sodium acetate, sodium citrate, cyclodextrin derivatives, sorbitan monolaurate, triethanolamine acetate or triethanolamine oleate).

Generally, depending on the intended mode of administration, the pharmaceutical composition may contain about 0.005% to 95% wt., in some embodiments about 0.5% to 50% by weight, of the one or more n-3 DPA-derived resolvins. Methods of preparing such dosage forms are known, or will be apparent, to those skilled in the art; for example, see *Remington Pharmaceutical Sciences* (full reference below).

In some embodiments, the pharmaceutical composition may take the form of a pill or tablet, and thus the composition may contain, along with the one or more n-3 DPA-derived resolvins, a diluent such, for example, as lactose, sucrose or dicalcium phosphate; a lubricant such, for example, as magnesium stearate; and a binder such, for example, as starch, gum acacia, polyvinyl pyrrolidine, gelatin, cellulose or cellulose derivatives. In another solid dosage form in accordance with the invention, a powder, marume, solution or suspension (e.g. in propylene carbonate, vegetable oils or triglycerides) may be encapsulated in a gelatin capsule.

Liquid pharmaceutically administrable compositions can, for example, be prepared by dissolving or dispersing at least one n-3 DPA-derived resolvin and optional pharmaceutical adjuvants in a carrier (e.g. water, saline, aqueous dextrose, glycerol, glycols or ethanol) to form a solution or suspension. Injectables can be prepared in conventional forms, either as liquid solutions or suspensions, as emulsions or in solid forms suitable for dissolution or suspension in liquid prior to injection. The percentage of one or more n-3 DPA-derived resolvins contained in such parenteral compositions may be dependent on the specific nature thereof, as well as the activity of the chemical entities and the needs of the subject. However, percentages of one or more n-3 DPA-derived resolvins of 0.01% to 10% wt. in solution may be employable and may be higher if the composition is a solid which will be subsequently diluted to the above percentages. In certain embodiments, the composition may comprise from about 0.2 to 2% wt. of the one or more n-3 DPA-derived resolvins in solution.

Pharmaceutical compositions of the one or more n-3 DPA-derived resolvins described herein may also be administered to the respiratory tract as an aerosol or solution for a nebuliser or as a microfine powder for insufflation, alone or in combination with an inert carrier such, for example, as lactose. In such a case, the particles of the pharmaceutical composition have diameters of less than 50 microns, in certain embodiments, less than 10 microns.

In general, the one or more n-3 DPA-derived resolvins may be administered in a therapeutically effective amount by any of the accepted modes of administration for agents that serve similar utilities. The actual amount of the chemical entity, i.e. the active ingredient, may depend upon a number of factors such, for example, as the severity of the disease to be treated, the age and relative health of the subject, the potency of the chemical entity used the route and form of administration and other factors.

Suitably, the pharmaceutical composition may be administered once or more than once per day.

Therapeutically effective amounts of the chemical entities described herein may range from approximately 0.01 to 200 mg per kilogram body weight of the subject per day; such, for example, as about 0.01-100 mg/kg/day; e.g. from about 0.1 to 50 mg/kg/day. For administration to a 70 kg to 100 kg person, the dosage range may be about 0.5-3500 mg per day.

In general, the one or more n-3 DPA-derived resolvins may be administered as a pharmaceutical composition by any one of the following routes: oral, systemic (e.g. transdermal, intranasal or by suppository) or parenteral (e.g. intramuscular, intravenous or subcutaneous) administration.

In some embodiments, oral administration may be used.

Compositions can take the form of tablets, pills, capsules, semisolids, powders, sustained release formulations, solutions, suspensions, elixirs, aerosols or any other appropriate compositions. Another manner for administering the provided chemical entities is inhalation.

The choice of formulation depends on various factors such as the mode of drug administration and bioavailability of the drug substance. For delivery via inhalation, one or more n-3 DPA-derived resolvins can be formulated as a liquid solution, suspension, aerosol propellant or dry powder and loaded into a suitable dispenser for administration. There are several types of pharmaceutical inhalation devices-nebuliser inhalers, metered dose inhalers (MDI) and dry powder inhalers (DPI). Nebuliser devices produce a stream of high velocity air that causes the therapeutic agents (which are formulated in a liquid form) to spray as a mist that is carried into the subject's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free-flowing powder that can be dispersed in the subject's inspiratory air-stream during breathing by the device. In order to achieve a free-flowing powder, the one or more n-3 DPA-derived resolvins may be formulated with an excipient such as lactose. A measured amount of the one or more n-3 DPA-derived resolvins may be stored in a capsule form and dispensed with each actuation.

The pharmaceutical composition of the invention, in general, comprises at least one n-3 DPA-derived resolvin in combination with at least one pharmaceutically acceptable excipient. Acceptable excipients are non-toxic, aid administration and do not adversely affect the therapeutic benefit of the at least one n-3 DPA-derived resolvin. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride and dried skim milk. Liquid and semisolid excipients may be selected from glycerol, propylene glycol, water, ethanol and various oils, including those of petroleum, animal, vegetable or synthetic origin, e.g. peanut oil, soybean oil, mineral oil, sesame oil, etc. Liquid carriers, for injectable solutions, include water, saline, aqueous dextrose and glycols.

Compressed gases may be used to disperse one or more n-3 DPA-derived resolvins in aerosol form. Inert gases suitable for this purpose are nitrogen, carbon dioxide, etc. Other suitable pharmaceutical excipients and their formulations are described in *Remington's Pharmaceutical Sciences*, edited by E. W. Martin (Mack Publishing Company, 18th ed., 1990).

The amount of the one or more n-3 DPA-derived resolvins in a pharmaceutical composition can vary within the full range employed by those skilled in the art. Typically, the composition will contain, on a weight percent (wt. %) basis, from about 0.01-99.99 wt. % of at least one n-3 DPA-derived resolvin based on the total composition, with the balance being one or more suitable pharmaceutical excipients. In certain embodiments, the at least one n-3 DPA-derived resolvin is present at a level of about 1-80 wt. %.

As described above, the one or more n-3 DPA-derived resolvins may be administered to the subject in delayed or controlled release dosage forms such that the duration of action of the n-3 DPA-derived resolvins occurs in the early morning, at least between 7 AM and 9 AM. In some embodiments, the delayed or controlled release dosage forms may provide a sufficient delay between administering the dosage form and the onset of action to allow the dosage form to be taken in the evening, before the subject goes to bed, for example between 9 PM and 11 PM, with the onset of action occurring in the early hours of the morning, for example not earlier than 5 AM.

Suitable delayed or controlled release dosage forms include depot injections, osmotic pumps, pills, transdermal (including electrotransport) patches and the like, for prolonged and/or timed, pulsed administration at a predetermined rate.

In certain embodiments, the compositions may be provided in unit dosage forms suitable for single administration of a precise dose.

In some embodiments, an oral delayed or controlled release dosage form may be employed that is designed to provide release and plasma profiles that include a first lag phase followed by a release phase. The release profiles may be sigmoidal. By providing such profiles, the dosage form may provide a timed, prolonged therapeutic effect when taken once a day.

A suitable delayed or controlled release dosage form may comprise a single population of beads that can be administered in a capsule or a liquid or gel suspension containing the beads.

In some embodiments, the beads may have a bead structure having a drug-containing core, which includes one or more n-3 DPA-derived resolvins, excipients and optionally a superdisintegrant or osmagent. The core may include, for example, one or more n-3 DPA-derived resolvins, a disintegrant, an osmagent or pore-forming agent and a binder.

In embodiments in which a plurality of n-3 DPA-derived resolvins are administered to the subject, each bead may conveniently be loaded with a single species of n-3 DPA-derived resolvin. In some embodiments, this may allow the relative proportions of different n-3 DPA-derived resolvins to be controlled.

An exemplary core may include about 20-25% wt. n-3 DPA-derived resolvin, about 45-60% wt. microcrystalline cellulose, about 10-30% wt. potassium chloride and about 3-5% wt. binder such as polyvinyl pyrrolidone or hydroxypropyl cellulose.

The drug containing core can be made by a variety of processes known in the art, including wet granulation, extrusion, and spheronisation.

In some embodiments, two layers may cover the core; a first intermediate layer as a sustained release layer, and an outer layer as a delayed release layer that is optionally pH dependent.

In some embodiments, the core may be an inert non-pareil bead. The inner core may be a bead of sugar and starch or it can be composed of microcrystalline cellulose. Any spherical bead that is suitable for forming the core bead and is pharmaceutically acceptable can be used. In such embodiments, the one or more n-3 DPA-derived resolvins and excipients of the core may be layered onto the core bead, providing a three-layer formulation. An outermost layer may be a delayed release or an enteric coating. In certain embodiments, the outermost layer may comprise a water-soluble polymer, a water-insoluble polymer, a plasticiser and a lubricant. The time of delay of drug release may be controlled by the ratio of water-soluble and insoluble polymers, the plasticiser concentration, amount of lubricant and the coating weight gain, which may be up to 35-45%. wt. Alternatively, the outermost layer may be a pH dependent polymer that dissolves at pH above about 5.5.

A sustained release layer is designed to provide a slower initial rate of release that increases over a period of up to 8-10 hours after the layer is exposed to an aqueous environment. An increasing drug profile can be achieved by a membrane that becomes more permeable over time. An example of a sustained release layer includes a water-soluble polymer, a water-insoluble polymer, a plasticiser and a lubricant. The rate of drug release can be controlled or sustained by varying the ratio of water-soluble and water-insoluble polymers and by varying the coating thickness up to about 15-45% wt. gain.

In an alternative embodiment, a swellable layer, including a superdisintegrant or osmotic agent, may be disposed between the core and the sustained release layer.

In some embodiments, the controlled or delayed release dosage form may comprise a plurality of layers. The dosage form may include an inner core of a non-pareil bead and four concentric layers from inner to outer described as, a swelling polymer layer, drug layer, a sustained release layer and a pH-dependent delayed release layer, which may be a pH dependent layer.

In some embodiments, the four-layer composition may be made in a step-wise fashion. In a first step, a hydrophilic polymer suspended in ethanol with a binder is coated onto nonpareil beads to a 30-50% wt. gain. In some embodiments PolyOx Coagulant SFP (PEO) marketed by the Dow Chemical Company may be the hydrophilic polymer, and hydroxypropyl cellulose (HPC LF) may be added as the binder. The PolyOx layer may then be sealed with a hydroxypropyl cellulose such as Klucel® EF to a 10% wt. gain. The active pharmaceutical ingredient (API) may then be suspended in ethanol with a binder and coated onto the layered bead and the sustained release and delayed release coatings may be applied as described herein.

In some embodiments, the core may comprise a minitablet rather than a bead. The core and layers may be functionally the same as the layers on the beads, except there is no optional inert core.

Various water-soluble polymers may be used in the delayed or controlled release dosage form. Such polymers include, but are not limited to polyethylene oxide (PEO), ethylene oxide-propylene oxide co-polymers, polyethylene-polypropylene glycol (e.g. poloxamer), carbomer, polycarbophil, chitosan, polyvinyl pyrrolidone (PVP), polyvinyl alcohol (PVA), hydroxyalkyl celluloses such as hydroxypropyl cellulose (HPC), hydroxyethyl cellulose, hydroxymethyl cellulose and hydroxypropyl methylcellulose, sodium carboxymethyl cellulose, methylcellulose, hydroxyethyl methylcellulose, hydroxypropyl methylcellulose, polyacrylates such as carbomer, polyacrylamides, polymethacrylamides, polyphosphazines, polyoxazolidines, polyhydroxyalkylcarboxylic acids, alginic acid and its derivatives such as carrageenate alginates, ammonium alginate and sodium alginate, starch and starch derivatives, polysaccharides, carboxypolymethylene, polyethylene glycol, natural gums such as gum guar, gum acacia, gum tragacanth, karaya gum and gum xanthan, povidone, gelatin and the like.

In some embodiments, at least the delayed release layer may include one or more polymers such as an acrylic polymer, acrylic copolymer, methacrylic polymer or methacrylic copolymer, including, but not limited to, EUDRAGIT® L100, EUDRAGIT® L100-55, EUDRAGIT® L 30 D-55, EUDRAGIT® 5100, EUDRAGIT® 4135F, EUDRAGIT® RS, acrylic acid and methacrylic acid copolymers, methyl methacrylate, methyl methacrylate copolymers, ethoxyethyl methacrylates, cyanoethyl methacrylate, aminoalkyl methacrylate copolymer, polyacrylic acid, polymethacrylic acid, methacrylic acid alkylamine copolymer, polymethyl methacrylate, polymethacrylic acid anhydride, polymethacrylate, polyacrylamide, polymethacrylic acid anhydride and glycidyl methacrylate copolymers, an alkylcellulose such as ethylcellulose, methylcellulose, calcium carboxymethyl cellulose, certain substituted cellulose polymers such as hydroxypropyl methylcellulose phthalate, and hydroxypropyl methylcellulose acetate succinate, cellulose acetate butyrate, cellulose acetate phthalate, and cellulose acetate trimaleate, polyvinyl acetate phthalate, polyester, waxes, shellac, zein and the like.

Eudragits are well known polymers and copolymers useful for controlled release applications. The EUDRAGIT® grades for enteric coatings are based on anionic polymers of methacrylic acid and methacrylates. They contain —COOH as a functional group. They dissolve at ranges from pH 5.5 to pH 7. EUDRAGIT® FS 30 D is the aqueous dispersion of an anionic copolymer based on methyl acrylate, methyl methacrylate and methacrylic acid. It is insoluble in acidic media, but dissolves by salt formation above pH 7.0. EUDRAGIT® L100-55 and L30-55 dissolve at pH above 5.5. EUDRAGIT® L100 and 5100 dissolve at pH above 6.0.

Sustained-release EUDRAGIT® formulations are employed for many oral dosage forms to enable time-controlled release of active ingredients. Drug delivery can be controlled throughout the whole gastrointestinal tract for increased therapeutic effect and patient compliance. Different polymer combinations of EUDRAGIT® RL (readily permeable) and RS (sparingly permeable) grades allow custom-tailored release profiles and enable a wide range of alternatives to achieve the desired drug delivery performance. The EUDRAGIT® NE polymer is a neutral ester dispersion which requires no plasticiser and is particularly suitable for granulation processes in the manufacture of matrix tablets and sustained release coatings.

Exemplary osmagents or osmotic agents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are well known in the art.

As used herein, the term "disintegrant" means a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g. Avicel), carboxymethylcellulose calcium, croscarmellose sodium, alginic acid, sodium alginate, cellulose polyacrilin potassium (e.g. Amberlite™), alginates, sodium starch glycolate, gums, agar, guar, locust bean, karaya, pectin, tragacanth, crospovidone and other materials known to one of ordinary skill in the art.

A superdisintegrant is a rapidly acting disintegrant. Exemplary superdisintegrants include crospovidone and low substituted HPC.

In some embodiments, a plasticiser may also be included in the oral dosage form. Suitable plasticisers include, but are not limited to, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticisers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate.

The delayed or controlled release dosage form may further include one or more functional excipients such as lubricants, thermal lubricants, antioxidants, buffering agents, alkalinising agents, binders, diluents, sweeteners, chelating agents, colorants, flavourants, surfactants, solubilisers, wetting agents, stabilizers, hydrophilic polymers, hydrophobic polymers, waxes, lipophilic materials, absorption enhancers, preservatives, absorbents, cross-linking agents, bioadhesive polymers, retardants, pore formers and fragrance.

Lubricants or thermal lubricants useful in the present invention include, but are not limited to fatty esters, glyceryl monooleate, glyceryl monostearate, wax, carnauba wax, beeswax, vitamin E succinate, and a combination thereof.

As used herein, the term "antioxidant" means an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole (BHA), butylated hydroxytoluene (BHT), hypophophorous acid, monothioglycerol, sodium ascorbate, sodium formaldehyde sulfoxylate and sodium metabisulfite and others known to those of ordinary skill in the art. Other suitable antioxidants include, for example, vitamin C, sodium bisulfite, vitamin E and its derivatives, propyl gallate or a sulfite derivative.

Binders suitable for use in the present invention include beeswax, carnauba wax, cetyl palmitate, glycerol behenate, glyceryl monostearate, glyceryl palmitostearate, glyceryl stearate, hydrogenated castor oil, microcrystalline wax, paraffin wax, stearic acid, stearic alcohol, stearate 6000 WL1644, gelucire 50/13, poloxamer 188, and polyethylene glycol (PEG) 2000, 3000, 6000, 8000, 10000 or 20000.

A buffering agent may be used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art, As used herein, the term "alkalising agent" means a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

Exemplary binders include: polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses and cellulosic derivatives such as low substituted HPC (L-HPC) methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; PLA and PLGA, polyesters (shellac), wax such as carnauba wax, beeswax; polysaccharides such as cellulose, tragacanth, gum arabic, guar gum, and xanthan gum.

Exemplary chelating agents include EDTA and its salts, alphahydroxy acids such as citric acid, polycarboxylic acids, polyamines, derivatives thereof, and others known to those of ordinary skill in the art.

As used herein, the term "colourant" means a compound used to impart colour to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural colouring agents such as grape skin extract, beet red powder, beta carotene, annato, carmine, turmeric, paprika, and other materials known to one of ordinary skill in the art. The amount of colouring agent used will vary as desired.

As used herein, the term "flavourant" means a compound used to impart a pleasant flavour and often odour to a pharmaceutical preparation. Exemplary flavouring agents or flavourants include synthetic flavour oils and flavouring aromatics and/or natural oils, extracts from plants, leaves, flowers, fruits and so forth and combinations thereof.

Suitable surfactants include Polysorbate 80, sorbitan monooleate, polyoxymer, sodium lauryl sulfate or others known in the art. Soaps and synthetic detergents may be employed as surfactants. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof A wetting agent is an agent that decreases the surface tension of a liquid. Wetting agents would include alcohols, glycerin, proteins, peptides water miscible solvents such as glycols, hydrophilic polymers Polysorbate 80, sorbitan monooleate, sodium lauryl sulfate, fatty acid alkali metal, ammonium, and triethanolamine salts, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Solubilisers include cyclodextrins, povidone, combinations thereof, and others known to those skilled in the art.

Exemplary waxes include carnauba wax, beeswax, microcrystalline wax and others known to those skilled in the art.

Exemplary absorption enhancers include dimethyl sulfoxide, Vitamin E PGS, sodium cholate and others known to those skilled in the art.

Preservatives include compounds used to prevent the groweighth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those skilled in the art.

Examples of absorbents include sodium starch glycolate (Explotab™, Primojel™) and croscarmellose sodium (Ac-Di-Sol™), cross-linked PVP (Polyplasdone™ XL 10), veegum, clays, alginates, PVP, alginic acid, carboxymethylcellulose calcium, microcrystalline cellulose (e.g. Avicel), polacrillin potassium (e.g. Amberlite™), sodium alginate, corn starch, potato starch, pregelatinized starch, modified starch, cellulosic agents, montmorrilonite clays (e.g. bentonite), gums, agar, locust bean gum, gum karaya, pectin, tragacanth, and other disintegrants known in to those skilled in the art.

A cross-linking agent is defined as any compound that will form cross-links between the moieties of the polymer. A cross-linking agent can include, by way of example and without limitation, an organic acid, an alpha-hydroxy acid, and a beta-hydroxy acid. Suitable cross-linking agents include tartaric acid, citric acid, fumaric acid, succinic acid and others known to those skilled in the art.

Bioadhesive polymers include polyethylene oxide, Klucel® (hydroxypropyl cellulose), CARBOPOL, polycarbophil, GANTREZ, Poloxamer, and combinations thereof, and others known to those skilled in the art.

Retardants are agents that are insoluble or slightly soluble polymers with a glass transition temperature (Tg) above 45° C., or above 50° C. before being plasticized by other agents in the formulation including other polymers and other excipients needed for processing. The excipients include waxes, acrylics, cellulosics, lipids, proteins, glycols, and the like.

Exemplary pore formers include water-soluble polymers such as polyethylene glycol, propylene glycol, poloxamer and povidone; binders such as lactose, calcium sulfate, calcium phosphate and the like; salts such as sodium chloride, magnesium chloride and the like; combinations thereof and other similar or equivalent materials which are widely known in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those skilled in the art.

Compounds used in the art of pharmaceutical formulation generally serve a variety of functions or purposes. Thus, if a compound named herein is mentioned only once or is used to define more than one term herein, its purpose or function should not be construed as being limited solely to that or those named purpose(s) or function(s).

The delayed or controlled release dosage form may provide release corresponding profiles in vitro and when orally administered to a human subject.

In some embodiments, after oral administration, the dosage form may suitably provide a lag time of between 6-10 hours, with a low level of drug absorption, followed by an increased plasma concentration of the one or more n-3 DPA-derived resolvins over the following 3 to 6 hours, with the highest rate of increase in the first few hours after the lag.

In vitro dissolution profiles can be obtained in conditions that are designed to mimic the gastric environment or an environment that is encountered by an oral composition that is swallowed by a human. Although residence time in the stomach varies, a typical test should place the dosage form in a low pH solution of 0.1N HCl for two hours to mimic residence time in stomach acid. The dosage form should then be placed in a higher pH aqueous solution, about pH 6 for 2-6 hours followed by typically pH 6.8 to mimic the environment of the ileum and colon. Such dissolution conditions are defined herein as "simulated gastric conditions" even though they encompass both the acidic first stage and the subsequent higher pH stages of a normal human gastro-intestinal tract.

Following the delay period after oral administration, the plasma concentration of the one or more n-3 DPA-derived resolvins may increase over approximately 3-6 hours to a reach a maximum plasma concentration (Cmax). Based on this absorbance profile, a dose taken at 9:00 PM with a 6-hour delay may begin to release the one or more n-3 DPA-derived resolvins at about 3 AM with a maximum plasma concentration at about 9 to 12 hours after administration.

It will be understood that in some embodiments, the one or more n-3 DPA-derived resolvins may be released slowly during the lag time. Some examples of small amounts of drug absorbance during the lag time as compared to total drug exposure from a single dose are those in which from 1 to 2% wt., or from 1 to 5% wt., and in which no more than about 10% wt. of the total drug is adsorbed during a 6-10-hour lag-time. It will also be understood that a greater percentage, e.g. 12%, 15%, 18% or even 20% wt., may be released as the delayed release layer becomes more permeable.

The delayed or controlled release dosage form may suitably be adapted for once daily administration of the one of more n-3 DPA-derived resolvins for the treatment or prevention of cardiovascular disease, as described above.

The dosage form may be formulated to be taken prior to going bed and starts to release after a lag of several hours so the subject has absorbed a sufficient amount of drug to have a therapeutic effect while awakening in the early hours of the morning.

In one embodiment, the dosage form may include a capsule enclosing a single population of beads or minitablets that include a core and two or more coatings surrounding the core. An inner core is a bead or minitablet containing one or more n-3 DPA-derived resolvins for use in accordance with the invention and one or more excipients. The core may be enclosed in a sustained release layer and an outer, delayed release layer.

The sustained release layer may include a combination of water-soluble polymers and water-insoluble polymers. The sustained release coating may contain a combination of polyethylene oxide and an ethylcellulose, for example, or a hydroxypropylmethyl cellulose and ethylcellulose. A suitable ethylcellulose product that can be used in the disclosed dosage forms is ETHOCEL™, marketed under a trade mark of The Dow Chemical Company. The rate of dissolution of the sustained release layer may be controlled by adjusting the ratio of water-soluble polymer to water-insoluble polymer in the coating or layer. The weight ratio of water-insoluble to water-soluble polymers may be adjusted, for example and without limitation, from 90:10 to 10:90, from 80:20 to 20:80, from 75:25 to 25:75, from 70:30 to 30:70, from 67.5:33.5 to 33.5:67.5 from 60:40 to 40:60, from 56:44 to 44:56, or to 50:50.

The sustained release coating may also contain plasticizers such as triethyl citrate (TEC) at levels of from 3% to 50% of the combined weight of the polymers. Other additives to the coating may include titanium dioxide, talc, colloidal silicone dioxide or citric acid.

Some examples of sustained release layers are shown in following Table 1. The various formulations include those in which the ratios of water-insoluble to water-soluble polymers are varied and one in which the ratios are reversed. Citric acid was added to a formula to keep the micro environment pH in the film low to inhibit the dissolution of HPMCAS-LF, which dissolves at ≥pH5.5 thus creating a lag at the beginning of the dissolution curve. In certain embodiments, the one or more n-3 DPA-derived resolvins may be included in the sustained release layer.

TABLE 1

Exemplary Sustained Release Layers

| Component | A (% w/w) | B (% w/w) | C (% w/w) | D (% w/w) | E (% w/w) | F (% w/w) |
|---|---|---|---|---|---|---|
| ETHOCEL ™ | 51.0 | 34.9 | 34.5 | 34.4 | 60.2 | 36.1 |
| $RvD_{n-3\ DPA}$ | | | | 47.2 | | |
| PEO | | | | | 36.1 | 60.2 |
| HPMC E5 P | 17.0 | 13.1 | | | | |
| HPMCAS-LF | | | 27.6 | 11.5 | | |
| Talc | 3.6 | 2.8 | 3.6 | 2.4 | | |
| Titanium Dioxide | 24.0 | 18.5 | 24.0 | | | |
| Citric acid | | | 6.9 | | | |
| Colloidal silicon dioxide | 0.4 | | | | | |
| TEC | 4.0 | 26.2 | 3.4 | 4.6 | 3.6 | 3.6 |
| Totals* | 100.0 | 100.0 | 100.0 | 100.0 | 100.0 | 100.0 |

*Figures may not sum to 100, due to rounding

An exemplary core is shown in Table 2 below. In this example, an osmotic agent is added to the core.

TABLE 2

| Component | Pellet Core (% w/w) |
|---|---|
| $RVD_{n-3\ DPA}$ | 20.0 |
| Avicel PH101 | 47.0 |
| Potassium chloride | 30.0 |
| Klucel ® EF | 3.0 |
| Totals | 100.0 |

In some embodiments, a drug-containing core bead or minitablet may be coated with a delayed release layer that includes one or more water-insoluble polymers, one or more water-soluble polymers and a silicone oil to achieve a desired delay or lag time prior to release as in the present disclosure. Lag time and release may be controlled by the proportion of the two types of polymers and the thickness of the layer. In such embodiments, the delayed release layer may include, but is not limited to cellulose acetate phthalate, cellulose acetate trimaletate, hydroxyl propyl methylcellulose phthalate, polyvinyl acetate phthalate, acrylic polymers, polyvinyl acetaldiethylamino acetate, hydroxypropyl methylcellulose acetate succinate, cellulose acetate trimellitate, shellac, methacrylic acid copolymers, EUDRAGIT® L30D, EUDRAGIT® L100, EUDRAGIT® FS30D, EUDRAGIT® 5100 or combinations of any thereof. The delayed release layer may also include a plasticiser, or in some embodiments the delayed release layer cmayan include methacrylic acid copolymer Type B, mono- and diglycerides, dibutyl sebacate and polysorbate 80. The delayed release layer may also include a cellulose ether derivative, an acrylic resin, a copolymer of acrylic acid and methacrylic acid esters with quaternary ammonium groups, a copolymer of acrylic acid and methacrylic acid esters or a combination of any thereof. The layer may further include a powder component such as talc as a carrier for the silicone oil.

In some embodiments of the invention, one or more n-3 DPA-derived resolvins may be contained in a delayed and/or controlled release capsule. In such embodiments, a water-insoluble capsule may contain one or more compartments in which the active agent is held. Additionally, one or more absorbents, superabsorbents or osmagents may be included in the drug containing compartments. The capsules may also include one more apertures plugged with a water-soluble polymer, at least one in fluid communication with each compartment and a delayed release layer enclosing the entire capsule.

In such embodiments, the length of initial delay may be controlled by the composition and thickness of the outer, delayed release layer. This layer can be a pH dependent layer or a pH independent layer as disclosed herein. When the capsule is administered to a human, the delayed release layer begins to lose integrity as the capsule passes through the GI tract. When the water-soluble plugs are exposed and dissolve, aqueous fluid enters the drug containing compartment(s) and is absorbed by the absorbent or osmagent, thus driving the active agent from the capsule through the aperture. The release profile can be controlled by the concentration and absorption characteristics of the absorbent or osmagent to obtain the desired profile.

As disclosed in the Examples below, lipid mediator (LM) profiling of plasma from healthy volunteers demonstrated a significant increase in n-3 DPA-derived resolvins between 7 AM and 9 AM. At these time intervals, increases in the expression of monocyte, platelet and neutrophil activation markers were found in healthy volunteer peripheral blood. Further, patients with cardiovascular disease demonstrated reduced plasma n-3 DPA-derived resolvin levels, a loss in diurnal regulation of these molecules and increases in the activation of circulating platelets, neutrophils and monocytes. In addition, lipid mediator profiling of plasma from patients at risk of myocardial infarct were seen to demonstrate reductions in $RvD_{n-3}DPA$ that was associated with decreased 5-lipoxyenase and 15-lipoxygenase expression and increased systemic adenosine concentrations.

In accordance with the present invention, therefore, cardiovascular disease may be diagnosed by measuring the levels of one or more n-3 DPA-derived resolvins in a subject's blood in the early hours of the morning and/or by monitoring systemic adenosine activity or expression levels and/or by monitoring 5-LOX or 15-LOX activity or expression levels. In some embodiments, the subject's early-morning plasma levels may be compared with corresponding plasma levels found in healthy patients at about the same time of day. A reduced level of n-3 DPA-derived resolvins in the subject's blood in the early hours of the morning as compared with healthy subjects may be indicative of cardiovascular disease or a risk of cardiovascular disease. Correspondingly, an increased level of adenosine expression or activity levels, and/or a reduced level of 5-LOX or 15-LOX activity or expression levels, may be indicative of cardiovascular disease or a risk of cardiovascular disease.

Alternatively, in some embodiments, the early-morning levels of the one or more n-3 DPA-derived resolvins or adenosine or 5-LOX/15-LOX activity or expression levels may be compared with corresponding levels of the one or more n-3 DPA-derived resolvins or adenosine or 5-LOX/15-LOX activity or expression levels in the same subject's blood at another time of day, for example in the evening. Suitably, the levels of the one or more n-3 DPA-derived resolvins or adenosine or 5-LOX/15-LOX activity or expression levels in the early-morning may be compared with the levels of the one or more n-3 DPA-derived resolvins or adenosine or 5-LOX/15-LOX activity or expression levels in the subject's blood in the evening the night before or immediately after the early-morning. In a further alternative, the early-morning levels of the n-3 DPA-derived resolvins or adenosine or 5-LOX/15-LOX activity or expression levels in the subject's blood may be compared with the subject's peak plasma levels of n-3 DPA-derived resolvin or adenosine or 5-LOX/15-LOX activity or expression levels during the day.

The difference between the levels of the one or more n-3 DPA-derived resolvins or adenosine or 5-LOX/15-LOX activity or expression levels in the early-morning and the corresponding levels measured at another time of day may be indicative of the cardiovascular health of the subject, as described in more detail below. In general, the smaller the difference between the levels measured at the different times of day, the greater the subject's risk of cardiovascular disease.

In a similar manner, a subject's risk of suffering myocardial infarction or another acute cardiac event as a result of cardiovascular disease may be assessed by evaluating their early-morning levels of one or more n-3 DPA-derived resolvins or adenosine or 5-LOX/15-LOX activity or expression levels and, optionally, comparing such early-morning levels with corresponding levels in healthy patients at about the same time of day, or levels obtained from the same subject at another time during the day, or with minimum daytime n-3 DPA-derived resolvin levels or adenosine or 5-LOX/15-LOX activity or expression levels.

In a different aspect of the present invention, therefore, there is provided a method of diagnosing or assessing the risk of cardiovascular disease in a subject which comprises comparing the levels of one or more n-3 DPA-derived resolvins or adenosine or 5-LOX/15-LOX activity or expression levels in a first biological sample obtained from the subject's blood in the early morning with corresponding levels of the one or more n-3 DPA-derived resolvins or adenosine or 5-LOX/15-LOX activity or expression levels in a second biological sample obtained from the subject's blood at another time of day.

In some embodiments, the levels of two or more n-3 DPA-derived resolvins may be measured.

Suitably, the one or more n-3 DPA-derived resolvins may include one or more, e.g. one, two or three, of $RvD1_{n-3\ DPA}$, $RvD2_{n-3\ DPA}$ and $RvD5_{n-3\ DPA}$.

In some embodiments, the levels of one, two or all three of $RvD1_{n-3\ DPA}$, $RvD2_{n-3\ DPA}$ and/or $RvD5_{n-3\ DPA}$ in the biological samples may be measured to obtain the n-3 DPA-derived resolvin levels.

As described above in relation to the therapeutic aspects of the present invention, by "early hours of the morning" herein is meant between 7 AM and 9 AM or, more broadly, between 6 AM and 10 AM. Suitably the first biological sample of the subject's blood may be obtained at around 8 AM or 8:30 AM.

The second biological sample of the subject's blood may be obtained at any other time of day, but is conveniently obtained in the afternoon or evening when the levels of lipid mediators in the subject's blood are normally lower because of circadian fluctuations. Thus, the second biological sample may be obtained, in some embodiments, between midday and about 9 PM, conveniently between 4-8 PM.

As an alternative, biological samples of the subject's blood may be taken at regular intervals throughout the day, and the levels of n-3 DPA-derived resolvins or adenosine or 5-LOX/15-LOX activity or expression levels measured in the early hours of the morning as described above compared with the minimum levels of the n-3 DPA-derived resolvins or adenosine or 5-LOX/15-LOX activity or expression levels as measured throughout the day. Such embodiments of the invention may be convenient for use in clinical studies in which subjects are enrolled and checked into a clinical trial site, where blood samples can easily be taken at regular intervals throughout the day.

In accordance with the invention, the levels of the one or more n-3 DPA-derived resolvins or adenosine or 5-LOX/15-LOX activity or expression levels in the first early-morning sample may be compared with the corresponding levels of the one or more n-3 DPA-derived resolvins or adenosine or 5-LOX/15-LOX activity or expression levels in the second sample, or the minimum levels as described above, and the difference between the levels may be indicative of cardiovascular disease or a risk of cardiovascular disease.

In a healthy subject, who is not suffering from cardiovascular disease as described below, the levels of the n-3 DPA-derived resolvins in the subject's blood may naturally vary in the range 5-15 pg/mL during the day, with a maximum in the early hours of the morning. If the difference between the early hours levels of n-3 DPA-derived resolvins and the corresponding levels at other times of day or minimum levels is less than about 5 pg/mL, this may be indicative of cardiovascular disease or a risk of the subject suffering myocardial infarction or another acute cardiovascular event.

In yet another aspect of the present invention, there is provided a method of diagnosing or assessing the risk of cardiovascular disease in a subject which comprises comparing the levels of one or more n-3 DPA-derived resolvins or adenosine or 5-LOX/15-LOX activity or expression levels in a biological sample obtained from the subject's blood in the early morning with reference levels for the one or more n-3 DPA-derived resolvins or adenosine or 5-LOX/15-LOX activity or expression levels that are typically found in healthy subjects.

Reference levels for one or more n-3 DPA-derived resolvins or adenosine or 5-LOX/15-LOX activity or expression levels in the early-morning in healthy subjects may be obtained by taking blood samples from one or more healthy subjects in the early hours of the morning and measuring the plasma concentration of the one or more n-3 DPA-derived resolvins or adenosine or 5-LOX/15-LOX activity or expression levels. Since the levels of the one or more n-3 DPA-derived resolvins or adenosine or 5-LOX/15-LOX activity or expression levels are likely to vary naturally from one subject to another and with time of day, it is desirable to measure the plasma concentration of the one or more n-3 DPA-derived resolvins or adenosine or 5-LOX/15-LOX activity or expression levels in a plurality of different healthy subjects and to take an average concentration level. Blood samples from the healthy subjects should be taken at or approximately the same time of day.

By a "healthy" subject herein, is meant a subject who does not have cardiovascular disease. A "healthy" subject does not have severe coronary artery disease, has had no percutaneous coronary intervention and has no more than one of the following risk factors, namely hypertension, high cholesterol, smoker, diabetes or no ischaemic heart disease. "Healthy" as used herein in relation to a subject does not mean the subject does not suffer from any disease, only that they are not suffering from a relevant cardiovascular disease as described above.

In some embodiments, reference plasma levels for the one or more n-3 DPA-derived resolvins or adenosine or 5-LOX/15-LOX activity or expression levels may be obtained for different genders, ethnicities and/or ages of subjects with a view to ensuring the reference levels are properly comparable with the levels of n-3 DPA-derived resolvins or adenosine or 5-LOX/15-LOX activity or expression levels measured in the biological sample obtained from the subject.

As before, the levels of two or more n-3 DPA-derived resolvins in the sample may be measured.

In some embodiments, the one or more n-3 DPA-derived resolvins may include n-3 DPA-derived resolvins selected from $RvD1_{n\text{-}3\ DPA}$, $RvD2_{n\text{-}3\ DPA}$ and $RvD5_{n\text{-}3\ DPA}$.

In some embodiments, the levels of one, two or all three of $RvD1_{n\text{-}3\ DPA}$, $RvD2_{n\text{-}3\ DPA}$ and/or $RvD5_{n\text{-}3\ DPA}$ in the biological sample may be measured to obtain the n-3 DPA-derived resolvin levels.

By way of illustration, the reference level for n-3 DPA derived resolvins in the blood of a healthy subject early in the morning may be in the range of about 10 pg/mL to about 25 pg/mL, typically about 15 pg/mL. An early morning level of n-3 DPA derived resolvins of less than about 10 pg/mL, especially less than about 5 pg/mL, in the biological sample may be indicative of cardiovascular disease or a risk of cardiovascular disease.

Suitably, the biological sample(s) may be whole blood, serum or plasma samples.

Suitably the biological sample(s) may be treated immediately after collection with an anticoagulant such, for example, as heparin to prevent clotting.

If the samples are required to be stored prior to analysis, in some embodiments, they may be placed in an organic solvent and stored at a temperature of −75° C. or below. Suitably, the organic solvent may comprise or consist of methanol. Although lipid mediators have been found to be unstable in frozen samples during the term-long-term storage, with the levels of some of the mediators being significantly (>50%) reduced following three-month storage, it has been surprisingly found that by using methanol, and optionally other organic solvents, the stability of these molecules may be improved when they are stored at temperatures of −75° C. and below. Suitably, the samples may be stored at temperatures of about −80° C.

Deuterium labelled standards of the kind described below may be added to the samples prior to freezing.

Methods for measuring the levels of n-3 DPA-derived resolvins or adenosine or 5-LOX/15-LOX activity or expression levels in biological samples such as blood are available to those skilled in the art and need not be described herein in detail.

Suitable methods are disclosed, for example, in Yang R et al. Metabolomics-Lipidomics of Eicosanoids and Docosanoids Generated by Phagocytes. *Curr Protoc Immunol.* 2000; 95:14.26:14.26.1-14.26.26 and Dalli J and Serhan C N. Specific lipid mediator signatures of human phagocytes: microparticles stimulate macrophage efferocytosis and pro-resolving mediators. *Blood.* 2012; 120:e60-e72, the contents of both of which are incorporated herein by reference.

Briefly, in some embodiments, the levels of the one or more n-3 DPA-derived resolvins in the samples may be measured using liquid chromatography tandem mass spectrometry (LC-MS/MS) after extracting the SPM from the samples.

The SPM may be extracted from the samples using solid-phase extraction, for instance using C18 columns. Suitable methods are disclosed by Colas R A et al. Identification and signature profiles for pro-resolving and inflammatory lipid mediators in human tissue. *Am J Physiol Cell Physiol.* 2014; 307:C39-54, the contents of which are incorporated herein by reference.

One or more internal labelled standards may be added to the samples prior to extraction of the SPM to facilitate quantitation of the n-3 DPA-derived resolvins in the samples. Suitable labelled standards are deuterium-labelled 5S-HETE (55-HETE-$d_8$), deuterium-labelled leukotriene B4 ($LTB_4$-$d_4$), deuterium-labelled lipoxin $A_4$ ($LXA_4$-$d_5$), deuterium-labelled resolvin D2 (RvD2-$d_5$) and deuterium-labelled prostaglandin $E_2$ ($PGE_2$-$d_4$).

The identity of an n-3 DPA-derived resolvin in a sample may be confirmed by matching its retention time (RT) and at least six diagnostic ions from its MS-MS spectrum with those of a synthetic or authentic standard for the SPM. Retention times for molecules measured using liquid chromatography are often instrument specific and will vary between different systems based on column chemistry, chromatographic gradients and sample quality. The retention times for each system may be established empirically, for example using both labelled standards (e.g. deuterium labelled standards) and standards for the molecules of interest.

By way of example, in some embodiments, the retention times of the above-mentioned n-3 DPA-derived resolvins may be as shown in Table 3 below:

TABLE 3

| D-series resolvin ($RvD_{n\text{-}3\ DPA}$) | Retention time ($R_T$) |
|---|---|
| $RvD1_{n\text{-}3\ DPA}$ | 11.4 min |
| $RvD2_{n\text{-}3\ DPA}$ | 10.8 min |
| $RvD5_{n\text{-}3\ DPA}$ | 13.6 min |

Quantitation may be achieved using linear regression curves that are constructed using a synthetic or authentic standard for the mediator.

LC-MS/MS may be suitable for use in situations where there is access to the equipment required such, for example, in hospital laboratories. However, more conveniently, the levels of the one or more n-3 DPA-derived resolvins in the samples may be measured using an immunoassay. Immunoassays have the potential to be miniaturised to run on a microfluidics device or test-strip and may be more suited for clinical point-of-care applications. Embodiments of the invention which incorporate an immunoassay may therefore be used in situ by a primary healthcare provider for assistance in diagnosing cardiovascular disease in an individual patient.

The levels of the one or more n-3 DPA-derived resolvins may be measured using a homogeneous or heterogeneous immunoassay.

Thus, in some embodiments, the levels of the or each n-3 DPA-derived resolvin may be measured in solution by binding to labelled antibodies that are present in excess, whereby binding alters detectable properties of the label. The amount of a specific SPM present will therefore affect the amount of the label with a particular detectable property. As is well known in the art, the label may comprise a radioactive label, a fluorescent label or an enzyme having a chromogenic or chemiluminescent substrate that is coloured or caused or allowed to fluoresce when acted on by the enzyme.

The antibodies may be polyclonal or monoclonal with specificity for the n-3 DPA-derived resolvin. In some embodiments, monoclonal antibodies may be used.

Alternatively, a heterogeneous format may be used in which the one or more n-3 DPA-derived resolvins are captured by surface-bound antibodies for separation and quantification. In some embodiments, a sandwich assay may be used in which a surface-bound n-3 DPA-derived resolvin is quantified by binding a labelled secondary antibody.

Suitably, the immunoassay may comprise an enzyme immunoassay (EIA) in which the label is an enzyme such, for example, as horseradish peroxidase (HRP). Suitable substrates for HRP are well known in the art and include, for example, ABTS, OPD, AmplexRed, DAB, AEC, TMB, homovanillic acid and luminol. In some embodiments, an ELISA immunoassay may be used; a sandwich ELISA assay may be particularly preferred.

The immunoassay may be competitive or non-competitive. Thus, in some embodiments, the amounts of the one or more n-3 DPA-derived resolvins may be measured directly by a homogeneous or heterogeneous method, as described above. Alternatively, the n-3 DPA-derived resolvins in the samples may be sequestered in solution with a known amount of antibody which is present in excess, and the amount of antibody remaining then determined by binding to surface-bound SPM to give an indirect read-out of the amount of n-3 DPA-derived resolvins in the original sample. In another variant, the one or more n-3 DPA-derived resolvins may be caused to compete for binding to a surface bound antibody with a known amount of a labelled SPM.

The surface bound antibodies or SPM may be immobilised on any suitable surface of the kind known in the art. For instance, the antibodies or SPM may be immobilised on a surface of a well or plate or on the surface of a plurality of magnetic or non-magnetic beads.

In yet another aspect of the present invention therefore there is provided an immunoassay for measuring the level of an n-3 DPA-derived resolvin in a biological sample, the immunoassay comprising antibodies to the n-3 DPA-derived resolvin that are coated on a surface for capturing the n-3 DPA-derived resolvin in the sample and/or tagged with a label that is altered in a detectable manner by binding to the n-3 DPA-derived resolvin in the sample, or an amount of the n-3 DPA-derived resolvin, which is the same as the one to be quantitated in the sample, that is immobilised on a surface for capturing antibodies to the n-3 DPA-derived resolvin after mixing with the sample.

In some embodiments, the immunoassay may be a competitive assay, further comprising a known amount of the n-3 DPA-derived resolvin, which is the same as the one to be quantitated in the sample, but tagged with a detectable label. The labelled n-3 DPA-derived resolvin may be affinity-bound to a suitable surface by an antibody to the n-3

DPA-derived resolvin. Upon adding the sample, a proportion of the labelled n-3 DPA-derived resolvin may be displaced from the surface-bound antibodies, thereby providing a measure of the level of n-3 DPA-derived resolvin in the sample.

In some embodiments, the immunoassay may comprise a surface-bound n-3 DPA-derived resolvin, which is the same as the n-3 DPA-derived resolvin that is to be quantitated in the sample, and a known amount of antibodies to the n-3 DPA-derived resolvin in solution in excess. The sample is first mixed with the antibodies in solution such that a proportion of the antibodies bind with the n-3 DPA-derived resolvin in the sample. The amount of unbound antibodies remaining can then be measured by binding to the surface-bound n-3 DPA-derived resolvin.

In some embodiments, the immunoassay may comprise a labelled secondary antibody to the n-3 DPA-derived resolvin or to a primary antibody to the n-3 DPA-derived resolvin for quantifying the amount of the n-3 DPA-derived resolvin bound to surface-bound antibodies or the amount of primary antibody bound to the n-3 DPA-derived resolvin immobilised on a surface.

In a still another aspect of the present invention, there is provided equipment for measuring the level of a specific n-3 DPA-derived resolvin in a sample comprising a sample collection device and an immunoassay in accordance with the invention.

Suitably, the equipment may further comprise a detector for detecting labelled n-3 DPA-derived resolvin or labelled antibodies to the n-3 DPA-derived resolvin in the immunoassay. Suitable labels are mentioned above, but in a preferred embodiment, the label may be an enzyme having a chromogenic or chemiluminescent substrate that is coloured or caused or allowed to fluoresce when acted on by the enzyme.

In some embodiments, the immunoassay or equipment of the invention may be incorporated into a miniaturised device for measuring the levels of one or more n-3 DPA-derived resolvins in a biological sample. Suitably, the device may comprise a "lab-on-a-chip".

In accordance with still another aspect of the invention therefore, there is provided a device for measuring the level of one or more n-3 DPA-derived resolvins in a biological sample obtained from a subject, the device comprising one or more parts defining an internal channel having an inlet port and a reaction zone, in which an n-3 DPA-derived resolvin in a sample may be reacted with an immobilised primary antibody for the n-3 DPA-derived resolvin for capturing the n-3 DPA-derived resolvin, or a primary antibody for the n-3 DPA-derived resolvin in excess in solution after mixing with the sample upstream of the reaction zone may be reacted with n-3 DPA-derived resolvin, which is the same as the one to be measured in the sample, but immobilised on a surface within the reaction zone, for quantifying directly or indirectly the amount of the n-3 DPA-derived resolvin in the sample.

The captured n-3 DPA-derived resolvin or primary antibody may then be detected using a secondary antibody to the n-3 DPA-derived resolvin or primary antibody, which is tagged with an enzyme.

As described above, the enzyme may have a chromogenic or chemiluminescent substrate that is coloured or caused or allowed to fluoresce when acted on by the enzyme. Suitably, the one or more parts of the device defining the channel, at least adjacent the reaction zone, may be transparent to light, at least in a range of wavelengths encompassing the colour or fluorescence of the substrate to allow detection of a reaction between the n-3 DPA-derived resolvin or primary antibody and the secondary antibody using a suitable detector such, for example, as a photodiode, positioned outside the channel or further channel.

In some embodiments, the device may comprise a plurality of channels, each with its own inlet port, for measuring the levels of a plurality of different n-3 DPA-derived resolvins in the sample in parallel, for example two or more of $RvD1_{n\text{-}3\ DPA}$, $RvD2_{n\text{-}3\ DPA}$ and $RvD5_{n\text{-}3\ DPA}$. Therefore, each channel may include a different respective immobilised primary antibody or n-3 DPA-derived resolvin.

Suitably, the device may comprise one or more selectively operable valves associated with the one or more inlet ports for controlling the admission of a sequence of different reagents into to the channels such, for example, as the sample, wash solutions, primary antibody, secondary antibody and enzyme substrate.

The device therefore may comprise a microfluidics device. The channel may include a reaction zone. Microfluidics devices are known to those skilled in the art. A review of microfluidic immunoassays or protein diagnostic chip microarrays is provided by Chin et al. *Lab on a Chip.* 2012; 12:2118-2134. A microfluidics device suitable for carrying out an ELISA immunoassay at a point-of-care is disclosed by Chan C D et al. Microfluidics-based diagnostics of infectious diseases in the developing world. *Nature Medicine.* 2011; 17(8):1015-1019, the contents of which are incorporated herein by reference.

The methods of assessing or diagnosing cardiovascular disease in accordance with the present invention may be supplemented by assessing changes in activation of white blood cells and/or platelets in the subject's blood. Increased activation of white blood cells, or increased formation of leukocyte-platelet aggregates, in the early hours of the morning may be associated with an increased risk of cardiovascular disease or myocardial infarction.

In some embodiments, therefore, the methods of assessing or diagnosing cardiovascular disease of the invention may further comprise measuring the level of leukocyte and/or platelet activation in the subject's blood in the early hours of the morning, typically between 7 AM and 9 AM.

Suitably, the activation of leucocytes and/or platelets may be assessed by measuring expression activation markers on peripheral blood cells. Suitable markers known to those skilled in the art include CD11b, CD41, CD63 and CD62P.

Methods for quantitating expression levels of activation markers such as CD11b, CD41, CD63 and CD62P are well known to those skilled in the art. In some embodiments, flow cytometry may be used.

Suitable anti-human antibodies for use in flow cytometry include VioBlue-anti-CD41, PE-Cy5-anti-CD62P, Brilliant Violet 711-anti-CD11b, APC-Cy7-anti-CD16, PerCP/Cy5.5-anti-CD63, FITC-ant-CD42b and Alexa Fluor 647-anti-CD14.

In some embodiments, the methods of assessing or diagnosing cardiovascular disease according to the invention may further comprise assessing the ratio of n-3 DPA-derived resolvins to inflammation-initiating eicosanoids in the subject's blood. Inflammation-initiating eicosanoids include prostaglandins (e.g. $PGD_2$, $PGE_2$ and $PGF_{2\alpha}$), leukotriene $B_4$ and/or $TxA_2$.

Suitable methods for quantitating the levels of such inflammation-initiating eicosanoids in the biological sample are available to those skilled in the art and need not be described herein in detail.

A decrease in the ratio of the level of the one or more n-3 DPA-derived resolvins to the level of one or more inflammation-initiating eicosanoids in the subject's blood in the early hours of the morning as compared with a corresponding ratio in a healthy subject measured at the same time of day may support a diagnosis of cardiovascular disease or increased risk of cardiovascular disease.

By way of illustration, the ratio of n-3 DPA-derived resolvins $RvD1_{n\text{-}3\ DPA}$, $RvD2_{n\text{-}3\ DPA}$ and $RvD5_{n\text{-}3\ DPA}$ to prostaglandins $PGD_2$, $PGE_2$ and $PGF_{2\alpha}$, and $LTB_4$ in a healthy subject in the early hours of the morning may be about 0.50, while in a subject with cardiovascular disease, the corresponding ratio may be about 0.13.

The above-described methods, immunoassays or equipment apparatus for measuring the levels of one or more n-3 DPA-derived resolvins or adenosine or 5-LOX/15-LOX activity or expression levels in a subject's blood may also be used, in accordance with still further aspect of the invention for assessing the efficacy of a therapeutic or preventative treatment for cardiovascular disease in one or more subjects. Such methods are applicable to individual subjects as well as groups of subjects such, for example, as a cohort of volunteers in a clinical trial.

In accordance with still another aspect of the present invention therefore there is provided a method of assessing the efficacy of a therapeutic or preventative treatment for cardiovascular disease in one or more subjects, which comprises assessing the levels of one or more n-3 DPA-derived resolvins or adenosine or 5-LOX/15-LOX activity or expression levels in blood samples obtained from the subjects after commencing the treatment, wherein the blood samples are obtained early in the morning and an increase in the levels of the one or more n-3 DPA-derived resolvins and/or a decrease in the activity or expression of adenosine and/or an increase in the expression or activity of 5-LOX or 15-LOX in the samples associated with the treatment is indicative of efficacy of the treatment.

The methods, immunoassays or equipment of the present invention may be used for assessing the efficacy of therapeutic treatments for cardiovascular disease in a subject, including coronary artery disease, vascular inflammation and other cardiovascular disorders that may be caused or exacerbated by dysfunction of the body's natural regulatory system for controlling levels of pro-inflammatory mediators such, for example, as pro-inflammatory eicosanoids, especially in the early morning. The methods, immunoassays or equipment of the invention may also be used for assessing the efficacy of preventative treatments for cardiovascular disease, particularly myocardial infarction, stroke, heart failure and angina.

The therapeutic or preventative treatment may comprise administration of a medicament. Whilst the methods of the present invention for assessing the efficacy of a preventative or therapeutic treatment for cardiovascular disease are not limited to any particular treatment or medicament, in some embodiments, the methods of the invention may be used for assessing the efficacy of one or more drugs selected from statins (e.g. simvastatin, fluvastatin, atorvastatin, rosuvastatin, pravastatin, lovastatin), fibrates (e.g. gemfibrozil, fenofibrate, clofibrate, bezafibrate, ciprofibrate, clinofibrate, clofibride, ronifibrate and simfibrate), calcium channel blockers (e.g. amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine and pranidipine) or combinations of these such, for example, as a combination of a statin and calcium channel blocker.

In some embodiments, the therapeutic or preventative treatment may comprise an investigative medical product (IMP), particularly in the context of a clinical trial. Such a clinical trial should be conducted with suitable controls (e.g. some subjects receiving placebo or another treatment) and may be blind or double-blind.

In some embodiments, the therapeutic or preventative treatment may consist of administration of a combination of medicaments, or a new dosage regimen of investigative or approved medicinal products for cardiovascular disease.

Suitably, the levels of the one or more n-3 DPA-derived resolvins or adenosine or 5-LOX/15-LOX activity or expression levels may be compared with corresponding levels of the one or more n-3 DPA-derived resolvins or adenosine or 5-LOX/15-LOX activity or expression levels in blood samples obtained from the one or more subjects prior to commencement of treatment or with blood samples obtained from one or more subjects receiving placebo or another treatment.

In some embodiments, the levels of the one or more n-3 DPA-derived resolvins or adenosine or 5-LOX/15-LOX activity or expression levels may be monitored in a series of two or more samples obtained from the or each of the subjects at timed intervals after initiating the treatment.

In some embodiments, the levels of the one or more n-3 DPA-derived resolvins or adenosine or 5-LOX/15-LOX activity or expression levels in blood samples obtained from the one or more subjects early in the morning may be compared with corresponding levels of the one or more n-3 DPA-derived resolvins or adenosine or 5-LOX/15-LOX activity or expression levels in blood samples obtained from the subjects at another time of day; wherein an increase in the difference between the levels of the one or more n-3 DPA-derived resolvins and/or a decrease in the expression or activity of adenosine and/or an increase in the expression or activity or 5-LOX or 15-LOX in the blood samples obtained in the early morning and at the other time of day is indicative of efficacy of the treatment.

As described above, the one or more n-3 DPA-derived resolvins may comprise one or more of $RvD1_{n\text{-}3\ DPA}$, $RvD2_{n\text{-}3\ DPA}$ and/or $RvD5_{n\text{-}3\ DPA}$.

As before, by "early hours of the morning" herein is meant generally between about 6 AM and 10 AM or, more particularly, between about 7 AM and 9 AM.

Where the levels of the one or more n-3 DPA-derived resolvins or adenosine or 5-LOX/15-LOX activity or expression levels as measured in the early hours of the morning are compared with corresponding levels measured at another time of day, the early-morning levels of the one or more n-3 DPA-derived resolvins or adenosine or 5-LOX/15-LOX activity or expression levels may be compared with corresponding levels measured in the afternoon or evening immediately before or after the early-morning measurement, for example between about 4 PM and 10 PM or, more particularly, between about 6 PM and 8 PM.

As before, in an alternative embodiment, the levels of the one or more n-3 DPA-derived resolvins or adenosine or 5-LOX/15-LOX activity or expression levels as measured in the early hours of the morning may be compared with the minimum levels of the one or more n-3 DPA-derived resolvins or adenosine or 5-LOX/15-LOX activity or expression levels during the rest of the day; for example, the minimum levels of the one or more n-3 DPA-derived resolvins or adenosine or 5-LOX/15-LOX activity or expression levels during a 24-hour period that encompasses the time point at which the early-morning levels are measured. For this, the levels of the one or more n-3 DPA-derived resolvins or adenosine or 5-LOX/15-LOX activity or expression levels in blood samples obtained from one or more subjects may be measured at regular time intervals throughout the day, and this may be easier to achieve in the context of a clinical trial or clinical in-patient setting.

The methods of the present invention may be performed by a computer.

Accordingly, in another aspect the present invention there is provided a computer-implemented method of assessing the efficacy of a therapeutic or preventative treatment for cardiovascular disease in a subject, which comprises receiving in a computer sample data representing the levels of at least one n-3 DPA-derived resolvin or the levels of adenosine or 5-LOX/15-LOX activity or expression in blood samples obtained from the subject early in the morning respectively before and after commencing treatment and executing software on the computer to compare the levels of the at least one n-3 DPA-derived resolvin or the levels of adenosine or 5-LOX/15-LOX activity or expression in the samples, an increase in the level of the at least one n-3 DPA-derived resolvin or a decrease in the activity or expression of adenosine or an increase in the expression or activity of 5-LOX or 15-LOX after commencing treatment being indicative of efficacy of the treatment, and to output efficacy data representing the efficacy of the treatment on the basis of the comparison.

In yet another aspect of the present invention there is provided a computer-implemented method of assessing the efficacy of a therapeutic or preventative treatment for cardiovascular disease in a subject, which comprises receiving in a computer sample data representing the levels of at least one n-3 DPA-derived resolvin or the levels of expression or activity of adenosine or 5-LOX/15-LOX in a series of at least two sets of blood samples obtained from the subject, one sample in each set being obtained from the subject early in the morning, and the other sample in each set being obtained from the subject at a different time of day, and executing software in the computer to calculate the difference in the levels of the at least one n-3 DPA-derived resolvin and/or the expression or activity of adenosine or 5-LOX/15-LOX between the early morning and other time of day samples in each set, and to compare the differences in levels for the sets of samples in the series; wherein an increase in the difference between the levels of the at least one n-3 DPA-derived resolvin or a decrease in the activity or expression of adenosine or an increase in the expression or activity of 5-LOX/15-LOX in the early morning and other time-of-day samples after commencing the treatment is indicative of the efficacy of the treatment.

In yet another aspect, the present invention comprehends computer-executable software for carrying out the methods of the invention for assessing the efficacy of therapeutic or preventative treatments for cardiovascular disease as described above.

It will be appreciated that the step of comparing the levels of the at least one n-3 DPA-derived resolvin in the samples may be carried out on a different computer from a computer that initially receives data representing the levels of the n-3 DPA-derived resolvin in the samples In yet another aspect of the present invention, therefore, there is provided computer apparatus for assessing the efficacy of a therapeutic or preventative treatment for cardiovascular disease in a subject, which comprises a first device incorporating a computer, a second computer and a communication channel between the first device and second computer for the transmission of data therebetween; wherein the first device is arranged to receive sample data representing the levels of at least one n-3 DPA-derived resolvin or the levels of expression or activity of adenosine or 5-LOX/15-LOX in blood samples obtained from the subject early in the morning respectively before and after commencing the treatment and to transmit the sample data to the second computer via the communication channel, and the second computer is arranged to execute software to compare the levels of the at least one n-3 DPA-derived resolvin or the levels of expression or activity of adenosine or 5-LOX/15-LOX in the samples to determine the efficacy of the treatment for the subject, an increase in the level of the at least one n-3 DPA-derived resolvin or a decrease in the activity or expression of adenosine or an increase in the expression or activity of 5-LOX/15-LOX after commencing the treatment being indicative of efficacy of the treatment, and output efficacy data representing the efficacy of the treatment.

In yet another aspect, the invention comprehends computer apparatus for assessing the efficacy of a therapeutic or preventative treatment for cardiovascular disease in a subject, which comprises a first device incorporating a computer, a second computer and a communication channel between the first device and second computer for the transmission of data therebetween; wherein the first device is arranged to receive sample data representing the levels of at least one n-3 DPA-derived resolvin in a series of pairs of blood samples obtained from the subject undergoing the treatment, one sample in each pair being obtained from the subject early in the morning, and the other sample in each pair being obtained from the subject at a different time of day, and to transmit the sample data to the second computer via the communication channel; and the second computer is arranged to execute software to calculate the difference in the levels of the at least one n-3 DPA-derived resolvin between the early morning and different time-of-day samples in each pair of samples and to compare the differences in the levels between the pairs of samples in the series, an increase in the difference between the early morning and different time-of-day levels of the at least one n-3 DPA-derived resolvin after treatment being indicative of efficacy of the treatment.

Suitably, the second computer may be arranged to transmit the efficacy data to the first device via the communication channel, or to a third computer.

In some embodiments, the first device may incorporate an immunoassay, equipment or a device in accordance with the above-described corresponding aspects of the invention for measuring the level of at least one n-3 DPA-derived resolvin in a blood sample.

Following is a description by way of example only with reference to the accompanying drawings of embodiments of the present invention.

Figure 2:
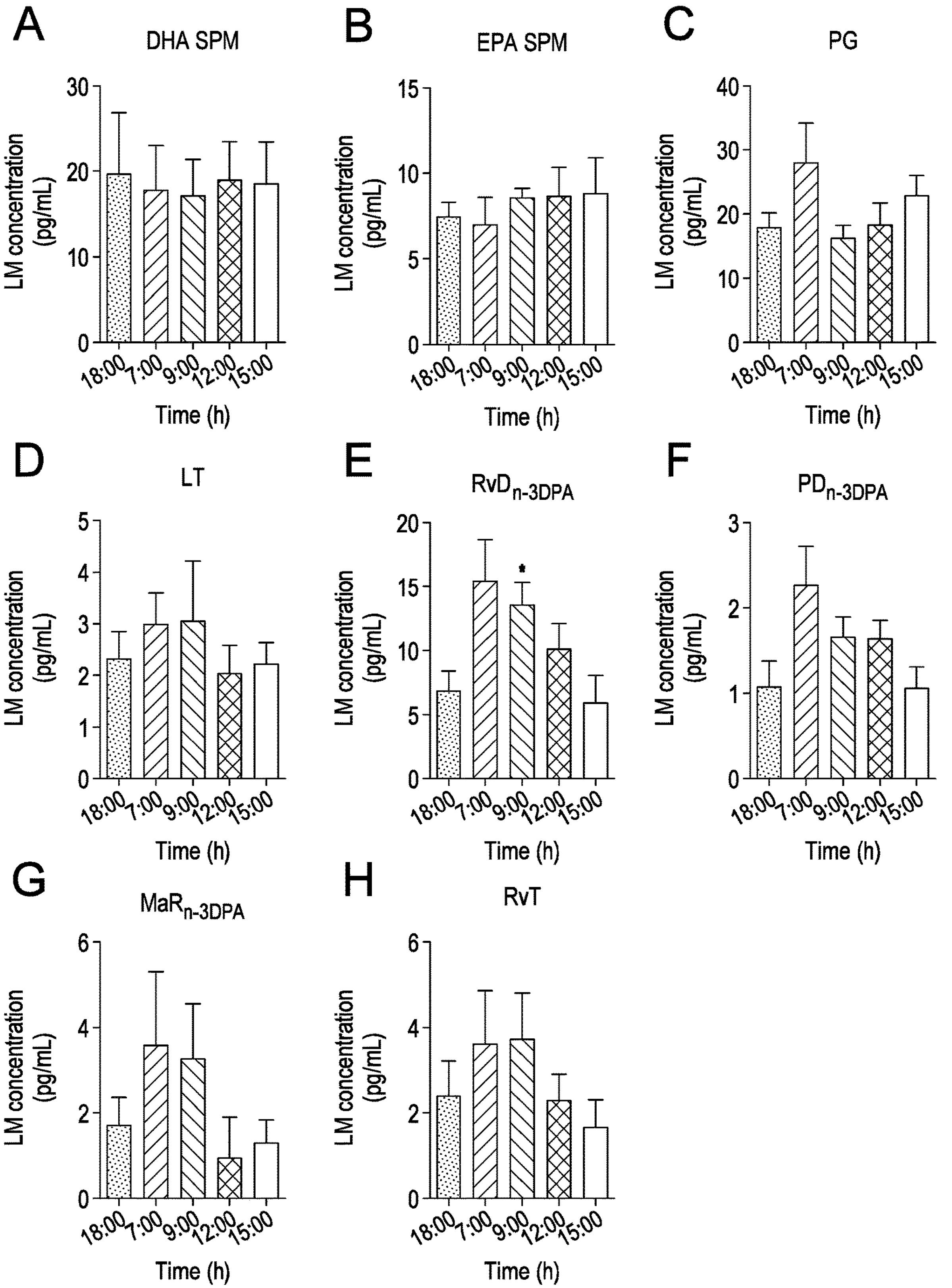

FIG. 2: Diurnal regulation of LM-SPM healthy volunteers. Peripheral blood from healthy volunteers was collected at the indicated intervals. Plasma was collected and placed in ice-cold methanol containing deuterium labelled internal standards. LM extracted, identified and quantified using LM profiling (see methods for details). Concentration of (A) DHA metabolome, (B) EPA metabolome, (C) PG (D) $LTB_4$ metabolome, (E) $RvD_{n-3\ DPA}$, (F) $PD_{n-3\ DPA}$, (G) $MaR_{n-3\ DPA}$ and (H) RvT. Results are mean±s.e.m, expressed as pg/mL. n=7 volunteers per interval.

Figure 3:
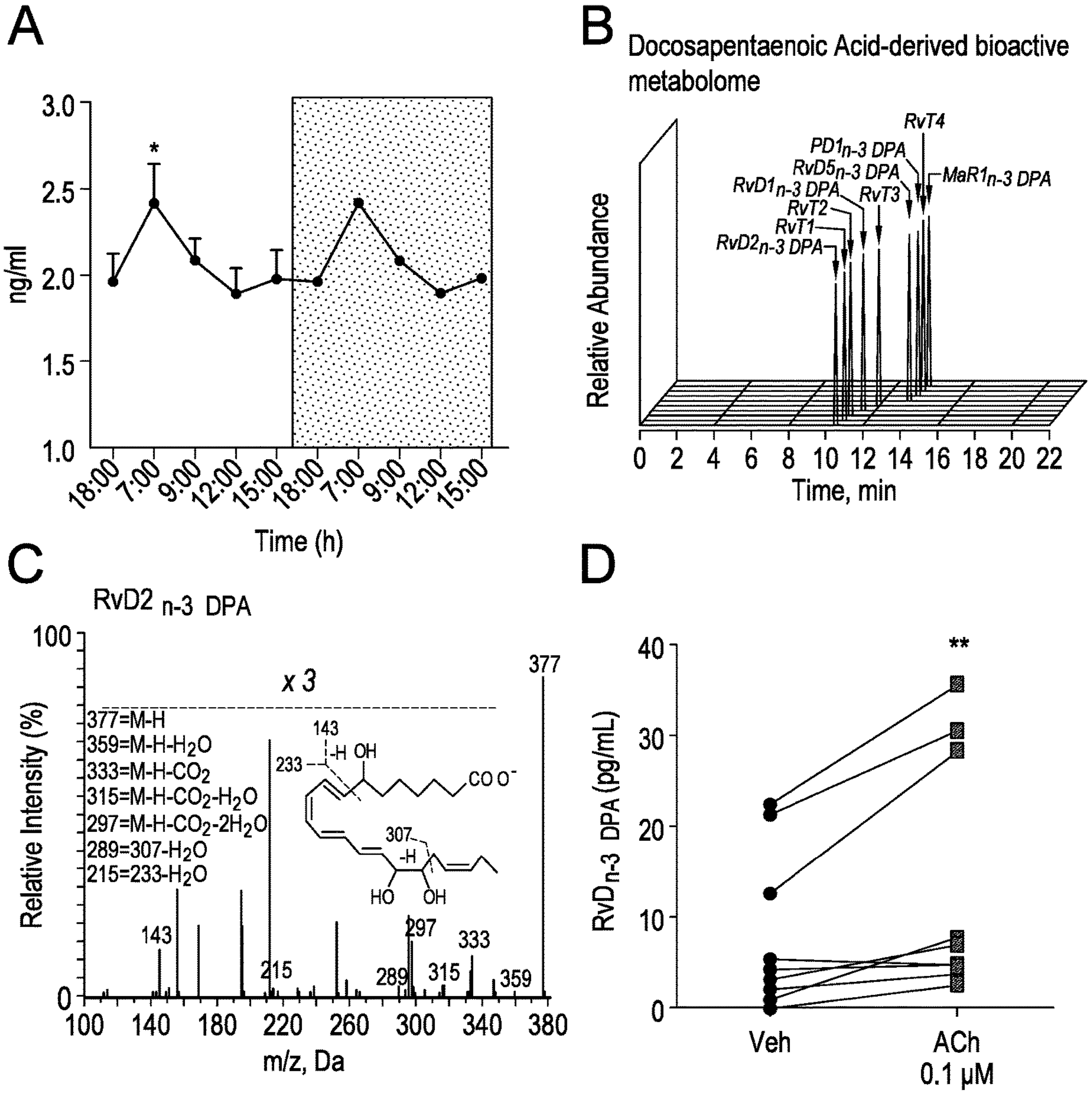

FIG. 3: Acetylcholine up-regulates n-3 DPA SPM in peripheral blood from healthy volunteers. (A) Blood was collected from healthy volunteers, acetylcholine levels determined using LC/MS-MS Results are mean±s.e.m, n=7 healthy donors per condition and expressed as pg/mL. *, p≤0.05 vs 18 h concentrations. Results in the grey panel are re-plotted from the white portion to aid in visualization of rhythmicity (B-D) Blood was collected from healthy volunteers and incubated with acetylcholine (ACh; 0.1 μM; 45 min; 37° C.). Incubations were quenched with ice-cold methanol and n-3 DPA-derived LM identified and quantified using LM-profiling (see methods for details). (B) Representative MRM for the identified n-3 DPA SPM (B,C) MS-MS spectra used for the identification of (C) RvD2-3 DPA. Results are representative of n=6 healthy donors. (D) Plasma n-3 DPA D-series resolvin concentrations. Results are mean±s.e.m, n=9 healthy donors per condition and expressed as pg/mL. **, p≤0.01 vs vehicle incubations (Veh).

Figure 4:
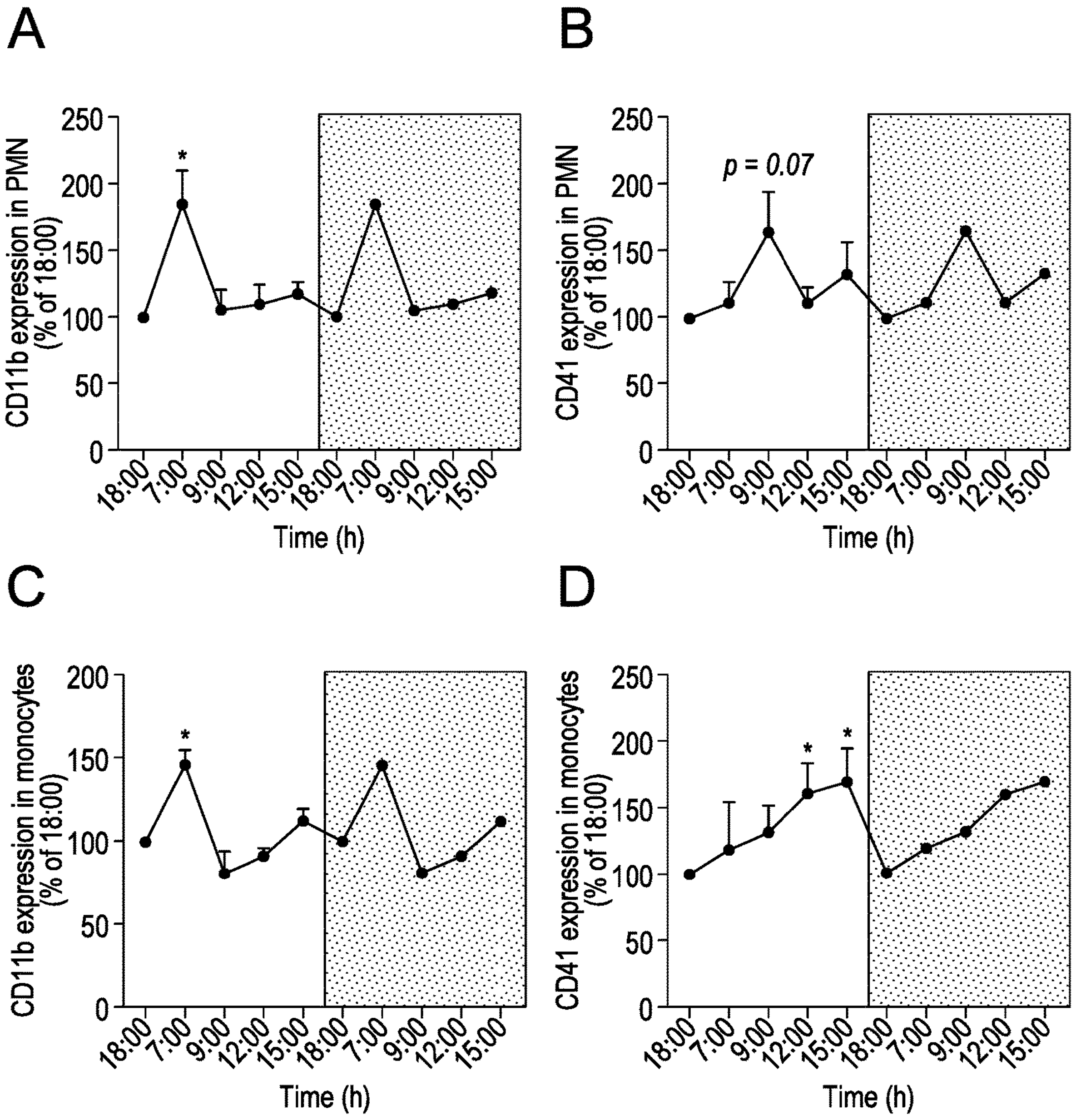

FIG. 4: Diurnal regulation of peripheral blood leukocyte and platelet activation in healthy volunteers. Blood was collected at the indicated intervals and the expression of neutrophil, monocyte and platelet activation markers was assessed using fluorescently labelled antibodies and flow cytometry. (A,B) Neutrophil (A) CD11b and (B) CD41 expression. (C,D) Monocyte (C) CD11b and (D) CD41 expression. Results are mean±s.e.m, n=7 volunteers per interval and expressed as percentage of 18:00 h antigen expression. *p<0.05 vs 18:00 h interval, determined using repeated measures one-way ANOVA followed by Tukey's test.

Figure 5:
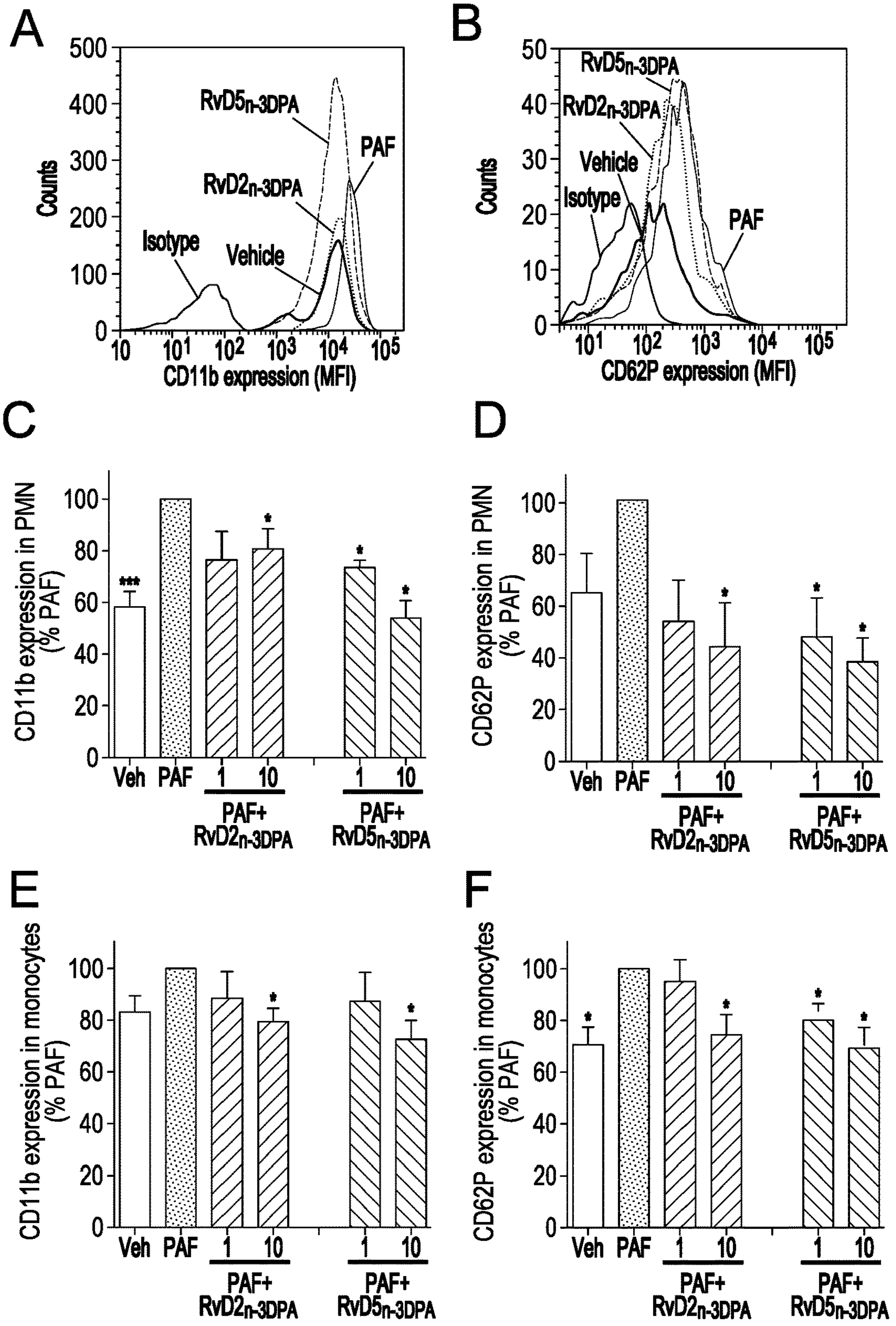

FIG. 5: $RvD2_{n-3\ DPA}$ and $RvD5_{n-3\ DPA}$ reduce monocyte, neutrophil and platelet activation in healthy volunteer peripheral blood. Blood was collected from healthy volunteers and incubated with $RvD2_{n-3\ DPA}$, $RvD5_{n-3\ DPA}$ (0.1 nM, 1 nM or 10 nM) or vehicle (PBS) for 15 min (37° C.) then with PAF (100 ng/ml; 30 min; 37° C.). Cell activation and leukocyte-platelet aggregates were assessed using flow cytometry. (A,B) Representative histograms depicting neutrophil (A) CD11b and (B) CD62P expression. (C,D) Cumulative neutrophil (D) CD11b and (D) CD62P expression. (E,F) Monocyte (E) CD11b and (F) CD62P expression. Results are mean of n=5 per time point and expressed as percentage change from PAF incubated cells. *p<0.05 compared to PAF using one-sample t test, followed by Sidak correction of p values.

Figure 6:
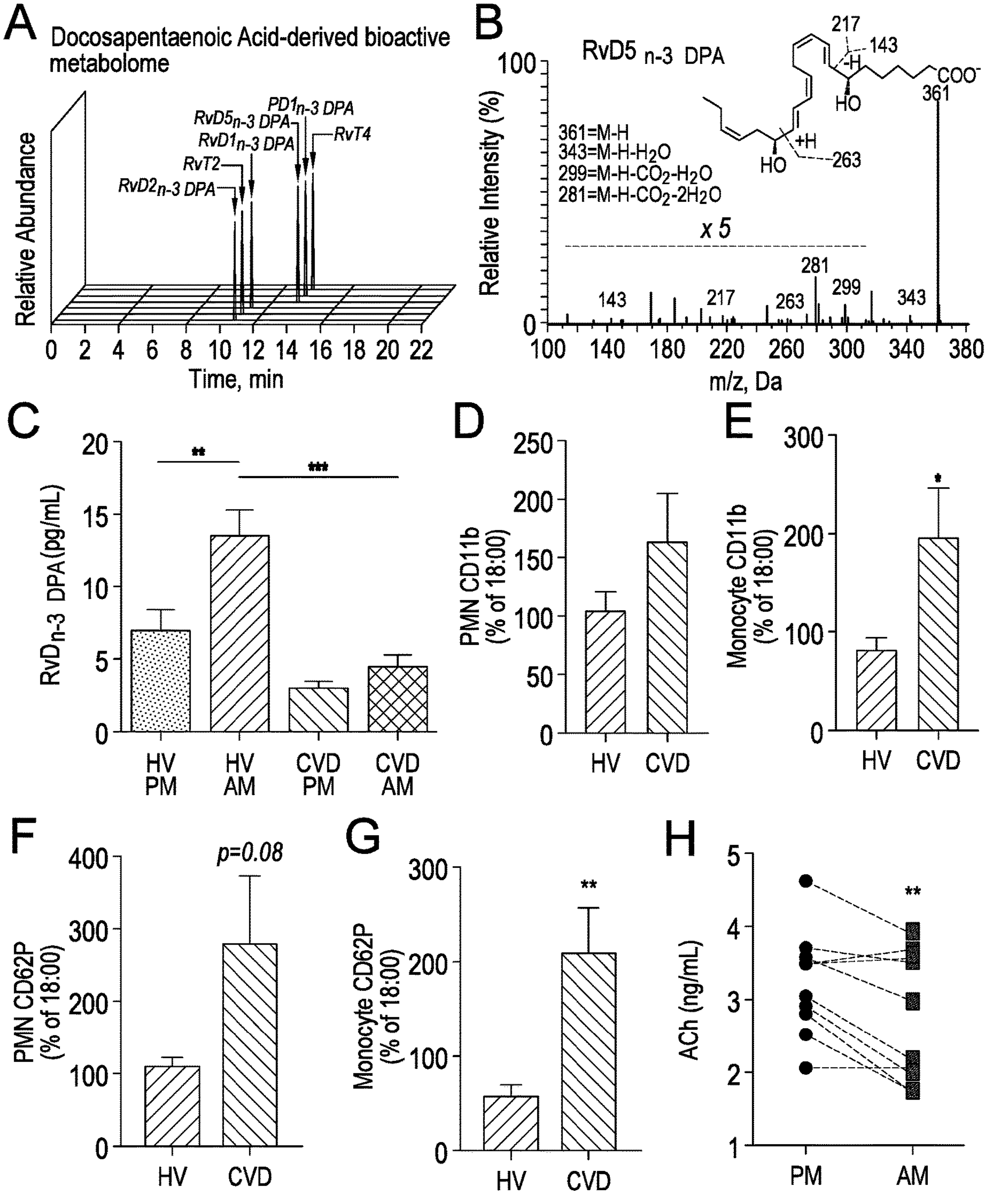

FIG. 6. Systemic n-3 DPA-derived SPM are reduced and leukocyte activation is increased in patients with CVD. Peripheral blood from patients diagnosed with cardiovascular disease (CVD) was collected at 9:00 h (AM) and 16:00-18:00 h (PM). Plasma was placed in ice-cold methanol containing internal standards and LM identified and quantified using LM-profiling (see methods for details). (A) Representative MRM for the identified n-3 DPA SPM. (B) MS-MS spectra used for the identification of $RvD5_{n-3\ DPA}$. Results are representative of n=9 CVD patients. (C) Plasma $RvD_{n-3\ DPA}$ concentrations. Results are mean±s.e.m. and expressed as pg/mL. n=9 CVD patients and n=7 healthy volunteers (HV). *, p≤0.05 and , p≤0.01 compared to indicated control. (D-G) Whole blood was incubated with fluorescently labeled antibodies and cell activation as well as leukocyte-platelet aggregates were assessed using flow cytometry. (D,E) CD11b expression on (D) neutrophils and (E) monocytes. (F,G) CD62P expression on (F) neutrophils and (G) monocytes. (H) Plasma ACh concentrations. Results are mean±s.e.m. and expressed as percentage antigen expression at 18:00 h interval. n=5 HV and, 9 CVD patients. p<0.01 compared to HV determined using Unpaired t-test.

Figure 7:
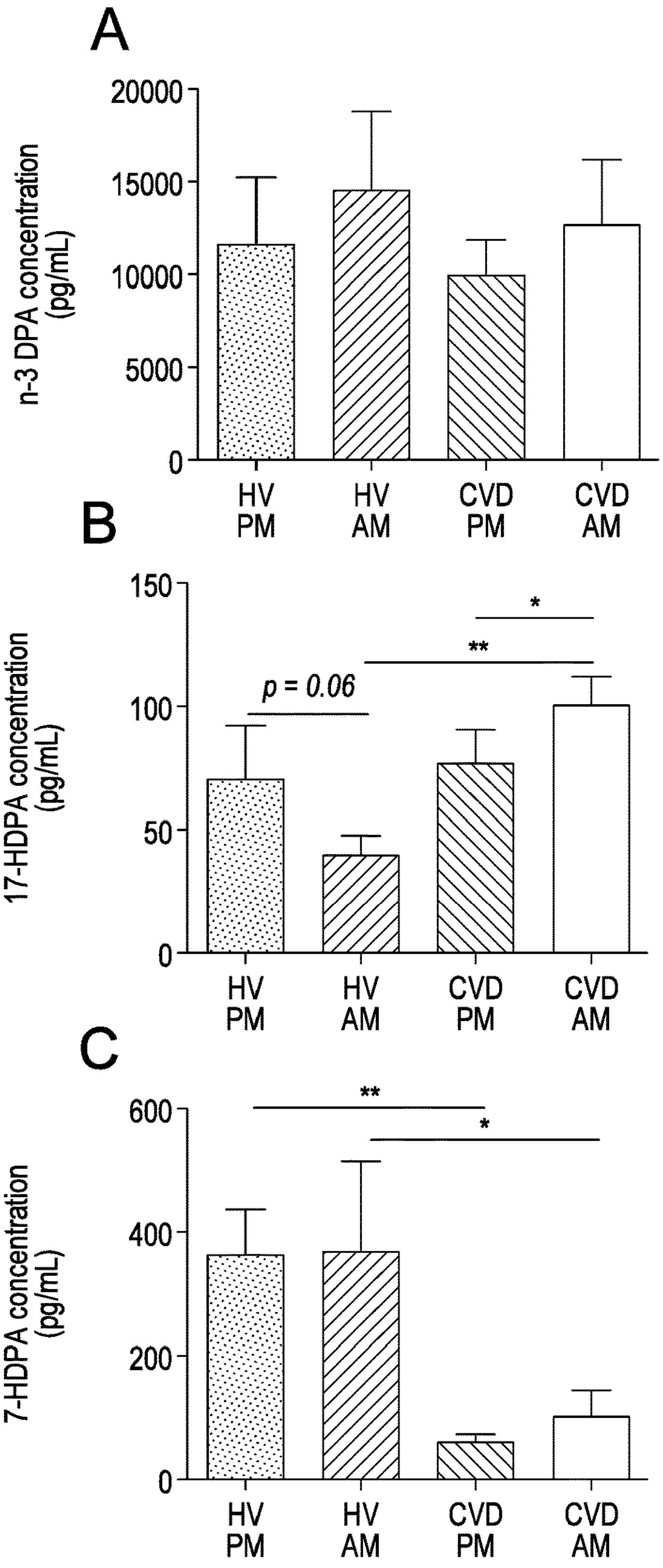

FIG. 7: Dysregulated $RvD_{n-3\ DPA}$ pathway in CVD Patients. Peripheral blood was collected from patients with CVD and healthy volunteers (HV) at 9:00 h (AM) and 16:00-18:00 h (PM). Plasma was collected and placed in ice-cold methanol containing deuterium labelled internal standards. LM extracted, identified and quantified using LM profiling (see methods described above for details). (A) n-3 DPA, (B) 17-HDPA and (C) 7-HDPA concentrations. Results are mean±s.e.m, expressed as pg/mL. for A n=4 HV and 11 CVD patients for B-C n=7 HV and 11 CVD patients per interval. * p≤0.05 and ** p≤0.01 compared to indicated control using one-tailed student paired t-test for comparison between HV or CVD and one-tailed student unpaired t-test for comparison between HV and HRMI.

Figure 8:
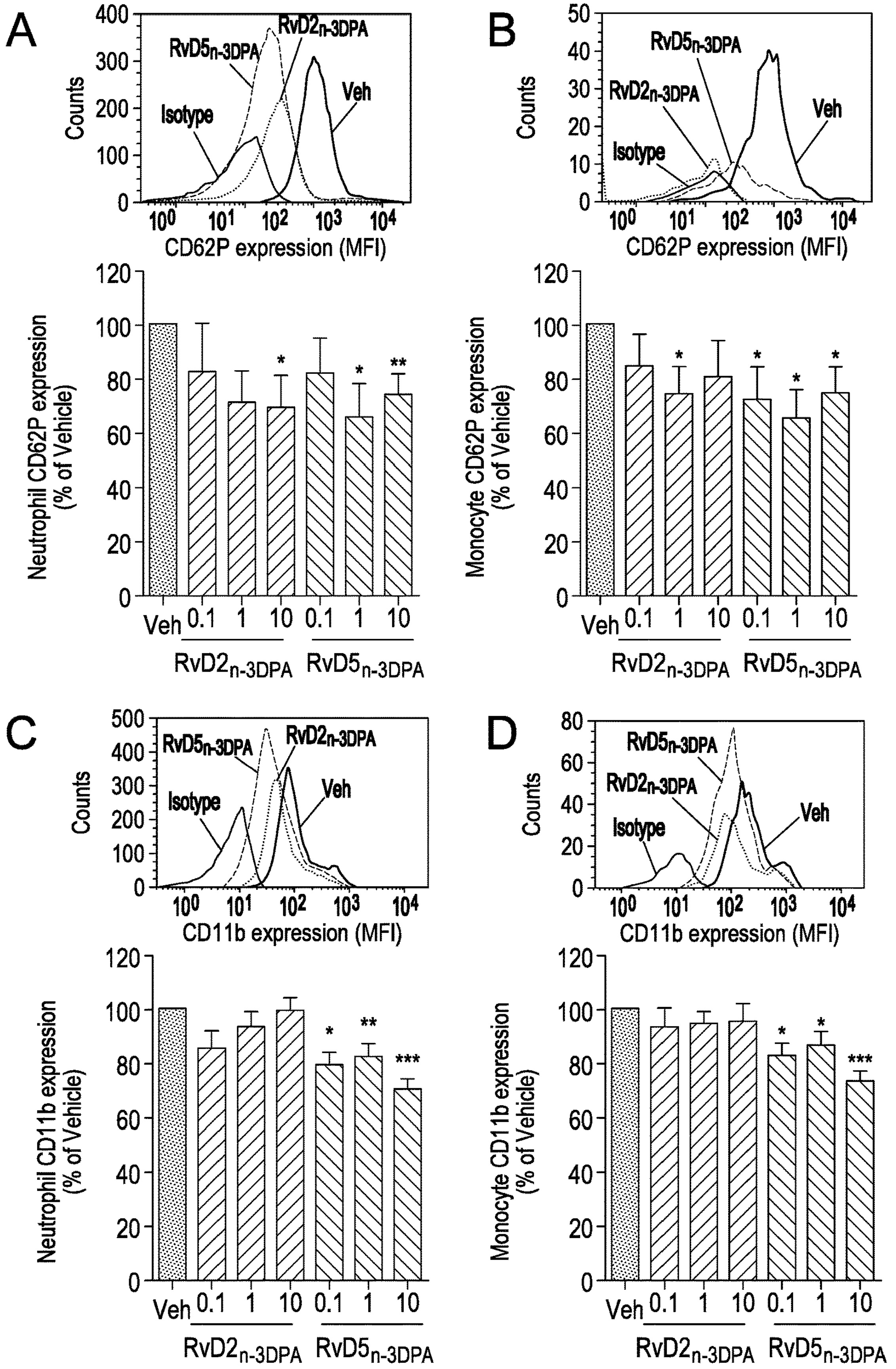

FIG. 8: $RvD2_{n-3\ DPA}$ and $RvD5_{n-3\ DPA}$ reduce leukocyte activation in peripheral blood from CVD patients. Peripheral blood from patients diagnosed with cardiovascular disease (CVD) was collected at 9:00 h. (A D) Whole blood was incubated with $RvD2_{n-3\ DPA}$ or $RvD5_{n-3\ DPA}$ (0.1 nM, 1 nM or 10 nM) or vehicle (PBS containing 0.01% EtOH) for 45 min (37° C.). Expression of CD62P on (A) neutrophils (B) monocytes and CD11b on (C) neutrophils and (D) monocytes was investigated using flow cytometry and fluorescently labelled antibodies. Results are mean±s.e.m and expressed as percentage of Vehicle (Veh) incubated cells. n=8 patients per interval. * p<0.05 vs Veh group using one-sample t test, followed by Sidak correction of p values.

Figure 9:
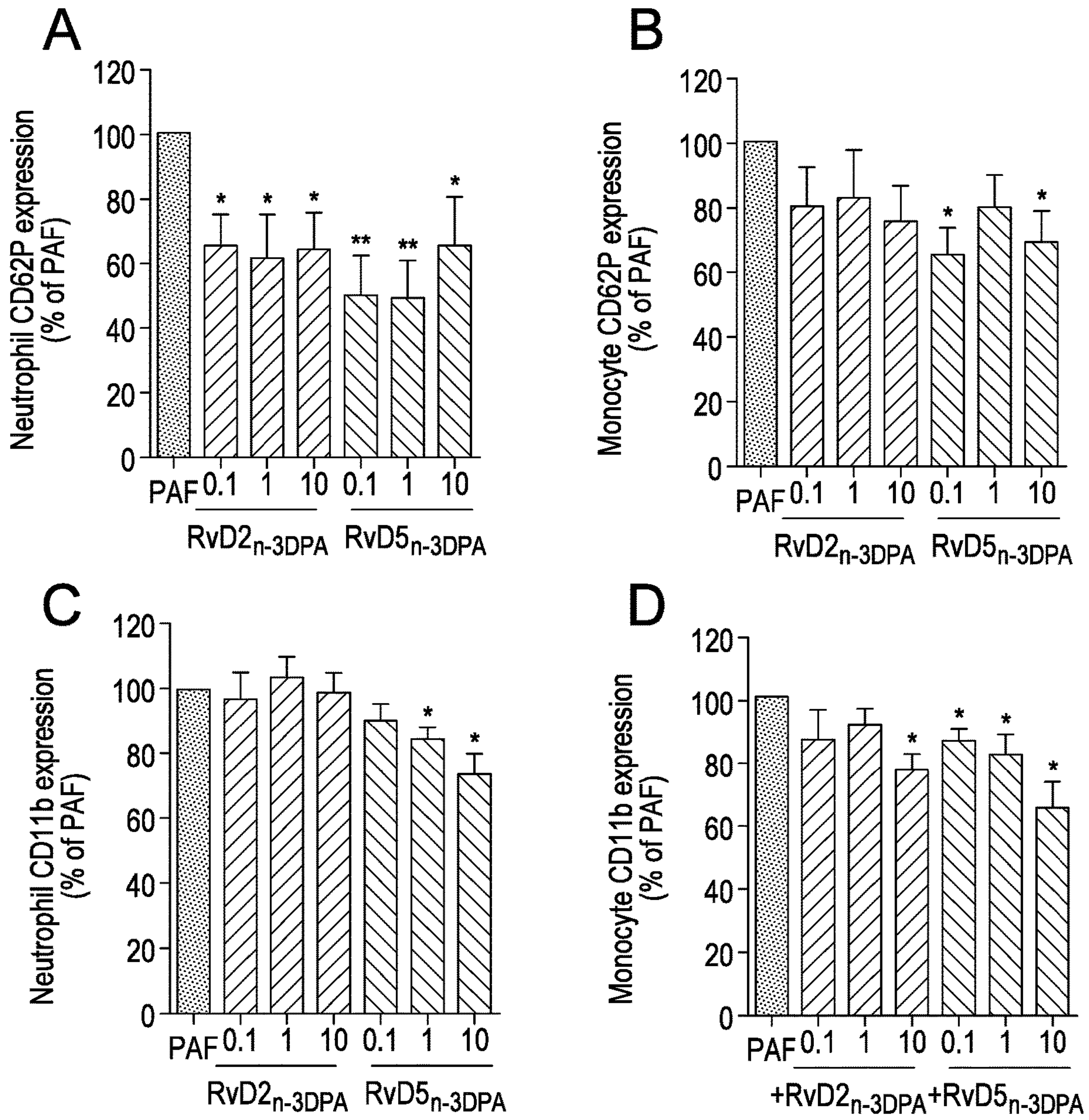

FIG. 9: $RvD2_{n-3\ DPA}$ and $RvD5_{n-3\ DPA}$ counter-regulated PAF induced platelet and leukocyte activation in peripheral blood from CVD patients. Whole blood was incubated with $RvD2_{n-3\ DPA}$ or $RvD5_{n-3\ DPA}$ (0.1 nM, 1 nM or 10 nM) or vehicle (PBS containing 0.01% EtOH) for 15 min then with PAF (100 ng/ml) for 30 min (37° C.). Expression of CD62P on (A) neutrophils (B) monocytes and CD11b on (C) neutrophils and (D) monocytes was investigated using flow cytometry and fluorescently labelled antibodies. Results are mean±s.em. and expressed as percentage of PAF incubated cells. n=9 patients per interval. * p<0.05 vs Veh group using one-sample t test, followed by Sidak correction of p values.

Figure 10:
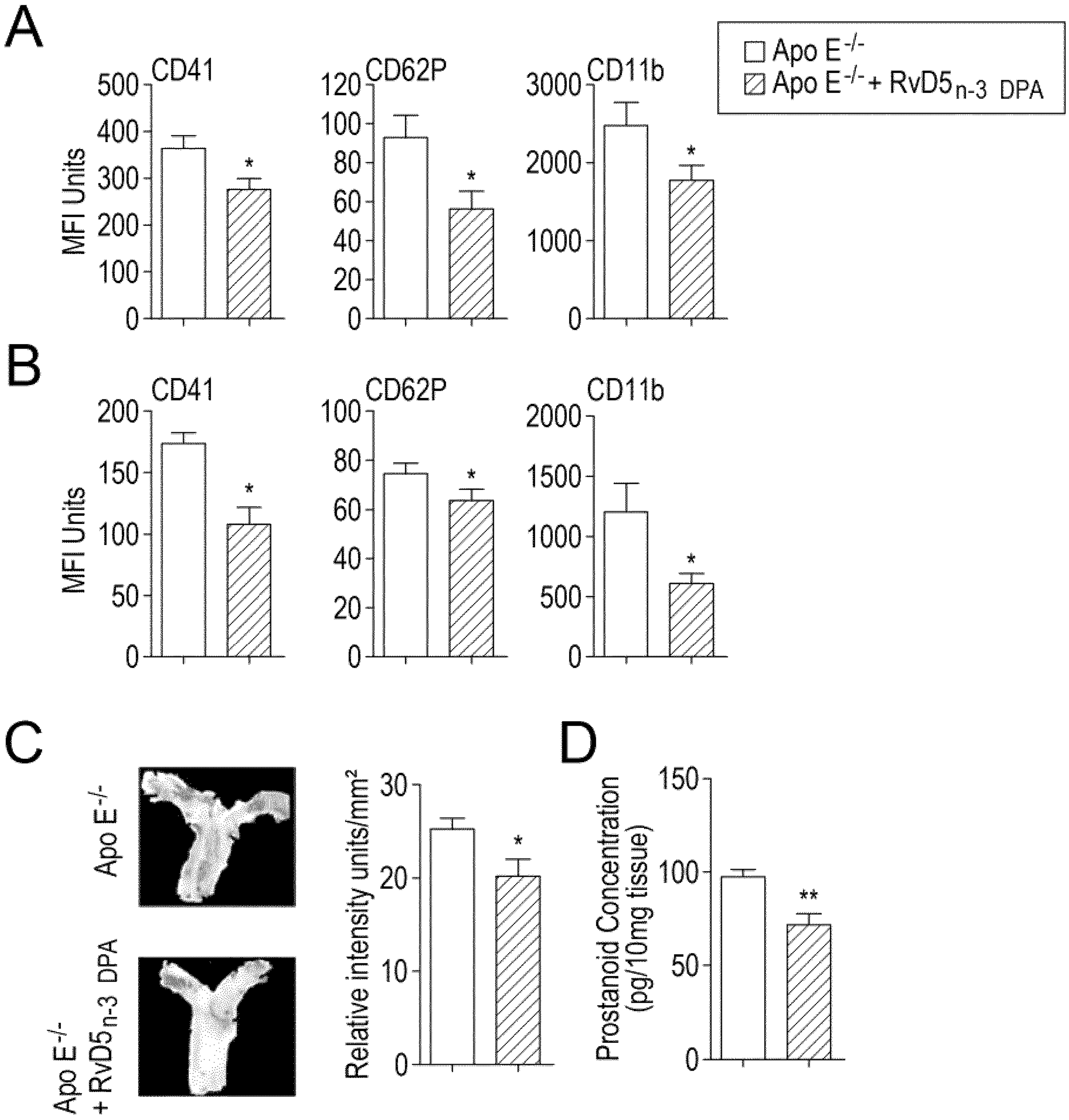

FIG. 10: n-3 DPA reduces RvD5 systemic platelet and leukocyte activation as well as vascular disease in Apo $E^{-/-}$ mice. Apo $E^{-/-}$ mice were fed a western diet for 6 weeks and given $RvD5_{n-3\ DPA}$ (100 ng/mouse; i.v.) on alternate days for 2 weeks. Blood was obtained and (A) monocyte (B) neutrophil expression of CD41, CD62P and CD11b were determined using flow cytometry. (C) Aortic arches were stained using Oil red-O and staining intensity was determined using ImageJ. (D) Descending aortas were harvested and the levels of $PGD_2$, $PGE_2$, $PGF_{2\alpha}$, and $TxB_2$ quantified using LC/MS- MS. Results are mean±s.e.m of 4-5 mice per group. * P<0.05 vs Vehicle treated mice using Students t-Test.

Figure 11:
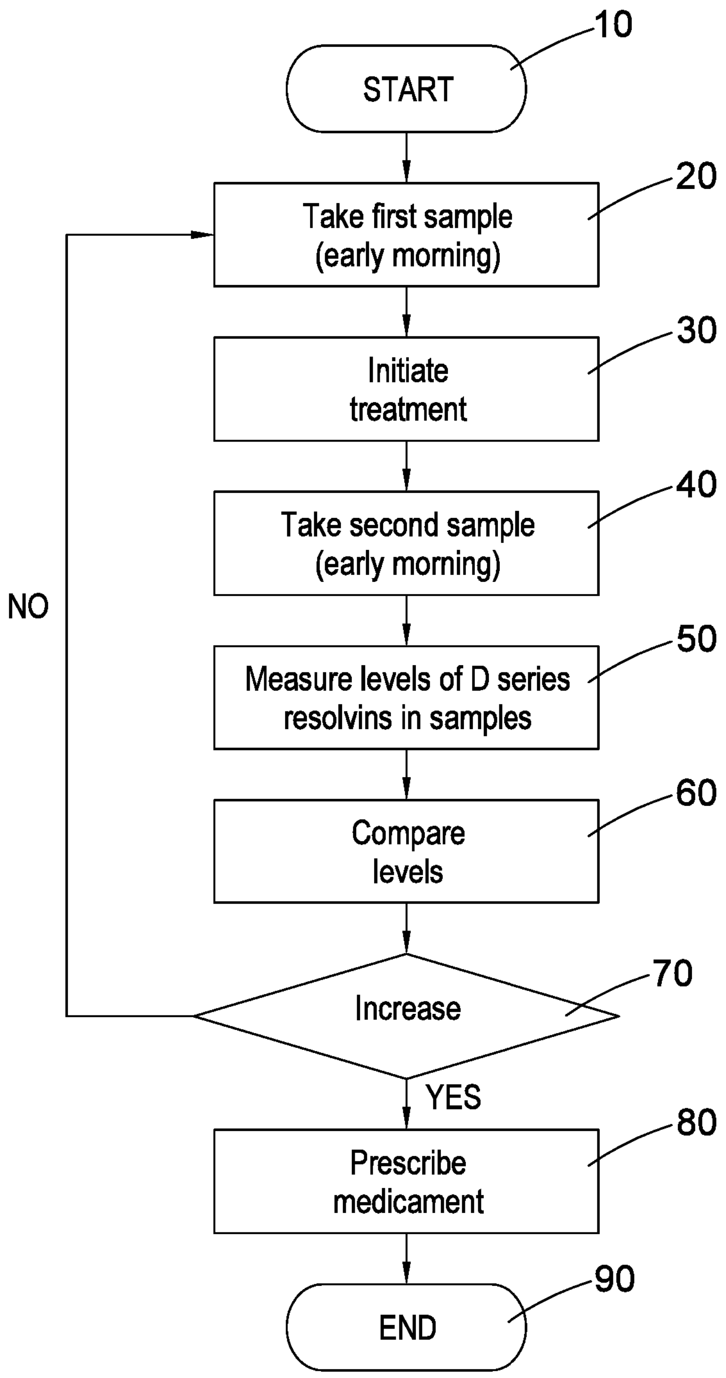

FIG. 11 is a flow diagram illustrating an example of a method of assessing the efficacy of a medicament for use in the treatment or prevention of cardiovascular disease in an individual patient in accordance with the present invention.

Figure 12:
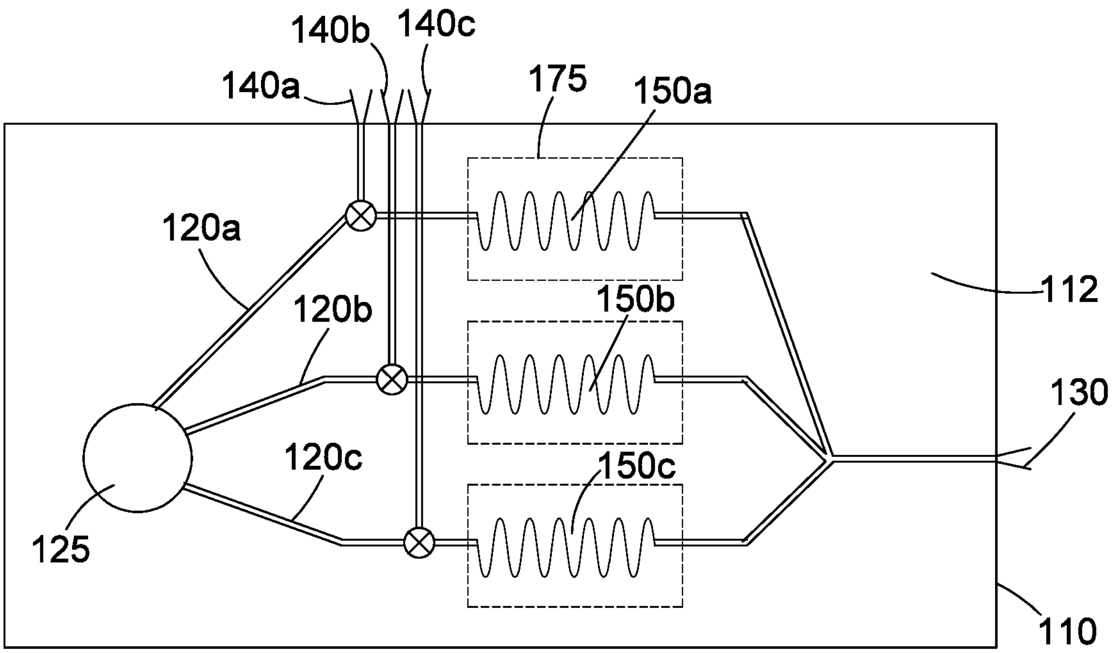

FIG. 12 is a schematic diagram of apparatus for carrying out methods of the present invention using a microfluidic device to carry out an immunoassay.

Figure 13:
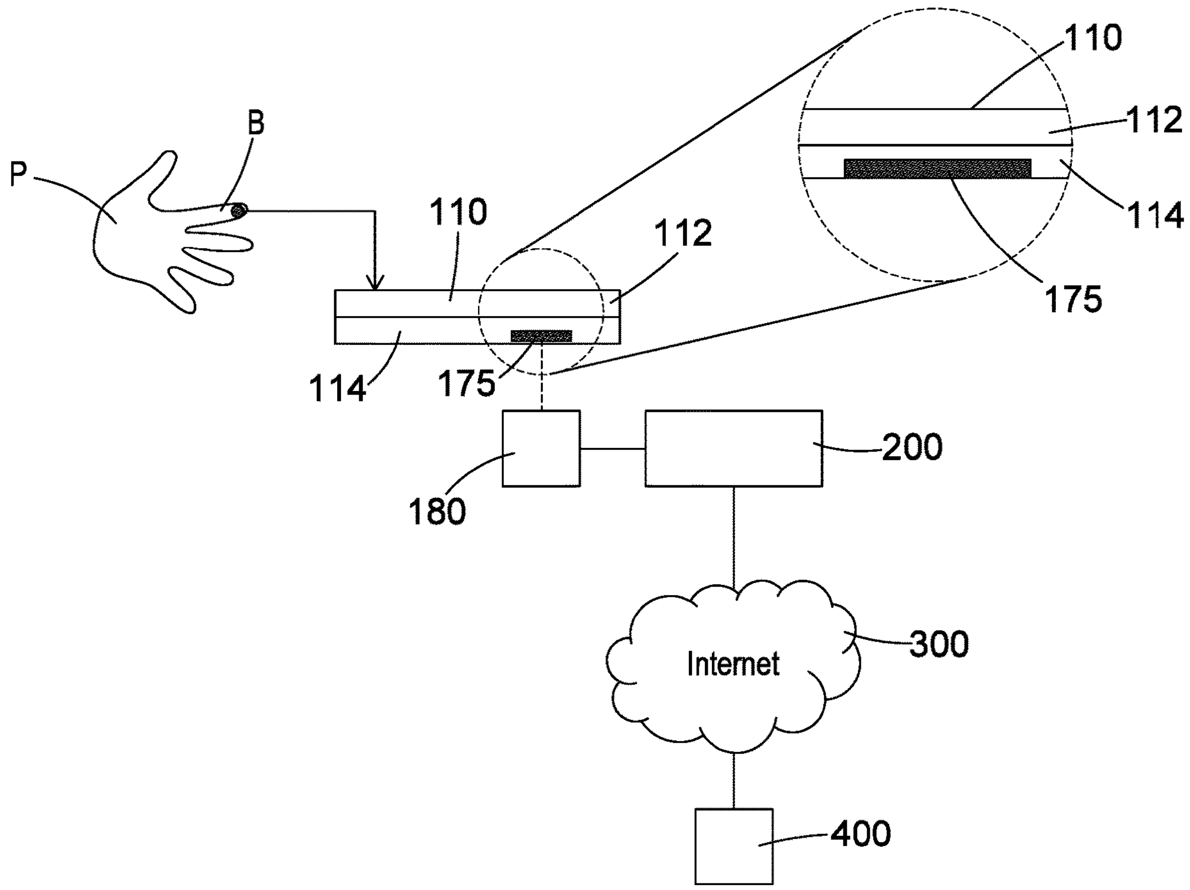

FIG. 13 is a schematic diagram of a microfluidic device according to the present invention which incorporates an immunoassay of the invention.

Figure 14:
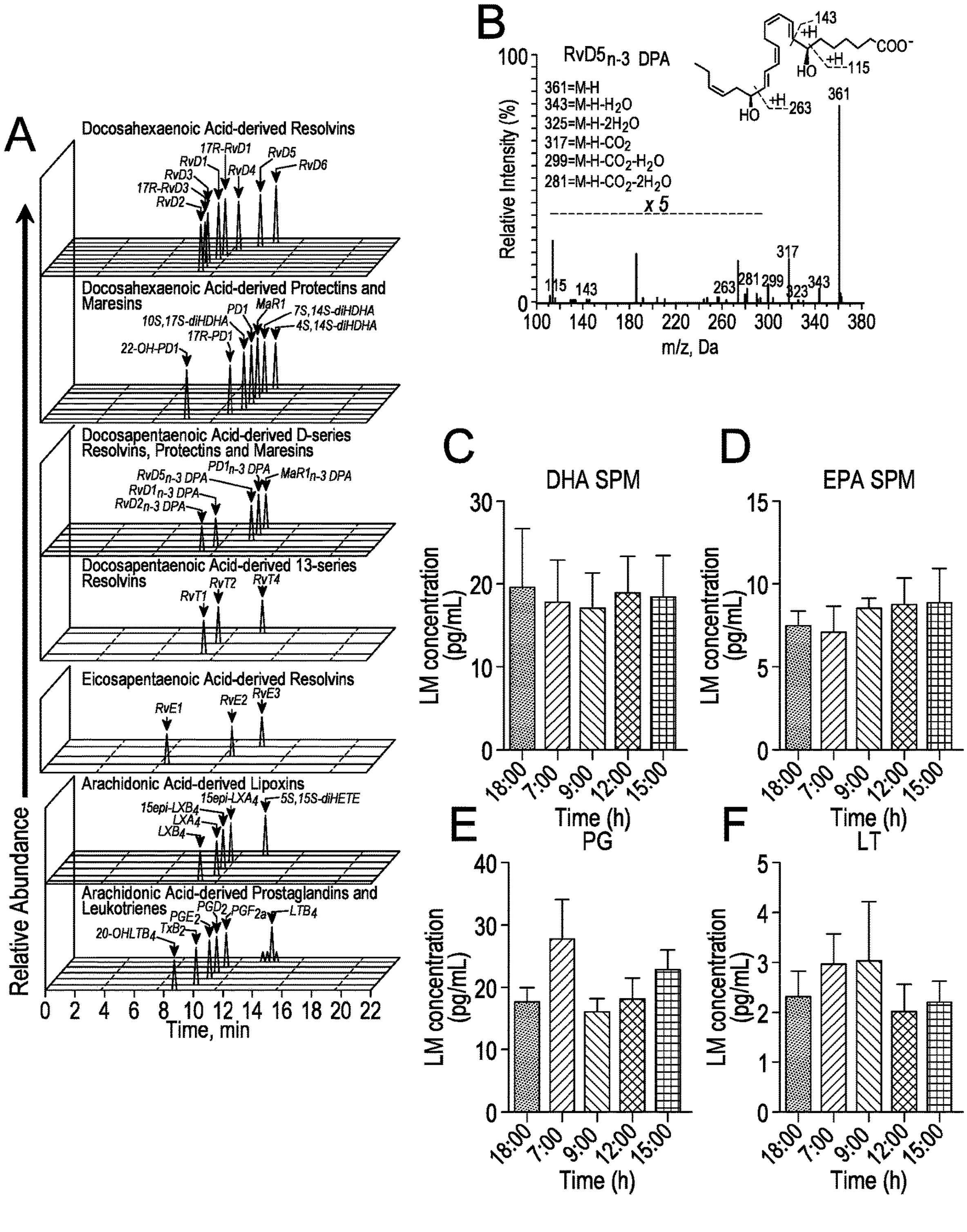

FIG. 14: Diurnal regulation of LM-SPM healthy volunteers. Peripheral blood was collected from healthy volunteers at the indicated intervals and plasma placed in ice-cold methanol containing deuterium labeled internal standards. Lipid mediators (LM) were extracted, identified and quantified using LM profiling (see methods for details). (A) Representative MRM for identified LM, (B) MS-MS spectra used for the identification of $RvD5_{n\text{-}3\ DPA}$. Results are representative of n=7 healthy volunteers. Concentration of (C) DHA metabolome, (D) EPA metabolome, (E) PG (F) $LTB_4$ metabolome. Results are mean±s.e.m, expressed as pg/mL. n=7 volunteers per interval. (G) Blood was collected from WT and BMAL1-LysM$^{-/-}$ mice at 21:00, 11:00 and 16:00 h and RvDn-3 DPA were identified and quantified using lipid mediator profiling. Results are mean±s.e.m, n=3 mice per group.

Figure 15:
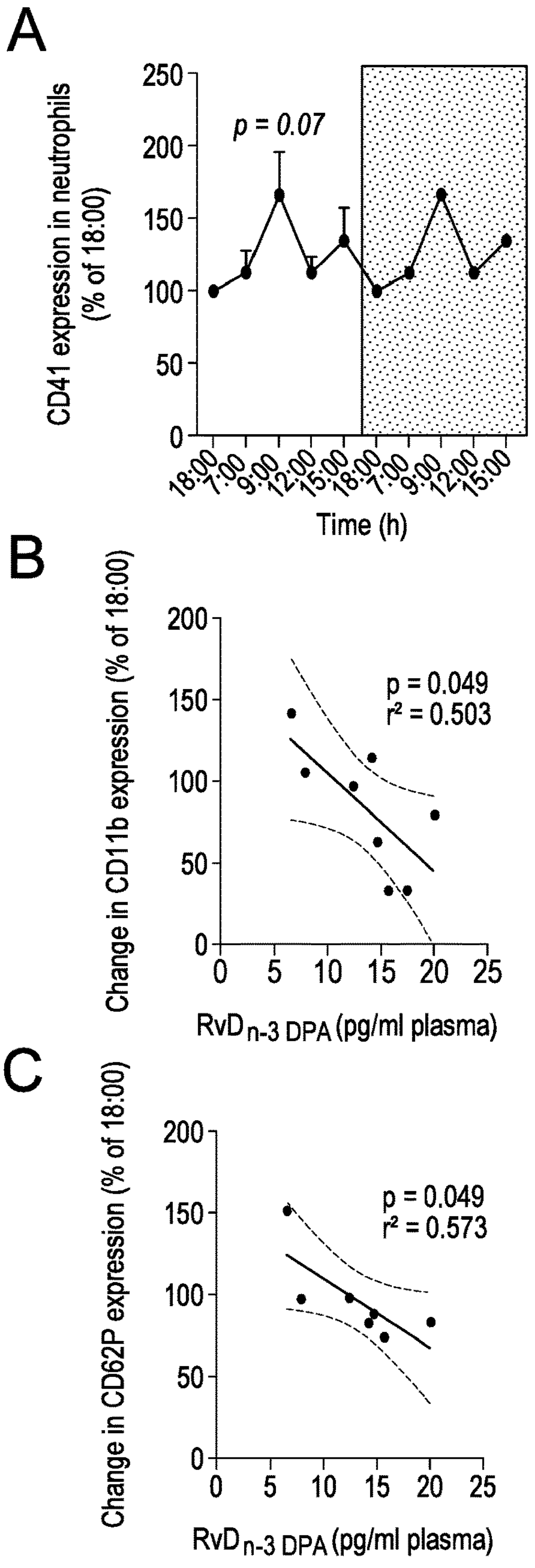

FIG. 15: Morning $RvD_{n\text{-}3\ DPA}$ concentrations negatively correlate with peripheral blood neutrophil activation. Peripheral blood was collected from healthy volunteers at the indicated intervals, LM concentrations determined using LM profiling (see methods for details) and neutrophil and platelet activation determined using fluorescently labelled antibodies and flow cytometry. (A) Neutrophil CD41 expression. Results are mean±s.e.m, n=7 volunteers per interval and expressed as percentage of 18:00 h antigen expression. Results in the grey panel are re-plotted from the white portion to aid in visualization of rhythmicity. (B, C) Correlation between changes in neutrophil (B) CD11b and (C) CD62P (9:00 to 18:00) expression and 9:00 $RvD_{n\text{-}3\ DPA}$ concentrations. Results are representative of n=8 volunteers. Dashed line represents 95% confidence interval.

Figure 16:
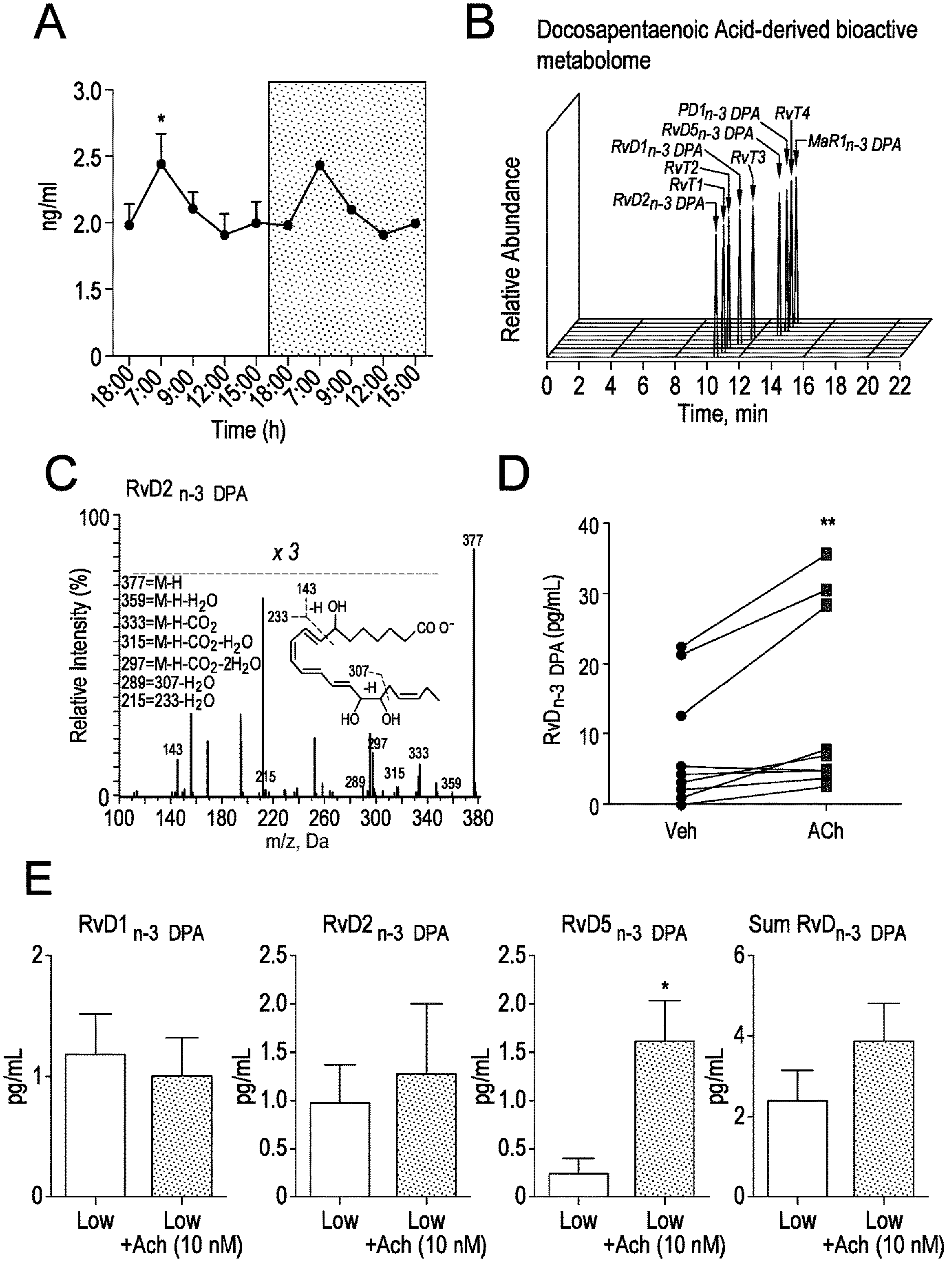

FIG. 16: Acetylcholine up-regulates n-3 DPA SPM in peripheral blood from healthy volunteers. (A) Blood was collected from healthy volunteers and acetylcholine levels determined using LC/MS-MS. Results are mean±s.e.m, n=7 healthy donors per condition and expressed as ng/mL. *, p≤0.05 vs 18 h concentrations using Wilcoxon Signed Rank Test. Results in the grey panel are re-plotted from the white portion to aid in visualization of rhythmicity (B-D) Blood was collected from healthy volunteers and incubated with acetylcholine (ACh; 0.1 μM; 45 min; 37° C.). Incubations were quenched with ice-cold methanol and n-3 DPA-derived LM identified and quantified using LM-profiling (see methods for details). (B) Representative MRM for the identified n-3 DPA SPM (B,C) MS-MS spectra used for the identification of (C) $RvD2_{n\text{-}3\ DPA}$. Results are representative of n=9 healthy donors. (D) Plasma $RvD_{n\text{-}3\ DPA}$ concentrations. Results are mean±s.e.m, n=9 healthy donors per condition and expressed as pg/mL. **, p≤0.01 vs vehicle incubations (Veh) using paired Mann-Whitney test. (E) Peripheral blood was incubated in with ACh (10 nM) or Veh (PBS) then perfused at 0.1 Pa for 20 min at 37° C. n=6 healthy volunteers. Plasma was collected and $RvD_{n\text{-}3\ DPA}$ concentrations ascertained using LM profiling. *, p≤0.05 vs vehicle incubations (Veh) using paired Mann-Whitney test.

Figure 17:
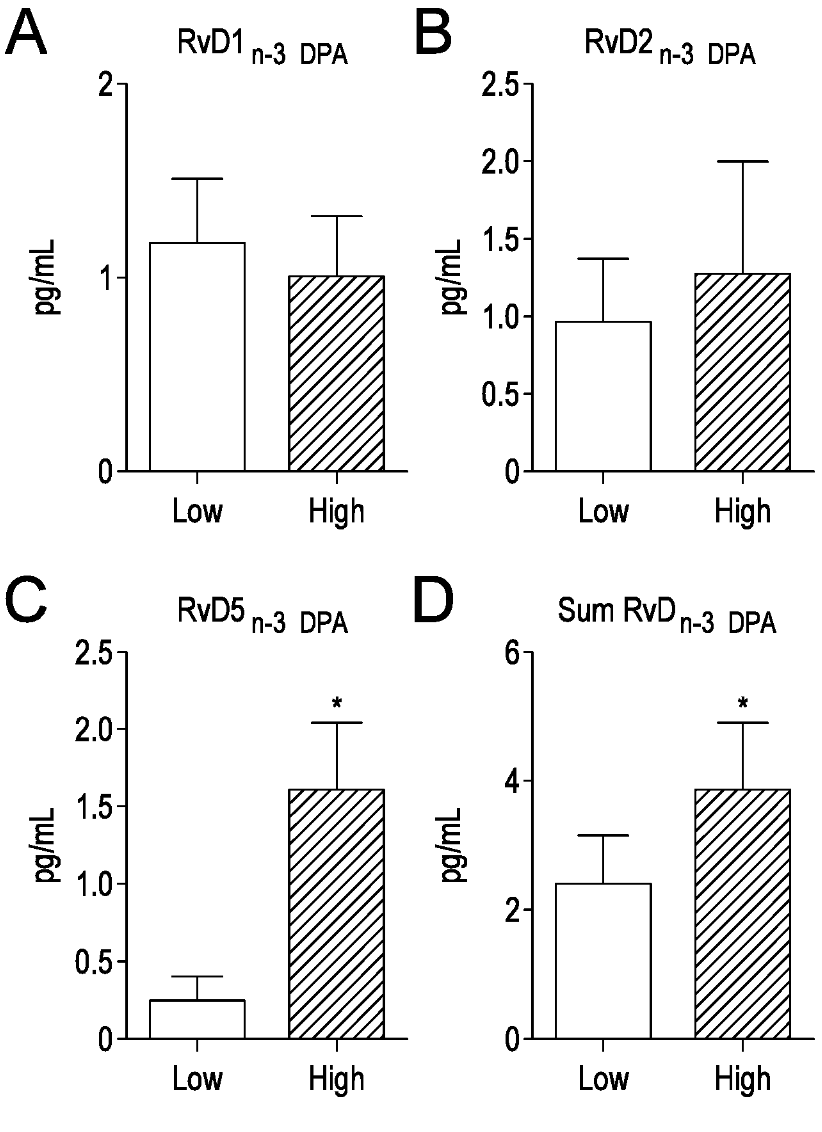

FIG. 17: Increases in sheer upregulate plasma $RvD_{n\text{-}3\ DPA}$. (A) Peripheral blood was perfused at either 0.1 (Low) or 0.3 (High) Pa for 20 min at 37° C. Plasma was collected and $RvD_{n\text{-}3\ DPA}$ concentrations ascertained using LM profiling n=6 healthy volunteers. *, p≤0.05 vs low sheer group using paired Mann-Whitney test.

Figure 18:
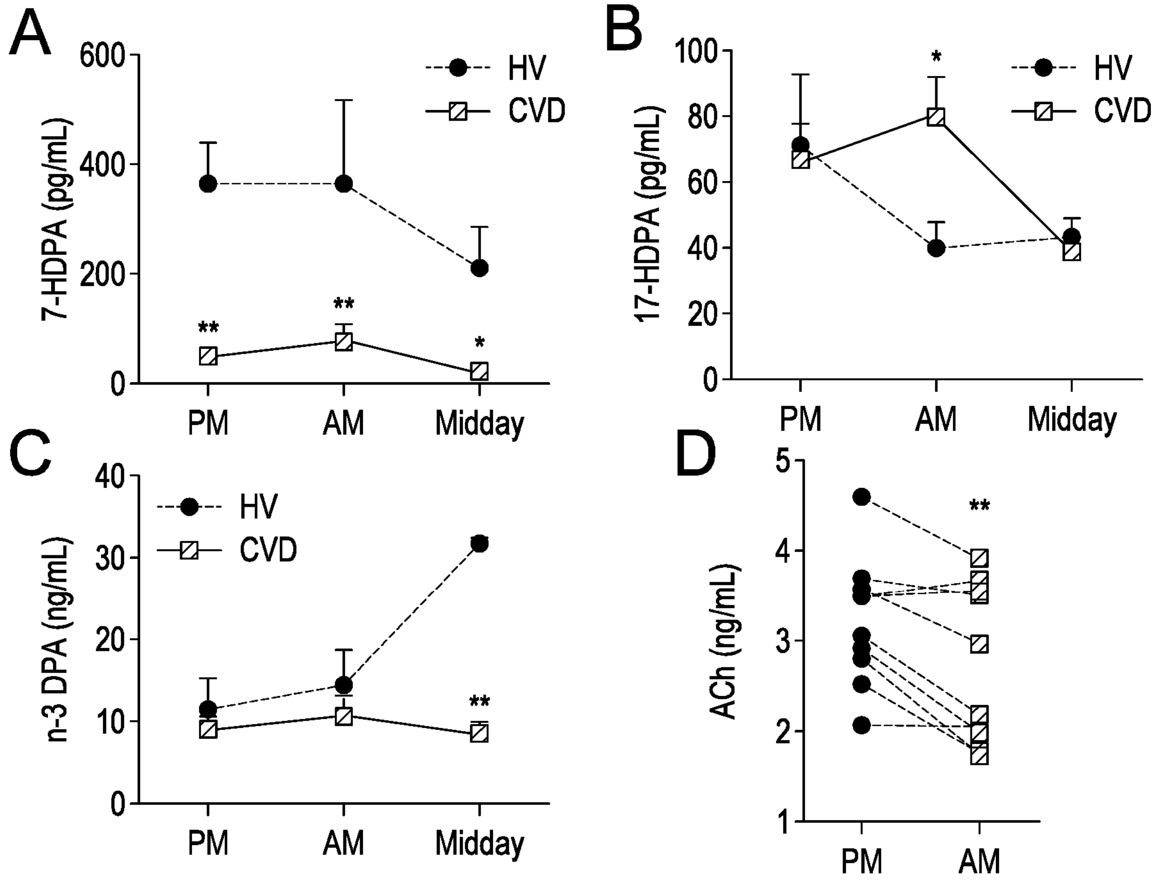

FIG. 18: Dysregulated $RvD_{n\text{-}3\ DPA}$ pathway and ACh in CVD Patients. Peripheral blood was collected from patients with CVD and healthy volunteers (HV) at 9:00 h (AM) 12:00 (mid-day) and 16:00-18:00 h (PM). Plasma was collected and placed in ice-cold methanol containing deuterium labelled internal standards. LM extracted, identified and quantified using LM profiling (see methods for details). (A) 7-HDPA, (B) 17-HDPA and (C) n-3 DPA concentrations. Results are mean±s.e.m, expressed as pg/mL. for A-C n=7 HV per interval, 14 CVD patients for AM, PM and 5 for midday interval. * p 0.05 and ** p 0.01 compared to respective HV $RvD_{n\text{-}3\ DPA}$ concentrations using Mann-Whitney test (D) Plasma ACh concentrations. n=9 patients. * p≤0.05 and compared to PM values using paired Mann-Whitney test.

Figure 19:
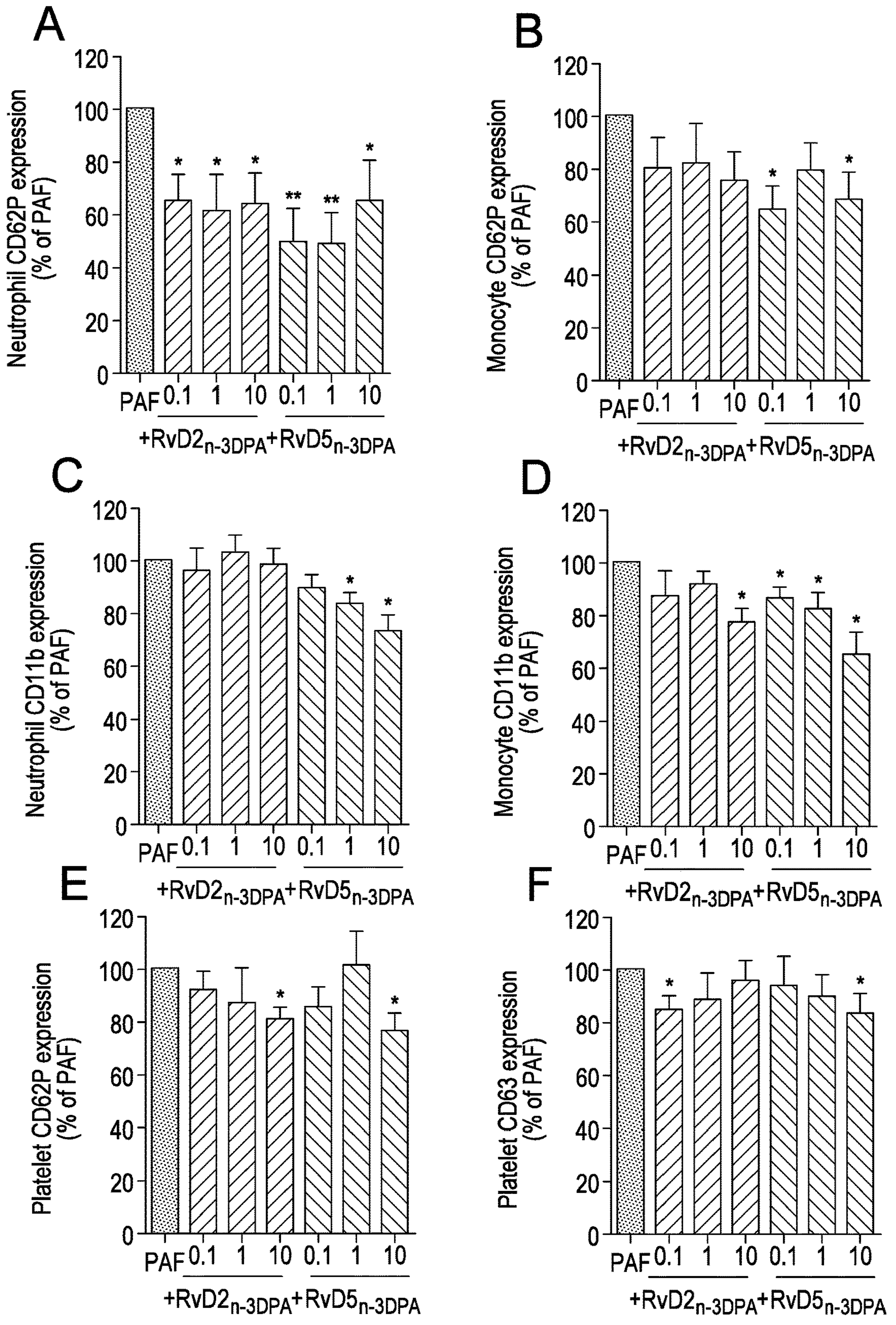

FIG. 19: $RvD2_{n\text{-}3\ DPA}$ and $RvD5_{n\text{-}3\ DPA}$ counter-regulate PAF induced platelet and leukocyte activation in peripheral blood from CVD patients. Whole blood was incubated with $RvD2_{n\text{-}3\ DPA}$ or $RvD5_{n\text{-}3\ DPA}$ (0.1 nM, 1 nM or 10 nM) or vehicle (PBS containing 0.01% EtOH) for 15 min then with PAF (100 ng/ml) for 30 min (37° C.). Expression of CD62P on (A) neutrophils (B) monocytes and CD11b on (C) neutrophils and (D) monocytes was investigated using flow cytometry and fluorescently labeled antibodies. Results are mean±s.em. and expressed as percentage of PAF incubated cells. n=9 patients per group. * p<0.05 vs PAF group using Wilcoxon Signed Rank Test.

Figure 20:
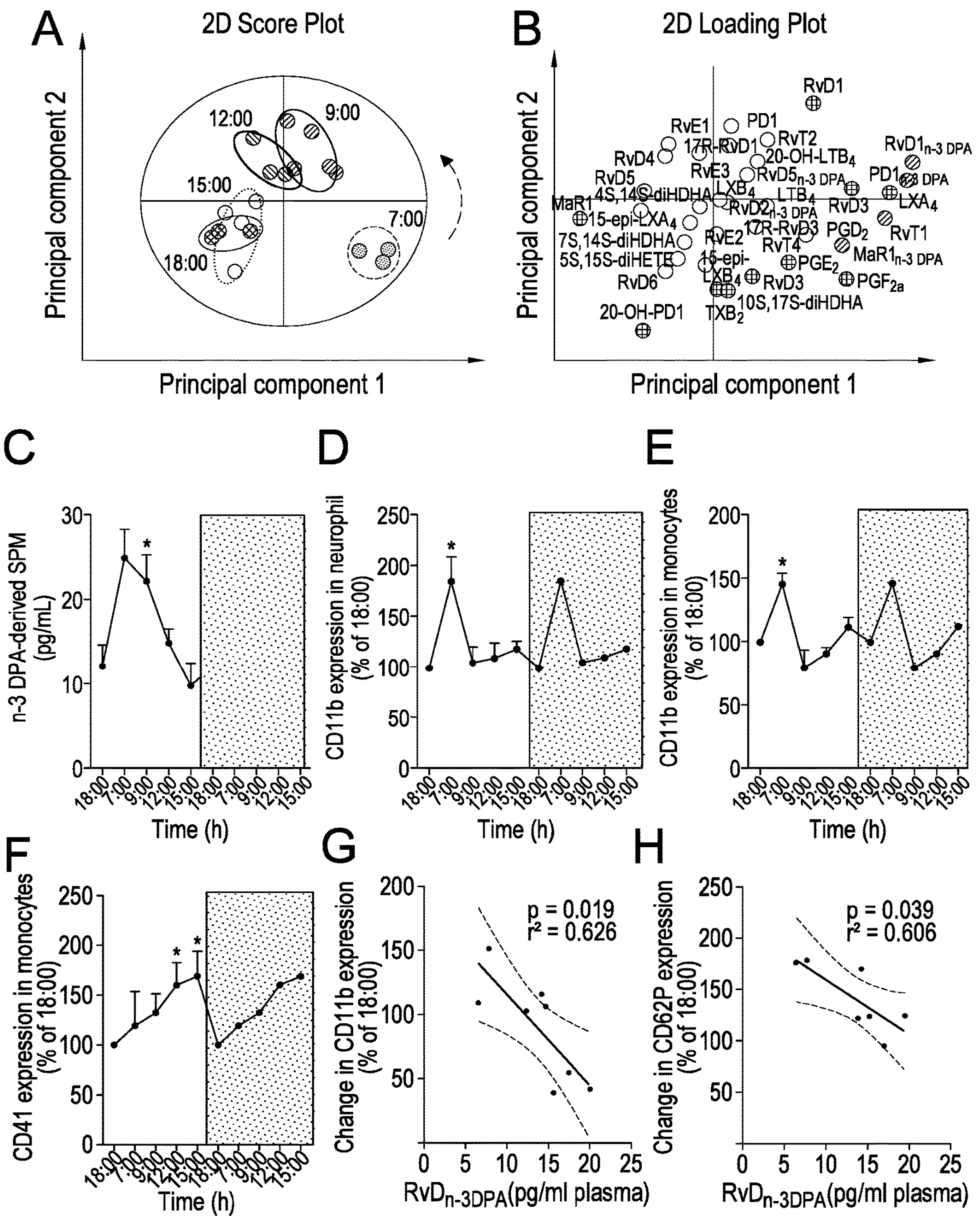

FIG. 20: Vascular n-3 DPA-derived SPM are diurnally regulated in human healthy volunteers. Peripheral blood was collected from healthy volunteers at the indicated intervals and LM concentrations determined using LM profiling (see methods for details). (A) PLS-DA 2-dimensional score plot of the distinct LM-SPM profiles identified human plasma at the indicated intervals and (B) corresponding 2-dimensional loading plot. Grey ellipse in the score plots denotes 95% confidence regions. Grey and blue circles represent LM with a variable in importance score ≥1; n=4 healthy volunteers per interval. (C) n-3 DPA-derived SPM concentrations identified and quantified at each of the time intervals. Results are mean±s.e.m, n=7 per time point and expressed as pg/mL. *, p≤0.05 vs amounts at the 18 h interval using Wilcoxon Signed Rank Test (D) Neutrophil CD11b expression. (E-F) Monocyte (E) CD11b and (F) CD41 expression. Results are mean±s.e.m, n=7 volunteers per interval and expressed as percentage of 18:00 h antigen expression. *p≤0.05 vs 18:00 h interval, determined using Wilcoxon Signed Rank Test. Results in the grey panel are re-plotted from the white portion to aid in visualization of rhythmicity. (G,H) Correlation between changes in monocyte (G) CD11b and (H) CD62P (9:00 to 18:00) expression and 9:00 $RvD_{n\text{-}3\ DPA}$ concentrations. Results are representative of n=8 volunteers. Dashed line represents 95% confidence interval.

Figure 21:
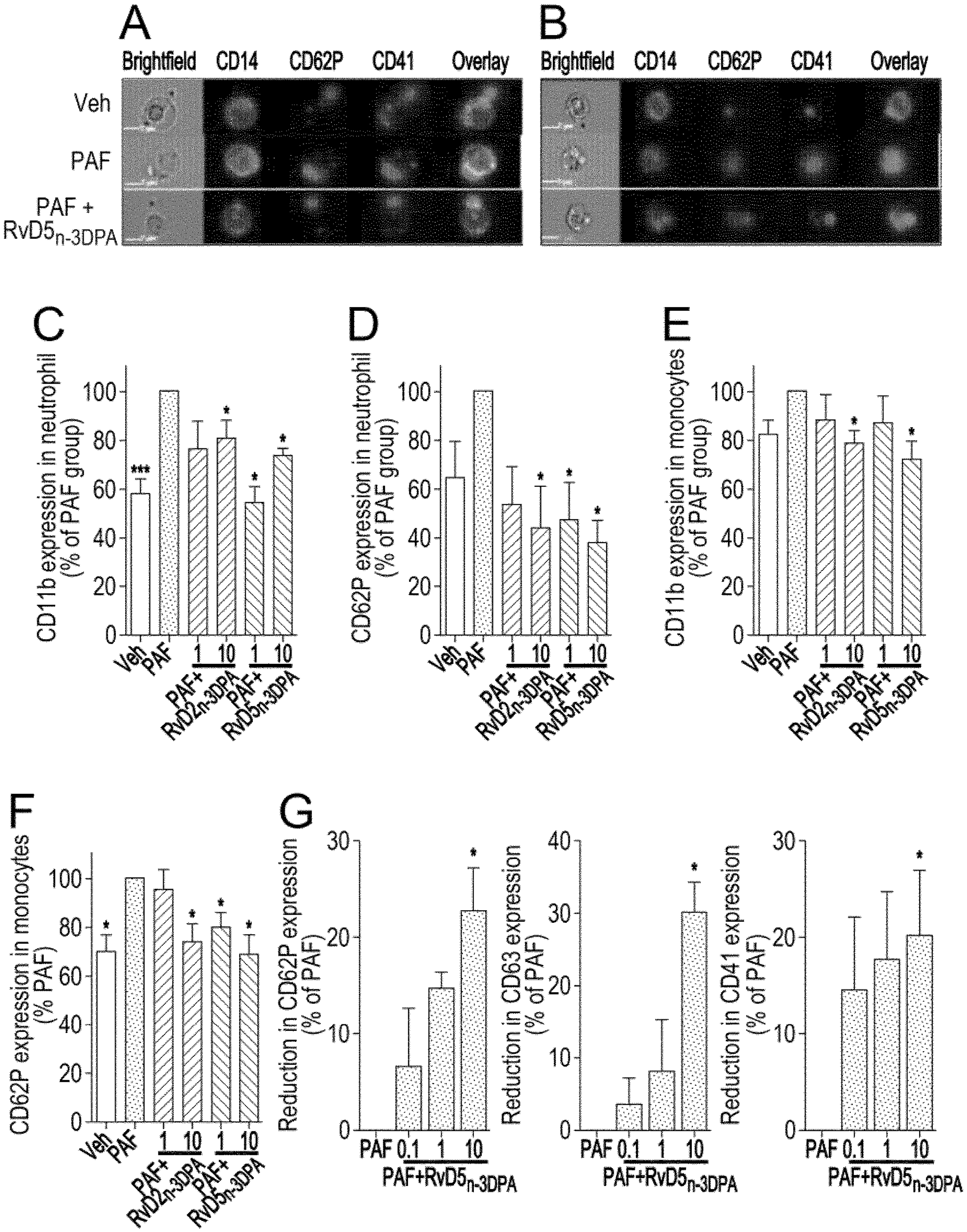

FIG. 21: $RvD2_{n\text{-}3\ DPA}$ and $RvD5_{n\text{-}3\ DPA}$ reduce monocyte, neutrophil and platelet activation in healthy volunteer peripheral blood. Blood was collected from healthy volunteers and incubated with $RvD2_{n\text{-}3\ DPA}$, $RvD5_{n\text{-}3\ DPA}$ (0.1 nM, 1 nM or 10 nM) or vehicle (PBS) for 15 min (37° C.) then with PAF (100 ng/ml; 30 min; 37° C.). Cell activation and leukocyte-platelet aggregates were assessed using flow cytometry. (A,B) Images depicting platelet monocyte (A) and (B) platelet-neutrophil aggregates. Results are representative of n=3 distinct experiments. (C,D) Cumulative neutrophil (C) CD11b and (D) CD62P expression. (E,F) Monocyte (E) CD11b and (F) CD62P expression. Results are mean of n=5 per condition and expressed as percentage change from PAF incubated cells. *p<0.05 compared to PAF using Wilcoxon Signed Rank Test. (G) Platelet rich plasma was incubated with vehicle (PBS) or RvD5$_{n-3\ DPA}$ 0.1-10 nM (15 min; 37° C.) and PAF (100 nM; 30 min; 37° C.). Adhesion molecule expression evaluated using flow cytometry. Results are mean±s.e.m. n=5 healthy volunteers. * p, 0.05 compared to Vehicle group using Friedman's test followed by Dunn's multiple comparisons test.

Figure 22:
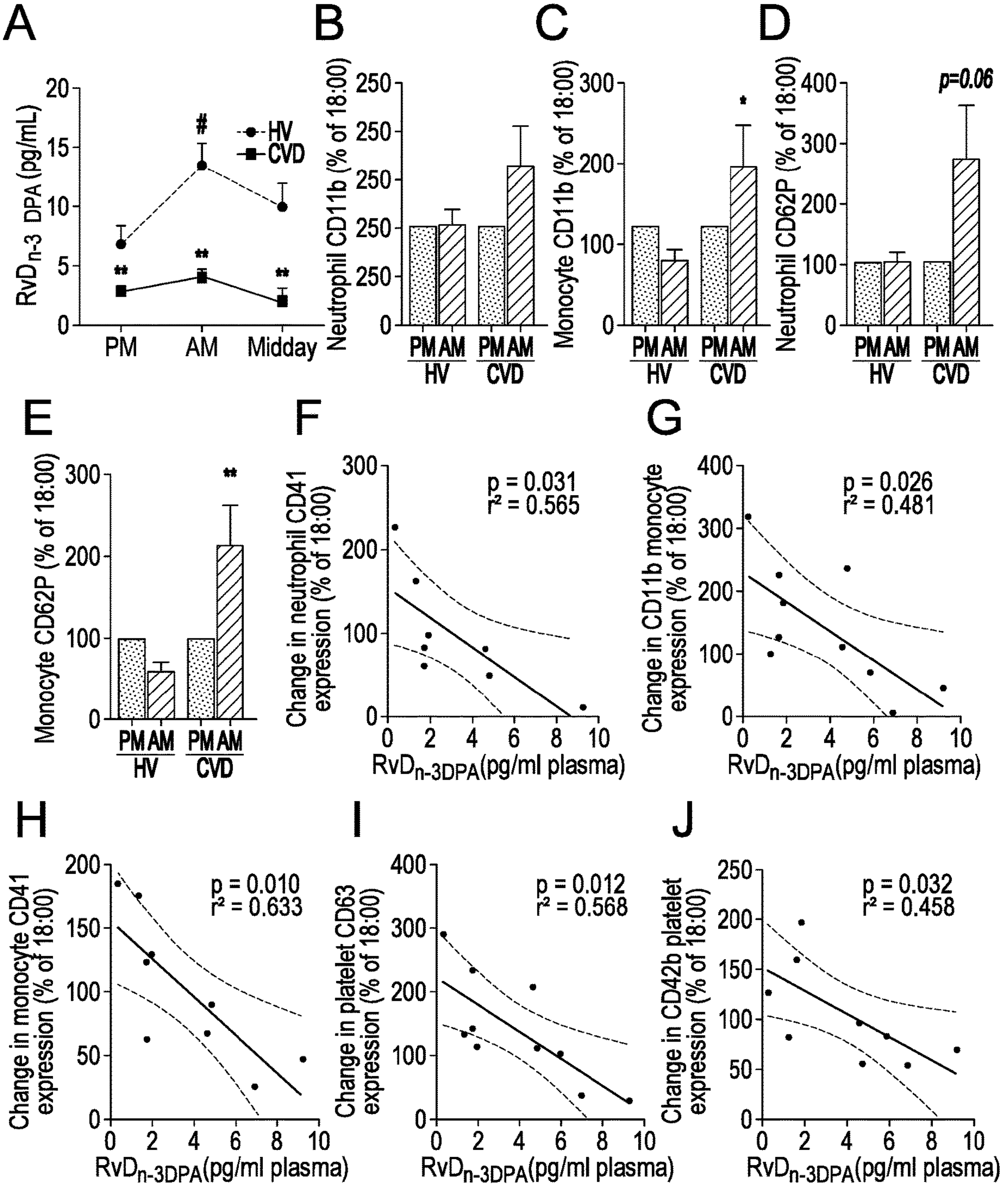

FIG. 22: Systemic n-3 DPA-derived SPM are reduced and leukocyte activation is increased in patients with CVD. Peripheral blood from patients diagnosed with cardiovascular disease (CVD) was collected at 16:00-18:00 h (PM), 9:00 h (AM) and 12:00 (mid-day) LM identified and quantified using LM-profiling (see methods for details). (A) Plasma RvD$_{n-3\ DPA}$ concentrations. Results are mean±s.e.m. and expressed as pg/mL. n=14 CVD patients for AM, PM, 5 Midday and n=7 healthy volunteers (HV). *, p≤0.05 and **, p≤0.01 compared to respective HV group using Mann-Whitney test; # p<0.05 vs PM values using Friedman's test followed by Dunn's multiple comparisons test. (B-E). Whole blood was incubated with fluorescently labeled antibodies and cell activation as well as leukocyte-platelet aggregates were assessed using flow cytometry. (B,C) CD11b expression on (B) neutrophils and (C) monocytes. (D,E) CD62P expression on (D) neutrophils and (E) monocytes. *p<0.05, **p<0.01 compared to HV determined using Wilcoxon Signed Rank Test. n=5 HV and, 9 CVD patients. (F-J) Correlation between percent changes (AM to PM) in (F) neutrophil CD41 (G-H) monocyte (G) CD11b and (H) CD41 and (I-J) platelet (I) CD63 and (J) CD42b expression and 9:00 RvD$_{n-3\ DPA}$ concentrations. Results are representative of n=8-10 patients. Dashed line represents 95% confidence interval.

Figure 23:
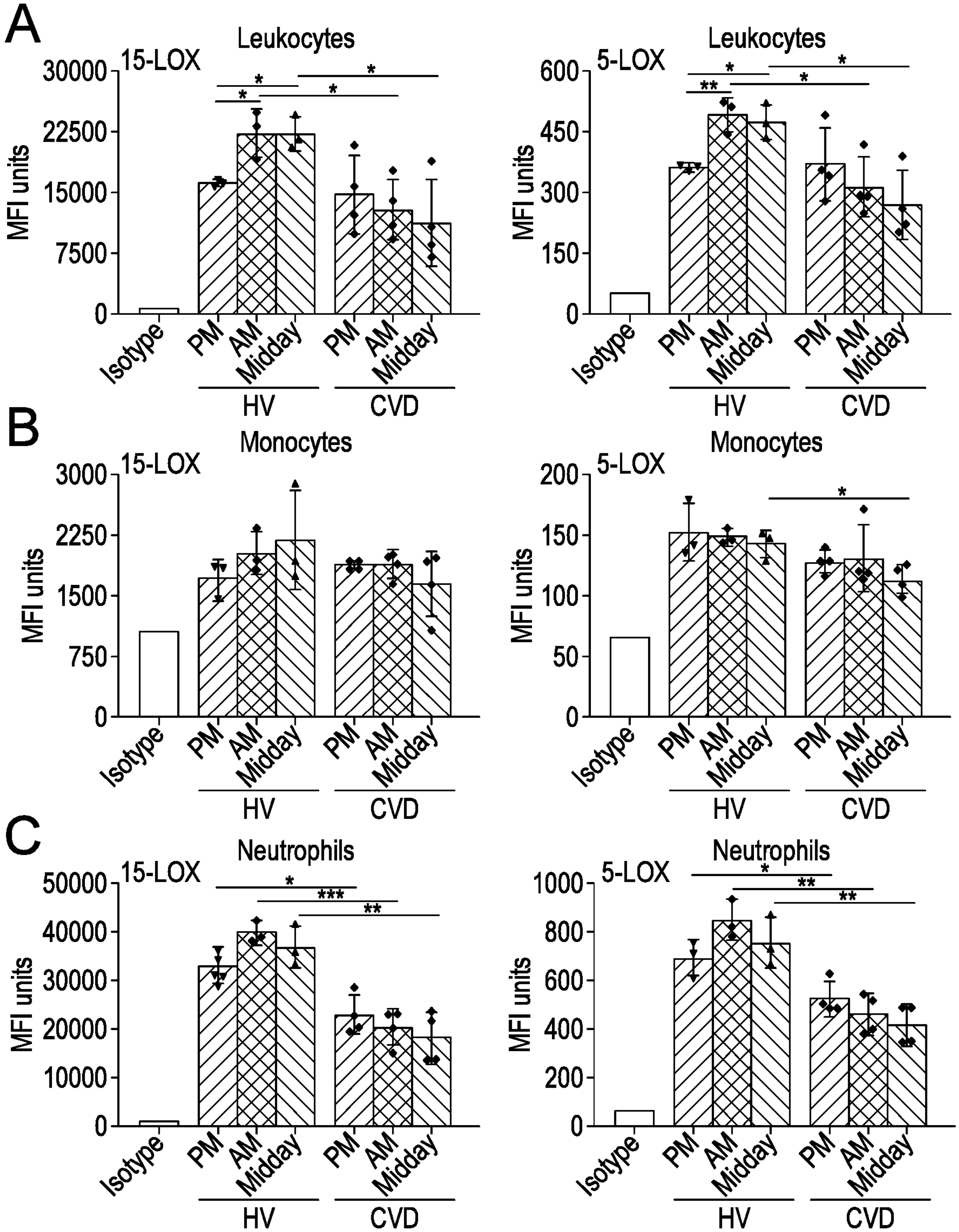

FIG. 23: Dysregulated diurnal regulation of RvD$_{n-3\ DPA}$ biosynthetic enzymes in peripheral blood leukocytes from CVD patients. Peripheral blood from healthy volunteers (HV) and patients diagnosed with cardiovascular disease (CVD) was collected at 9:00 h (AM) and 12:00 h (Midday) and 16:00 h (PM). Leukocyte subsets and biosynthetic enzymes were identified by using fluorescently labeled antibodies and flow cytometry. Expression of 15-LOX and 5-LOX in (A) leukocytes (B) monocytes (C) and neutrophils. Results are mean±s.e.m. and expressed as mean fluorescence intensity units (MFI); n=3 HV, n=4 CVD patients. *, p≤0.05 p<0.01 *p<0.001 compared to HV determined using Unpaired t-test, and 1-way ANOVA with Tukey multiple comparisons test for comparison between AM, Midday and PM groups.

Figure 24:
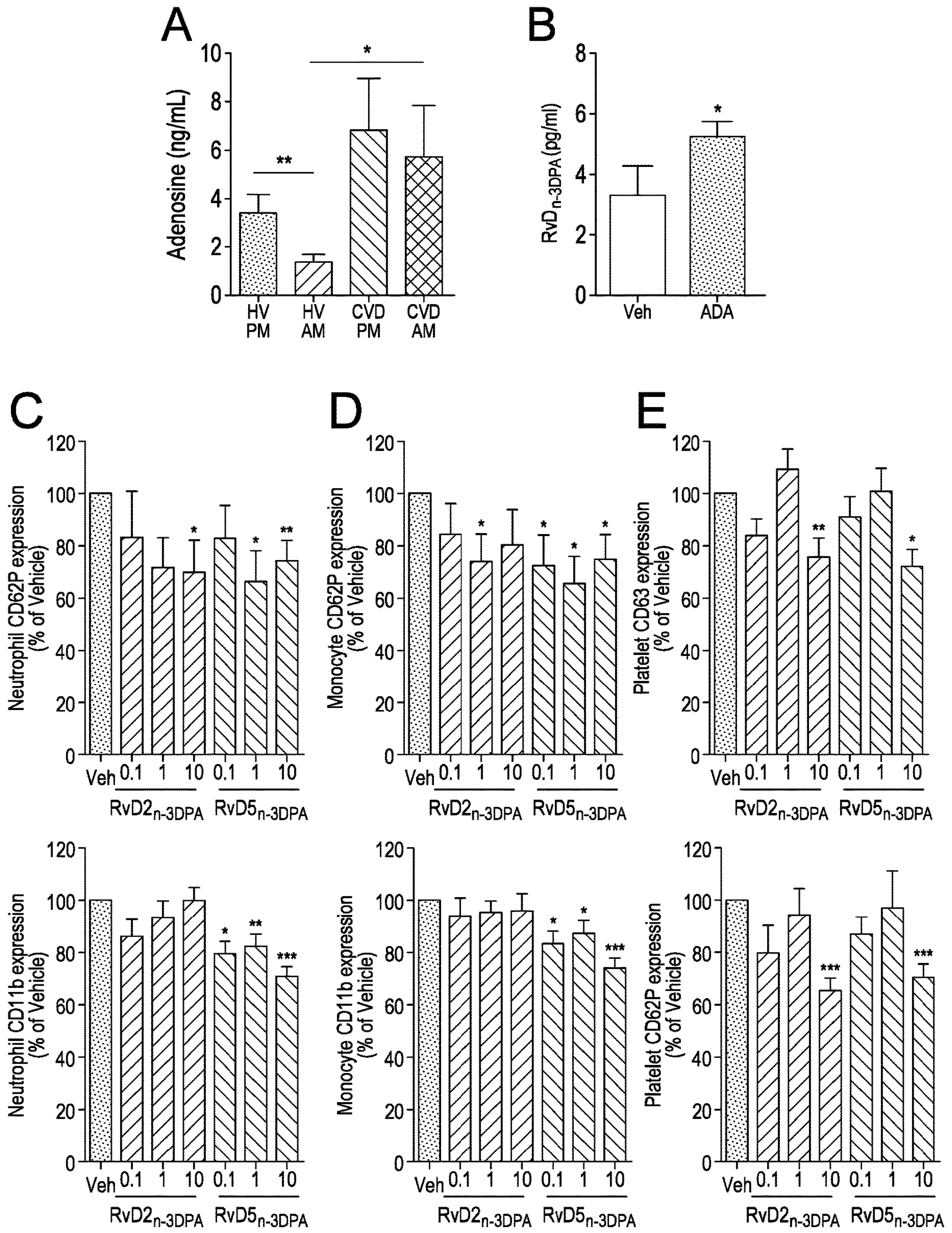

FIG. 24: Increased adenosine downregulates the concentrations of the protective RvD$_{n-3\ DPA}$ in CVD patients. (A) Plasma adenosine concentrations were determined using LC/MS-MS. Results are mean±s.e.m. n=7 HV and, 9 CVD patients. *p<0.05, **p<0.01 using Mann-Whitney Test. (B) Peripheral blood from CVD patients was incubated with ADA (1U; 37° C.; 20 min) then perfused (0.3 Pa, 20 min, 37° C.). Plasma was collected and RvD$_{n-3\ DPA}$ concentrations determined using LC/MS-MS based lipid mediator profiling. Results are mean±s.e.m. n=6 donors. *p<0.05, using paired Mann-Whitney test. (C-E) Whole blood was incubated with RvD2$_{n-3\ DPA}$ or RvD5$_{n-3\ DPA}$ (0.1 nM, 1 nM or 10 nM) or vehicle (PBS containing 0.01% EtOH) for 45 min (37° C.). Expression of (C) neutrophil CD62P and CD11b (D) monocyte CD62P and CD11b and (E) platelet CD63 and CD42P was investigated using flow cytometry and fluorescently labeled antibodies. Results are mean±s.e.m and expressed as percentage of Vehicle (Veh) incubated cells. n=8 patients per interval. * p<0.05 vs Veh group using Wilcoxon Signed Rank Test.

Figure 25:
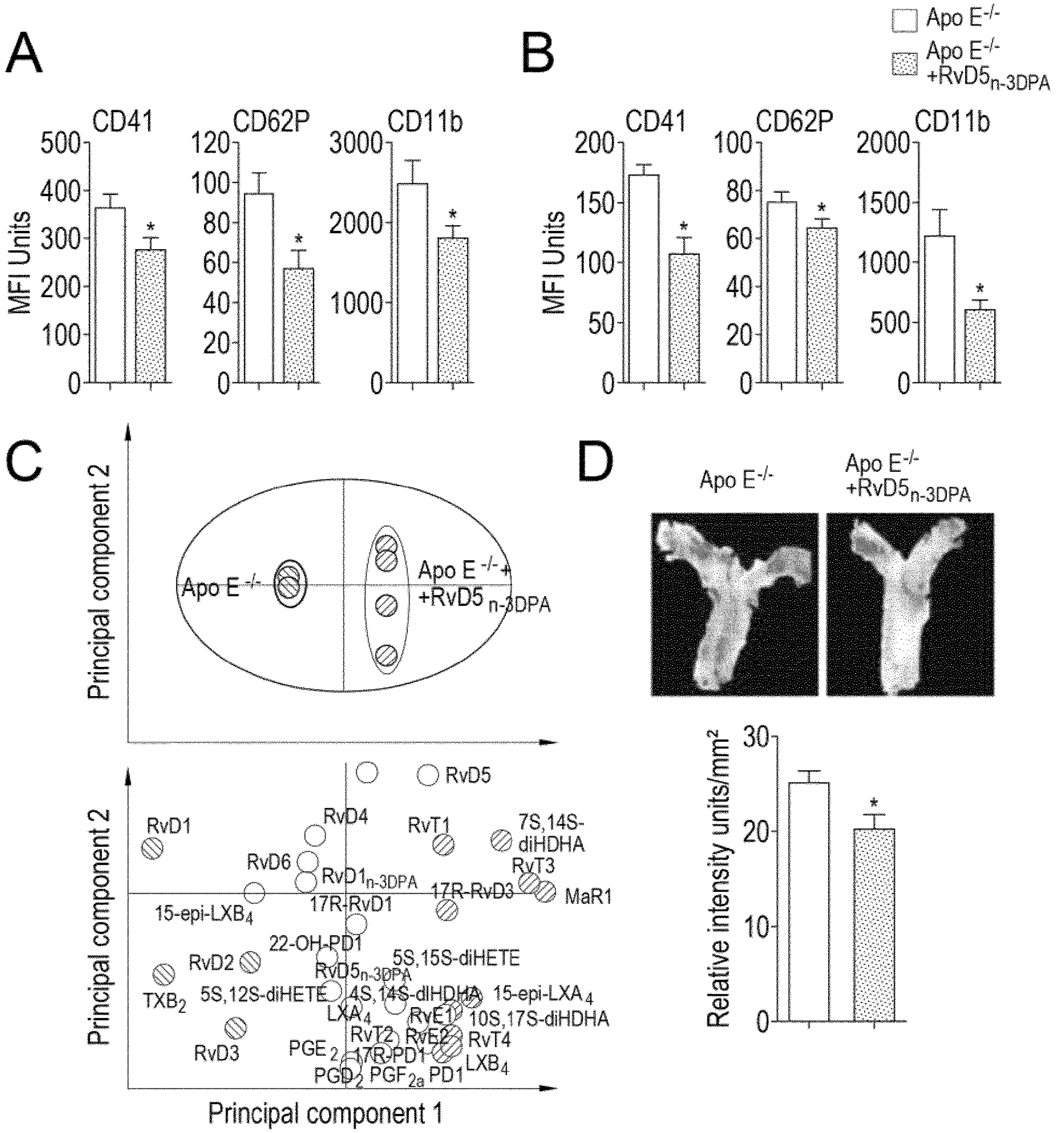

FIG. 25: RvD5$_{n-3\ DPA}$ reduces systemic platelet and leukocyte activation as well as vascular inflammation in ApoE$^{-/-}$ mice. ApoE$^{-/-}$ mice were fed a western diet for 6 weeks and given RvD5$_{n-3\ DPA}$ (100 ng/mouse; i.v.) on alternate days for 2 weeks. Blood was obtained and (A) monocyte (B) neutrophil expression of CD41, CD62P and CD11b were determined using flow cytometry. (C) Descending aortas were harvested lipid mediators were extracted, identified and quantified using LC/MS-MS-based lipid mediator profiling. PLS-DA 2-dimensional score plot of the distinct LM-SPM profiles identified mouse aortic tissues (Top panel) and corresponding 2-dimensional loading plot. Grey ellipse in the score plots denotes 95% confidence regions. Green and blue circles represent LM with a variable in importance score 1 (Bottom panel). (D) Aortic arches were stained using Oil red-O and staining intensity was determined using ImageJ. Results are mean±s.e.m of 4 mice per group. *p<0.05 vs Vehicle treated mice using Mann-Whitney Test.

EXAMPLES

As disclosed in Examples 1 and 9 below, lipid mediator (LM) profiling of plasma from healthy volunteers demonstrated a significant increase in n-3 DPA-derived resolvins (RvD$_{n-3\ DPA}$) between 7 AM and 9 AM. At these time intervals, increases in the expression of monocyte, platelet and neutrophil activation markers were found in healthy volunteer peripheral blood. As disclosed in Example 3 below, patients with cardiovascular disease demonstrated reduced plasma RvD$_{n-3\ DPA}$, a loss in diurnal regulation of these molecules and increases in the activation of circulating platelets, neutrophils and monocytes. Incubation of peripheral blood from these patients with RvD2$_{n-3\ DPA}$ and RvD5$_{n-3\ DPA}$ reduced the expression of specific platelet, monocyte and neutrophil activation markers, as disclosed in Examples 5 and 13 below. Furthermore, as disclosed in Examples 6 and 14 below, administration of RvD5$_{n-3\ DPA}$ to Apolipoprotein E deficient (Apo E)$^{-/-}$ mice reduced systemic leukocyte and platelet activation and protected from vascular disease.

Materials and Methods

Healthy Volunteers Blood Collection

Venous peripheral blood was collected at indicated intervals in sodium citrate (3.2%) from fasting volunteers that declared not taking NSAIDS for at least 14 days, caffeine and alcohol for at least 24 h and fatty fish for 48 h. Blood was collected via sequel bleeds from the same volunteers on the same day. Food was provided after the 12:00 h blood-draw to all volunteers. Volunteers gave written consent in accordance with a Queen Mary Research Ethics Committee (QMREC 2014:61) and the Helsinki declaration. Blood was then taken for flow cytometry and lipid mediator profiling analysis.

CVD Patients' Blood Collection

Fasting patients were screened and those that met the inclusion/exclusion criteria were consented for blood to be obtained between 8:00 to 9:00 h, 12:00 h and between 16:00 to 18:00 h in accordance with East of England-Cambridge Central Research Ethics Committee and the Joint Research Management Office (JRMO), Queen Mary University of London.

The inclusion criteria were i) severe coronary artery disease requiring treatment; ii) hospital admission for percutaneous coronary intervention (PCI); iii) >24 hour post PCI; iv) able to provide informed consent; v) >18 years and vi) at least 2 of the following risk factors: hypertension, high cholesterol, smoker, diabetes, known ischemic heart disease The exclusion criteria were: i) sustained ventricular tachycardia and/or ventricular fibrillation or appropriate ICD valve disease requiring intervention; ii) contra-indications to PCI; iii) women who are pregnant; iv) <18 years and v) enrolled in other studies.

These blood samples were processed within 60 minutes of collection for lipid mediator profiling and whole blood stimulations as detailed below.

Targeted Lipid Mediator Profiling

Plasma was obtained from peripheral blood of healthy volunteers and patients following centrifugation at 1500×g for 10 min at room temperature. Descending aortas were weighed, placed in ice-cold methanol and homogenized using a glass dounce.

All samples for LC-MS-MS-based profiling were extracted using solid-phase extraction columns as described in Dalli et al. 2013 and Rathod et al. 2017, the contents of which are incorporated herein by reference.

Prior to sample extraction, deuterated internal standards, representing each region in the chromatographic analysis (500 pg each) were added to facilitate quantification in 4V of cold methanol.

Samples were kept at −20° C. for a minimum of 45 min to allow protein precipitation.

Supernatants were subjected to solid phase extraction, methyl formate fraction collected, brought to dryness and suspended in phase (methanol/water, 1:1, vol/vol) for injection on a Shimadzu LC-20AD HPLC and a Shimadzu SIL-20AC autoinjector, paired with a triple quadrupole mass spectrometer with or without a linear ion trap.

An Agilent Poroshell 120 EC-C18 column (100 mm×4.6 mm×2.7 μm) was kept at 50° C. and mediators eluted using a mobile phase consisting of methanol-water-acetic acid of 20:80:0.01 (vol/vol/vol) that was ramped to 50:50:0.01 (vol/vol/vol) over 0.5 min and then to 80:20:0.01 (vol/vol/vol) from 2 min to 11 min, maintained till 14.5 min and then rapidly ramped to 98:2:0.01 (vol/vol/vol) for the next 0.1 min. This was subsequently maintained at 98:2:0.01 (vol/vol/vol) for 5.4 min, and the flow rate was maintained at 0.5 ml/min. Mass spectrometer was operated using a multiple reaction monitoring method as in Walker M E et al. 13-Series resolvins mediate the leukocyte-platelet actions of atorvastatin and pravastatin in inflammatory arthritis. *FASEB J.* 2017 August; 31(8):3636-3648, the contents of which are incorporated herein by reference.

Each LM was identified using established criteria including matching retention time to synthetic and authentic materials and at least six diagnostic ions (Walker M E et al. 2017. ibid.)

Calibration curves were obtained for each using synthetic compound mixtures at 0.78, 1.56, 3.12, 6.25, 12.5, 25, 50, 100, and 200 pg that gave linear calibration curves with an $r^2$ values of 0.98-0.99.

Profiling of Acetylcholine, Norepinephrine and Adenosine.

Plasma was placed in ice cold MeOH containing deuterated ($d_9$)-choline and kept at −20° C. for 45 min to allow for protein precipitation. Samples were then centrifuged for 10 minutes at 4000×g. Supernatant were collected and evaporated under a gentle stream of nitrogen gas using a TurboVap LV (Biotage) at 37° C. until dryness. Products were then suspended in MeOH profiled using an LC/MS-MS system. A Qtrap 5500 (AB Sciex) equipped with a Shimadzu SIL-20AC autoinjector and LC-20AD binary pump (Shimadzu Corp.) was used with an Agilent Eclipse Plus C18 column (100×4.6 mm×1.8 μm). The mobile phase consisted of methanol/water/acetic acid, 80:20:0.01 (vol:vol:vol) for 2.5 min that was ramped to 98:2:0.01 (vol:vol:vol) over 0.2 min and maintained for 1.3 min. The flow rate was maintained at 0.5 ml/min. To monitor and quantify the levels of acetylcholine and norepinephrine, the Qtrap 5500 was operated in positive mode and a multiple reaction monitoring (MRM) method was developed with signature ion fragments (m/z) for each molecule monitoring the parent ion (Q1) and a daughter ion (Q3). The MRM transition employed for Acetylcholine was 146>87, for norepinephrine was 170>152 and for adenosine 268>136.

Preparation of $RvD1_{n\text{-}3\ DPA}$ and $RvD2_{n\text{-}3\ DPA}$. $RvD1_{n\text{-}3\ DPA}$ and $RvD2_{n\text{-}3\ DPA}$ were prepared and isolated as described in Dalli J, Colas R A, Serhan C N. Novel n-3 immunoresolvents: structures and actions. *Sci Rep.* 2013; 3:1940, the contents of which are incorporated by reference. n-3 DPA (10 μM) was incubated with 100 U/ml isolated soybean-LOX (Borate buffer, 4° C., pH 9.2). 17S-HpDPA was isolated using UV-RP-HPLC (Infinity 1260; Agilent Technologies). 17S-HpDPA (10 μg) was then incubated with human neutrophils (80×106 cells/ml; $PBS^{+/+}$) and calcium ionophore (5 μM, 37° C.). After 45 min the reaction was quenched using 2 volumes ice-cold methanol, reduced using sodium borohydrate, and products extracted using C18 SPE. $RvD1_{n\text{-}3\ DPA}$ and $RvD2_{n\text{-}3\ DPA}$ were isolated using RP-HPLC (Infinity 1260; Agilent Technologies). Here, an Agilent Poroshell 120 EC-C18 column (100 mm×4.6 mm×2.7 μm) was kept at 50° C. and LM isolated with a mobile phase consisting of methanol-water-acetic acid of 60:40:0.01 (vol/vol/vol) maintained for 2 minutes, then ramped to 80:20:0.01 (vol/vol/vol) from 2 min to 16 min and to 98:2:0.01 (vol/vol/vol) over 3 minutes. This was maintained for 2 min. Flow rate was kept at 0.5 mL/min.

Human Whole Blood Incubations

In Examples 1 and 9 below, venous blood from healthy volunteers was collected and incubated with acetylcholine (ACh) at 0.1 μM for 45 min (37° C.) Plasma was then separated by centrifugation at 1,500×g for 10 min for LM profiling.

In Examples 3, 5, 11 and 13 below, whole blood was incubated with $RvD1_{n\text{-}3\ DPA}$, $RvD2_{n\text{-}3\ DPA}$, $RvD5_{n\text{-}3\ DPA}$ (0.1, 1, 10 nM) or vehicle (PBS) for 15 min (37° C.) Blood was then incubated with PAF (100 nM) for 30 min (37° C.). After stimulation, samples were washed twice with PBS for 12 min at 800×g. Samples were stained for flow cytometry as described below.

Flow Chamber:

Using an automated syringe pump (Harvard Apparatus) connected to small-diameter tubing (1.6 mm inner diameter) and chamber slides (15μ-Slide $VI^{0.4}$, Ibidi), whole blood was perfused at a sheer rate of 0.1 dyne/$cm^2$ (low sheer rate) and at 0.3 dyne/$cm^2$ (high sheer rate) for 15 min. In selected experiment, blood was incubated with 10 nM Ach or 1 u of ADA for 20 min prior perfusing.

PRP Incubations:

Peripheral blood from healthy volunteers was collected in acidified-citrate-dextrose. Blood was centrifuged at 500×g for 20 min. PRP was collected and cells incubated with $RvD5_{n\text{-}3\ DPA}$ or vehicle (0.01% EtOH+PBS) for 15 min at 37° C. Cells were then incubated with PAF (100 nM) or Vehicle (0.01% EtOH) for 30 min at 37° C. Cells were then washed with PBS and cellular activation was assessed using flow cytometry as detailed below.

Apo $E^{-/-}$ Mice

Experiments described in Examples 6 and 14 below strictly adhered to UK Home Office regulations (Guidance on the Operation of Animals, Scientific Procedures Act, 1986) and Laboratory Animal Science Association (LASA) Guidelines (Guiding Principles on Good Practice for Animal Welfare and Ethical Review Bodies, 3rd Edition, 2015). Apo $E^{-/-}$ mice were a kind gift from Prof Fulvio D'Acquisto (Queen Mary University of London).

Mice (male and female) were fed a western diet for 6 weeks from 4 weeks of age and kept of a 12 h light dark cycle. At 8 weeks of age, mice were given $RvD5_{n\text{-}3\ DPA}$ (100 ng/mouse; i.v.) or vehicle on alternate days for a 2-week period. Mice were culled, aortic arches were collected and stained using oil-red O as in Khambata R S et al. Anti-inflammatory actions of inorganic nitrate stabilize the atherosclerotic plaque. *Proc Natt Acad Sci USA*. 2017; 114(4): E550-E559, the contents of which are incorporated herein by reference. Staining intensity was determined using image processing software and expressed as relative units per $mm^2$. The descending aorta was collected, placed in ice-cold methanol and lipid mediators identified and quantified as described above.

Flow Cytometry

Whole blood was incubated with lineage-specific markers for 45 min (4° C., in DPBS containing 0.02% BSA). The following anti-human antibodies were used: VioBlue-anti-CD41, PE-Cy5-anti-CD62P, Brilliant Violet 711-anti-CD11b, APC-Cy7-anti-CD16, Alexa Fluor 647-anti-CD14. After staining, red blood cells were lysed using Whole Blood Lysing Reagent Kit, according to the manufacturer's instructions. Data was collected using a flow cytometer and analysis was conducted using appropriate software.

In separate experiments blood was collected from Apo $E^{-/-}$ mice using heparin-lined syringes via cardiac puncture. Cells were incubated with Fc-blocking IgG and anti-mouse CD11b-PE-Texas Red, CD62P-Brilliant Violet650™, CD115-Brilliant Violet 711™, and CD41-Brilliant Violet 510™ (Biolegend). for 45 minutes on ice. Red blood cells were lysed and fixed using Whole Blood Lysing Reagent Kit. Staining was then evaluated using a flow cytometer and analysis was conducted using appropriate software.

For the analysis of the biosynthetic enzymes, whole blood was incubated with lineage-specific markers for 30 min (4° C., in DPBS containing 0.02% BSA). The following anti-human antibodies were used: Brilliant Violet 786-anti-CD14, APC-Cy7-anti-CD16, PerCP-Cy5.5-anti-CD4. After staining, red blood cells were lysed using Whole Blood Lysing Reagent Kit, according to the manufacturer's instructions. Samples were washed twice with PBS for 12 min at 800×g, and incubated with Fc block for 20 min at RT (dilution 1:2, in Permeabilization buffer). Next followed the intracellular staining for 30 min (RT, in Permeabilization buffer). The following anti-human antibodies were used: Alexa Fluor 647-anti-15-LOX, Dylight 405-anti-5-LOX. Staining was then evaluated using LSRFortessa cell analyser (BD Biosciences) and analysed using FlowJo software (Tree Star Inc., V10).

In select experiments platelet adhesion molecule expression was assessed. Here platelets were incubated with fluorescently labelled mouse anti-human VioBlue-anti-CD41, PE-Cy5-anti-CD62P, PerCP/Cy5.5-anti-CD63 and FITC-ant-CD42b for 30 min at 4° C. Cells were then washed and fluorescence, staining evaluated using LSRFortessa cell analyser (BD Biosciences) and analysed using FlowJo software (Tree Star Inc., V10).

ImageStream.

Whole blood was incubated with lineage-specific markers for 45 min (4° C., in DPBS containing 0.02% BSA). The following anti-human antibodies were used: eFluor450-anti-CD41, PE-Cy5-anti-CD62P, APC-Cy7-anti-CD16, FITC-anti-CD14. After staining, red blood cells were lysed using Whole Blood Lysing Reagent Kit, according to the manufacturer's instructions. Staining was then assessed using ImageStream X MK2 and analysis was performed using IDEAS® (Image Data Exploration and Analysis Software, Version 6.0).

Statistical Analysis

Results are expressed as mean±s.e.m. Normality and equal distribution of variance between the different groups analysed were assumed. Sample sizes for each experiment were determined on the variability observed in preliminary experiments. Differences between groups were assessed using one-sample t test (normalized data), Student's t test (2 groups), 1-way ANOVA (multiple groups) followed by post hoc Dunnett's test. Investigators were not blinded to group allocation or outcome assessment. The criterion for statistical significance was $p \leq 0.05$. Sample sizes for each experiment were determined on the variability observed in prior experiments (Rathod K S et al. 2017) and preliminary experiments. Partial least squares-discrimination analysis (PLS-DA) and principal component analysis (PCA)19 were performed using SIMCA 14.1 software (Umetrics, Umea, Sweden) following mean centering and unit variance scaling of LM levels. PLS-DA is based on a linear multivariate model that identifies variables that contribute to class separation of observations (Blister exudates) on the basis of their variables (LM levels). During classification, observations were projected onto their respective class model. The score plot illustrates the systematic clusters among the observations (closer plots presenting higher similarity in the data matrix). Loading plot interpretation identified the variables with the best discriminatory power (Variable Importance in Projection greater then 1) that were associated with the distinct intervals and contributed to the tight clusters observed in the Score plot.

Results

Example 1: Diurnal Changes in Peripheral Blood n-3 DPA-Derived SPM are Regulated by Acetylcholine To investigate whether peripheral blood SPM concentrations are diurnally regulated, plasma was obtained from healthy volunteers at distinct intervals during a 24 h period (see Table 4 below for demographics).

TABLE 4

| Healthy volunteers' demographics | | | |
|---|---|---|---|
| Sex | Age (years) | Weight (Kg) | BMI (Kg/$m^2$) |
| 3M/4F | 34 ± 4.1 | 65.6 ± 11.3 | 23.2 ± 3.0 |

LM were then extracted using C18 solid phase extraction and identified and quantified using liquid chromatography-tandem mass spectrometry (LC/MS-MS).

In plasma from healthy volunteers, mediators from all four major essential fatty acid metabolomes were identified, including the EPA derived E-series resolvins, n-3 DPA-derived resolvins and protectins, DHA-derived protectins and maresins and the arachidonic acid (AA)-derived prostaglandins and leukotrienes (see FIG. 1A).

These mediators were identified in accordance with published criteria that include matching retention time in liquid chromatography and at least six diagnostic ions in the tandem mass spectrum (Dalli et al. 2013) as illustrated for $RvD5_{n\text{-}3\ DPA}$ (FIG. 1B). Multivariate analysis of plasma lipid mediator profiles demonstrated a diurnal shift in plasma LM-SPM concentrations with a leftward shift in LM-SPM clusters from morning to evening profiles (FIGS. 1C and 1D). This shift was associated with an increase in the amounts of n-3 DPA derived mediators, including $RvD1_{n\text{-}3\ DPA}$ and $RvD5_{n\text{-}3\ DPA}$, from the evening (18:00 h) to morning intervals (7:00 and 9:00 h) as well as increases in the inflammatory eicosanoids $PGF_{2\alpha}$ (see FIG. 1E, FIG. 2 and Table 6 below).

Retention times for $RvD1_{n\text{-}3\ DPA}$, $RvD2_{n\text{-}3\ DPA}$ and $RvD5_{n\text{-}3\ DPA}$ are disclosed above in Table 3.

Diagnostic ions for $RvD1_{n\text{-}3\ DPA}$, $RvD2_{n\text{-}3\ DPA}$ and $RvD5_{n\text{-}3\ DPA}$ are disclosed in Table 5 below.

TABLE 5

| Diagnostic ions for $RvD1_{n\text{-}3\ DPA}$, $RvD2_{n\text{-}3\ DPA}$ and $RvD5_{n\text{-}3\ DPA}$<br>$RvD_{n\text{-}3\ DPA}$ Fragmentation pattern ions (m/z) |
|---|
| 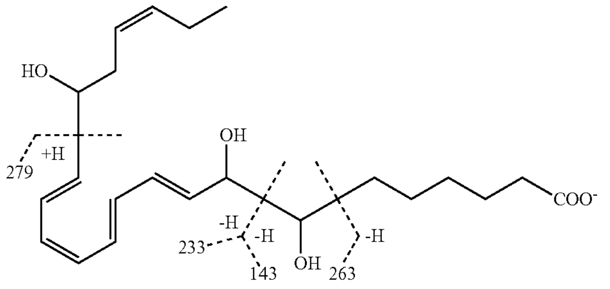<br>$RvD1_{n\text{-}3\ DPA}$<br>m/z 375, m/z 359, m/z 341, m/z 333, m/z 315, m/z 297, m/z 289, m/z 261, m/z 233, m/z 215, m/z 197, m/z 143 and m/z 125 |
| 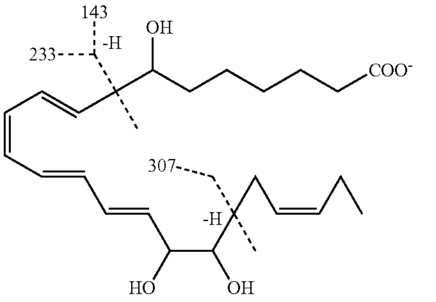<br>$RvD2_{n\text{-}3\ DPA}$<br>m/z 375, m/z 359, m/z 341, m/z 333, m/z 315, m/z 307, m/z 297, m/z 289, m/z 261, m/z 233, m/z 215, m/z 143 and m/z 125 |
| 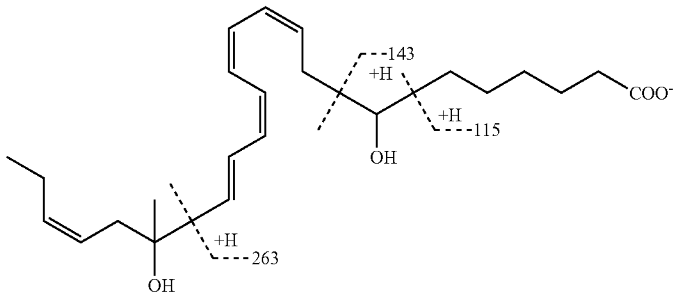<br>$RvD5_{n\text{-}3\ DPA}$<br>m/z 361, m/z 343, m/z 325, m/z 299, m/z 281, m/z 263, m/z 228, m/z 201, m/z 199, m/z 143 |

TABLE 6

| Diurnal lipid mediator profiles in healthy volunteer peripheral blood. | |
|---|---|
| | Healthy volunteer plasma |
| DHA bioactive | Lipid mediators' concentration (pg/mL) |

Diurnal changes were also found in plasma Thromboxane ($TxB_2$), the inactive further metabolite of the potent platelet agonist $TxA_2$ (Samuelsson B. Role of basic science in the development of new medicines: examples from the eicosanoid field. *J Biol Chem.* 2012; 287(13):10070-10080) (see Table 6 above). Of note, concentrations of n-3 DPA derived SPM were within their reported bioactive ranges (Serhan C N. 2017; Arnardottir H H et al. Resolvin D3 Is Dysregulated in Arthritis and Reduces Arthritic Inflammation. *J Immunol.* 2016; 197(6):2362-2368) suggesting that they may be involved in regulating vascular responses.

The mechanism(s) by which peripheral blood n-3 DPA derived SPM may be regulated were investigated. Since, as mentioned above, it has been found that acetylcholine (ACh) regulates SPM production in leukocytes, it was assessed whether peripheral blood levels of this neurotransmitter were diurnally regulated. Here it was found that plasma ACh concentrations mirrored those of the $RvD_{n\text{-}3\ DPA}$ reaching a maximum at 7:00 h (see FIG. 3A), suggesting that ACh may also regulate the $RvD_{n\text{-}3\ DPA}$ in peripheral blood.

To test this, whole blood was incubated with ACh, and the n-3 DPA SPM concentrations were investigated using lipid mediator profiling. In these, whole blood incubations mediators from all four n-3 DPA mediator families were identified in accordance with published criteria (FIGS. 3B and 3C and Table 7 below).

TABLE 7

ACh regulation of n-3 DPA metabolome in human whole blood.

| n-3 DPA bioactive metabolome | Q1 | Q3 | Lipid mediators concentration (pg/mL) Vehicle | | | ACh 0.1 μM | | |
|---|---|---|---|---|---|---|---|---|
| $RvD1_{n\text{-}3\ DPA}$ | 377 | 143 | 3.4 | ± | 1.8 | 4.9 | ± | 2.8 |
| $RvD2_{n\text{-}3\ DPA}$ | 377 | 261 | 2.8 | ± | 1.2 | 7.4 | ± | 2.6* |
| $RvD5_{n\text{-}3\ DPA}$ | 361 | 201 | 0.8 | ± | 0.7 | 1.5 | ± | 0.6 |
| $PD1_{n\text{-}3\ DPA}$ | 361 | 155 | 0.4 | ± | 0.2 | 0.5 | ± | 0.1 |
| $MaR1_{n\text{-}3\ DPA}$ | 361 | 223 | 0.3 | ± | 0.2 | 0.9 | ± | 0.3* |
| RvT1 | 377 | 211 | 0.3 | ± | 0.3 | 2.0 | ± | 1.3 |
| RvT2 | 377 | 197 | 1.2 | ± | 0.8 | 1.6 | ± | 0.9 |
| RvT3 | 377 | 255 | 1.2 | ± | 0.9 | 1.4 | ± | 0.9 |
| RvT4 | 359 | 211 | 0.5 | ± | 0.3 | 1.0 | ± | 0.4 |
| 17-HDPA | 345 | 247 | 64.4 | ± | 14.9 | 58.9 | ± | 13.2 |
| 14-HDPA | 345 | 207 | 112.6 | ± | 25.5 | 137.2 | ± | 25.8* |
| 13-HDPA | 345 | 195 | 1.4 | ± | 0.4 | 1.9 | ± | 0.6* |
| 7-HDPA | 345 | 143 | 56.4 | ± | 19.3 | 44.9 | ± | 10.7 |
| DPA | 329 | 285 | 3703.3 | ± | 703.0 | 3873.1 | ± | 706.3 |

Peripheral blood from healthy volunteers was collected and incubated with ACh (0.1, 1 or 10 μM; 45 min; 37° C.) Incubations were quenched with ice-cold methanol and n-3 DPA-derived LM identified and quantified using LM-profiling (see methods described above for details). Q1, M-H (parent ion) and Q3, diagnostic ion in the MS-MS (daughter ion). Results are expressed as pg/mL, mean ± s.e.m, n = 9 donors per group. – = below limits of detection; detection limit = ~0.1 pg.

Quantitation of the identified molecules demonstrated increases in $RvD_{n\text{-}3\ DPA}$ (FIG. 3D, Table 7) with a ~160% increase in $RvD2_{n\text{-}3\ DPA}$ when compared with concentrations found in blood incubated with vehicle alone. Of note, incubation of peripheral blood with norepinephrine, another neurotransmitter that is diurnally regulated in the circulation (Shea S A et al. Existence of an endogenous circadian blood pressure rhythm in humans that peaks in the evening. *Circ Res.* 2011; 108(8):980-984) (n=7 volunteers), did not significantly augment the production of n-3 DPA derived mediators (n=9 healthy volunteers; 0.1-10 μM). These results suggest that ACh controls the diurnal changes in peripheral blood $RvD_{n\text{-}3\ DPA}$.

Example 2: Circadian Regulation of Systemic Leukocyte and Platelet Activation

Having found diurnal changes in peripheral blood LM-SPM levels and given the potent actions that $RvD_{n\text{-}3\ DPA}$ exert on leukocyte and platelet function (Dalli et al. 2013; Gobbetti T et al. Protectin $D1_{n\text{-}3\ DPA}$ and resolvin $D5_{n\text{-}3\ DPA}$ are effectors of intestinal protection. *Proc Natl Acad Sci USA.* 2017; 114(15):3963-3968) it was investigated whether this reflected changes in leukocyte and platelet activation. Flow cytometric analysis of peripheral blood cells demonstrated significant increases in neutrophil CD11b expression as well as an increase in platelet-neutrophil aggregates, measured as increases in the expression of CD41 (Shinohara M, et al. 2014) on peripheral blood neutrophils (FIGS. 4A and 4B). Increases in CD11b and CD41 expression on circulating monocytes were also found at the 9:00 h interval compared with the 18:00 h interval (FIGS. 4C and 4D). These results demonstrate a circadian regulation of leukocyte and platelet activation that reaches a maximum between 7:00 and 9:00 h that is coincident with $RvD_{n\text{-}3\ DPA}$ concentrations.

Example 3: $RvD_{n\text{-}3\ DPA}$ Reduce Leukocyte and Platelet Activation in Peripheral Blood The actions of $RvD_{n\text{-}3\ DPA}$ in regulating monocyte, neutrophil and platelet activation as well as platelet-leukocyte aggregates were investigated in light of their pathogenic functions in cardiovascular disease (Furman M I et al. 2001; Pfluecke C et al. 2016; Huo Y et al. 2003). For this purpose, human peripheral blood was incubated with platelet activating factor (PAF) in the presence or absence of $RvD_{n\text{-}3\ DPA}$, given PAF's role in propagating vascular inflammation (Palur Ramakrishnan A V et al. 2017).

The expression of activation markers on peripheral blood cells was assessed using flow cytometry. Incubation of human peripheral blood with $RvD2_{n\text{-}3\ DPA}$ led to dose dependent decreases in neutrophil CD11b expression and in the amounts of neutrophil-platelet aggregates measured as decreases in neutrophil CD62P (FIGS. 5A-D) and CD41 expression (n=5 donors; ~20% decrease at 10 nM) when compared with cells incubated with PAF alone. In these incubations, a significant reduction in monocyte activation was found where $RvD2_{n\text{-}3\ DPA}$, gave dose dependent decreases in monocyte expression of CD11b, and the platelet markers CD62P (FIGS. 5E and 5F) and CD41 (n=5 donors; ~29% decreased at 10 nM).

Similar findings were also made when healthy volunteer whole blood was incubated with $RvD5_{n\text{-}3\ DPA}$ that resulted in dose-dependent decreases in neutrophil and monocyte CD11b expression as well as in leukocyte-platelet aggregates (see FIG. 5).

$RvD1_{n\text{-}3\ DPA}$ was also found partially to regulate neutrophil, monocyte and platelet responses (n=5 donors).

These data suggest that each of the $RvD_{n\text{-}3\ DPA}$ displays specific biological actions in regulating vascular leukocyte and platelet responses.

These findings also suggest that the observed increases in peripheral blood n-3 DPA SPM in the morning hours (FIGS. 1 and 2 and Table 6 above) may form part of an endogenous protective program to counter-regulate diurnal leukocyte and platelet activation.

Example 4: Reduced $RvD_{n\text{-}3\ DPA}$ and Increased Systemic Inflammation in Peripheral Blood from Patients with Cardiovascular Disease It was investigated whether results obtained with healthy volunteers were translatable to the clinical setting. Given that $RvD_{n\text{-}3\ DPA}$ increased during the early morning hours, a time window associated with higher incidence of myocardial infarct (Nakashima H et al. Impact of Morning Onset on the Incidence of Recurrent Acute Coronary Syndrome and Progression of Coronary Atherosclerosis in Acute Myocardial Infarction. *Circ J.* 2017; 81(3):361-367; Muller J E et al. Circadian variation in the frequency of onset of acute myocardial infarction. *N Engl J Med.* 1985; 313(21):1315-1322) the peripheral blood levels of $RvD_{n\text{-}3\ DPA}$ in patients with cardiovascular diseases (CVD) that were also at an increased risk of myocardial infarct were investigated (see Table 8 below for details and methods for risk criteria).

TABLE 8

| CVD-demographics and clinical data | |
|---|---|
| Participants | 9 |
| Age (years) | 65.2 ± 8.6 |
| Sex | 7 Male, 2 Female |
| CRP mg/L | 35.4 ± 42.2 |
| IL-6 pg/mL | 2.5 ± 1.0 |
| TNF-α pg/mL | 108.2 ± 74.9 |
| Creatine μmol/L | 119.1 ± 90.5 |
| LDL mmol/L | 3.0 ± 0.2 |
| HDL mmol/L | 0.5 ± 0.1 |
| Type II Diabetes | 3 |
| Hypertension | 9 |
| Current Smoking | 0 |
| Obese n | 4 |
| Previous AMI | 1 |
| Previous PCI | 4 |
| LVEF ≤ 50% | 4 |
| Aspirin (n) | 9 |
| Statins (n) | Atorvastatin (4), Simvastatin (3) and Rosuvastatin (1) |
| Other medications (n) | Allopurinol (1), Amitriptyline (2), Amlodipine (2), Apixaban (1), Bisoprolol (6), Candesartan (1), Citalopram (1), Clopidogrel (2), Codeine (1), Cyanacobalamin (1), Dorzolamide (1), Doxazosin (2), Enoxaparin (1), Fentanyl (1), Finasteride (1), Flucloxacillin (1), Fluoxetine (2), Furosemide (2), Isosorbide mononitrate (1), Lansoprazole (4), Lantus Insulin (1), Lisinopril (1), Metformin (1), Nicorandil (1), NoroRapid Insulin (1), Omeprazole (3), Paracetamol (1), Phyllocontine (1), Priadel (1), Ramipril (5), Salbutamol (1), Salmeterol (1), Sertraline (1), Setagliptin (1), Tamoxifen (1), Tamsulosin (2) Temazepam (1), Thiamine (1), Tildiem (1), Timolol (1), Tioropium bromide (1), Warfarin (1), Xalatan (1). |

Using lipid mediator profiling, three $RvD_{n\text{-}3\ DPA}$, including $RvD5_{n\text{-}3\ DPA}$ (FIGS. 6A and 6B) as well as mediators from the DHA, EPA and AA metabolomes including the D-series resolvins and the prostaglandins (see Table 9 below) were identified in patient peripheral blood.

TABLE 9

Peripheral blood LM profiles in patients with CVD.

| DHA bioactive metabolome | Q1 | Q3 | Plasma from CVD patients Lipid mediators concentration (pg/mL) AM | PM |
|---|---|---|---|---|
| RvD1 | 375 | 141 | 0.8 ± 0.8 | 0.8 ± 0.7 |
| RvD2 | 375 | 141 | 0.2 ± 0.2 | – |
| RvD3 | 375 | 147 | 0.5 ± 0.3 | 0.1 ± 0.0 |
| RvD4 | 375 | 101 | 2.8 ± 1.9 | 1.6 ± 0.7 |
| RvD5 | 359 | 199 | 2.7 ± 1.3 | 1.8 ± 0.6 |
| RvD6 | 359 | 101 | 0.2 ± 0.1 | 0.4 ± 0.3 |
| 17R-RvD1 | 375 | 141 | 0.1 ± 0.1 | – |
| 17R-RvD3 | 375 | 147 | – | – |
| PD1 | 359 | 153 | 0.7 ± 0.2 | 0.5 ± 0.2 |
| 17R-PD1 | 359 | 153 | 0.0 ± 0.0 | 0.5 ± 0.5 |
| 10S,17S-diHDHA | 359 | 153 | 0.1 ± 0.1 | 0.5 ± 0.2 |
| 22-OH-PD1 | 375 | 153 | 0.1 ± 0.1 | 3.5 ± 3.7 |
| MaR1 | 359 | 221 | 0.6 ± 0.5 | 0.1 ± 0.1 |
| 7S,14S-diHDHA | 359 | 221 | 1.2 ± 0.7 | 0.3 ± 0.3 |
| 4S,14S-diHDHA | 359 | 159 | 0.5 ± 0.3 | 0.1 ± 0.1 |
| n-3 DPA bioactive metabolome | | | | |
| $RvD1_{n\text{-}3\ DPA}$ | 377 | 215 | 1.8 ± 0.6 | 1.0 ± 0.4 |
| $RvD2_{n\text{-}3\ DPA}$ | 377 | 261 | 2.2 ± 0.9 | 1.2 ± 0.6 |

TABLE 9-continued

Peripheral blood LM profiles in patients with CVD.

| DHA bioactive metabolome | Q1 | Q3 | Plasma from CVD patients Lipid mediators concentration (pg/mL) AM | | | | | |
|---|---|---|---|---|---|---|---|---|
| | | | AM | | | PM | | |
| $RvD5_{n\text{-}3\ DPA}$ | 361 | 263 | 0.2 | ± | 0.2 | 0.6 | ± | 0.3 |
| $PD1_{n\text{-}3\ DPA}$ | 361 | 183 | 0.3 | ± | 0.1 | 0.2 | ± | 0.1 |
| $MaR1_{n\text{-}3\ DPA}$ | 361 | 249 | | – | | | – | |

TABLE 9-continued

Peripheral blood LM profiles in patients with CVD.

| DHA bioactive metabolome | Q1 | Q3 | Plasma from CVD patients Lipid mediators concentration (pg/mL) | | | | | |
|---|---|---|---|---|---|---|---|---|
| | | | AM | | | PM | | |
| RvT1 | 377 | 193 | 0.4 | ± | 0.3 | 0.1 | ± | 0.0 |
| RvT2 | 377 | 233 | 0.5 | ± | 0.3 | | – | |
| RvT3 | 377 | 197 | | – | | | – | |
| RvT4 | 359 | 211 | 0.4 | ± | 0.2 | 0.6 | ± | 0.2 |
| EPA bioactive metabolome | | | | | | | | |
| RvE1 | 349 | 195 | 2.4 | ± | 1.9 | 3.6 | ± | 3.4 |
| RvE2 | 333 | 199 | 0.2 | ± | 0.2 | 0.7 | ± | 0.7 |
| RvE3 | 333 | 201 | 1.7 | ± | 1.1 | 1.1 | ± | 0.5 |
| AA bioactive metabolome | | | | | | | | |
| $LXA_4$ | 351 | 115 | 0.1 | ± | 0.0 | | – | |
| $LXB_4$ | 351 | 221 | 0.9 | ± | 0.5 | 0.5 | ± | 0.3 |
| 5S,15S-diHETE | 335 | 235 | 8.2 | ± | 1.7 | 16.6 | ± | 4.2 |
| 15epi-$LXA_4$ | 351 | 115 | 0.6 | ± | 0.3 | 0.9 | ± | 0.4 |
| 15epi-$LXB_4$ | 351 | 221 | 30.0 | ± | 10.7 | 20.0 | ± | 7.5 |
| $LTB_4$ | 335 | 195 | 2.0 | ± | 0.8 | 1.8 | ± | 0.3 |
| 5S,12S-diHETE | 335 | 195 | 1.0 | ± | 0.7 | 0.2 | ± | 0.1 |
| 20-OH-$LTB_4$ | 351 | 195 | 0.2 | ± | 0.1 | 0.6 | ± | 0.3 |
| $PGD_2$ | 351 | 189 | 1.7 | ± | 0.3 | 3.6 | ± | 1.2 |
| $PGE_2$ | 351 | 189 | 6.3 | ± | 1.8 | 8.1 | ± | 1.3 |
| $PGF_{2\alpha}$ | 353 | 193 | 8.1 | ± | 2.6 | 6.2 | ± | 1.2 |
| $TxB_2$ | 369 | 169 | 10.4 | ± | 6.2 | 20.4 | ± | 13.7 |

Peripheral blood from CVD patients was collected at 9:00 h (AM) and between 16:00-18:00 h (PM). Plasma was placed in ice-cold methanol containing internal standards. Lipid mediators (LM) were extracted, identified and quantified using LM-profiling (see methods for details). Q1, M-H (parent ion) and Q3, diagnostic ion in the MS-MS (daughter ion). Results are mean ± s.e.m. and expressed as pg/mL. n = 9 paired patients. The detection limit was ~0.1 pg. –, Below limits of detection.

Assessment of plasma $RvD_{n\text{-}3\ DPA}$ levels demonstrated significant decreases in both morning (9:00 h; am) and evening (16:00-18:00 h; pm) concentrations in CVD patients when compared to the respective intervals in healthy volunteers (FIG. 6C). In these patients, significant reductions in plasma concentrations of the $RvD_{n\text{-}3\ DPA}$ biosynthetic marker 7-HDPA (Dalli et al. 2013) were found (see FIG. 7). Furthermore, the ratio of plasma $RvD_{n\text{-}3\ DPA}$ to inflammation-initiating eicosanoids (prostaglandins, leukotriene B4 and $TxA_2$) was significantly lower in these patients at both intervals measured when compared to healthy volunteers indicating an elevated systemic inflammatory status ($p<0.05$).

This was further supported by the observation that peripheral blood leukocyte and platelets also displayed an increased activation status. Flow cytometric analysis demonstrated increases in the expression of CD11b on both neutrophils and monocytes from CVD patients when compared with healthy volunteers (FIGS. 6D and 6E). Increases in platelet-neutrophil and platelet-monocyte aggregates in peripheral blood from CVD patients were also found when compared with peripheral blood from healthy volunteers (FIGS. 4F and 4G).

In peripheral blood from these patients, a significant decrease in morning plasma ACh concentrations was found compared to evening values (FIG. 6H). Thus, these results suggest that a failure to upregulate peripheral blood ACh leads to $RvD_{n\text{-}3\ DPA}$ production in patients with CVD.

Example 5: Reduced Leukocyte Activation by $RvD2_{n\text{-}3\ DPA}$ and $RvD5_{n\text{-}3\ DPA}$ in Patient Peripheral Blood In order to test whether there was a relationship between the increased systemic inflammation and reduced n-3 DPA derived SPM, it was tested whether $RvD_{n\text{-}3\ DPA}$ regulated patient peripheral blood leukocyte responses. For this purpose, whole blood from these patients was incubated with $RvD2_{n\text{-}3\ DPA}$ and cellular responses were assessed using flow cytometry. $RvD2_{n\text{-}3\ DPA}$ dose-dependently decreased platelet-neutrophil and platelet-monocyte aggregates without significantly regulating CD11b expression (see FIG. 8).

Incubation of whole blood with $RvD5_{n\text{-}3\ DPA}$ also led to a reduction in neutrophil platelet and monocyte-platelet aggregates with higher potency than $RvD2_{n\text{-}3\ DPA}$ (FIGS. 8A and 8B). In addition, $RvD5_{n\text{-}3\ DPA}$ significantly reduced neutrophil and monocyte CD11b expression (FIGS. 8C and 8D).

It was tested whether the actions of these two mediators were also retained in the presence of PAF (Shinohara M et al. 2014; Palur Ramakrishnan A V et al. 2017). Incubation of patient whole blood with either $RvD2_{n\text{-}3\ DPA}$ or $RvD5_{n\text{-}3\ DPA}$ led to decreases in platelet-neutrophil and platelet-monocyte aggregates measured as decreases in CD62P (see FIGS. 9A and 9B) and CD41 expression (n=9 patients) on both leukocyte subsets.

It was also found that $RvD5_{n\text{-}3\ DPA}$ decreased the expression of CD11b on neutrophils and monocytes, an action that was only in part shared with $RvD2_{n\text{-}3\ DPA}$ (FIGS. 9C and 9D).

These results suggest that reductions in circulating $RvD_{n\text{-}3\ DPA}$ lead to increased circulating leukocyte and platelet activation in CVD patients.

Example 6: n-3 DPA Reduces RvD5 Systemic Leukocyte and Platelet Activation and Protects Against Vascular Disease in Apo $E^{-/-}$ Mice It was next investigated whether the protective actions of $RvD5_{n\text{-}3\ DPA}$ observed with peripheral blood cells from both healthy volunteers and CVD patients were also retained in vivo. For this purpose, Apo E mice were fed western diet for 6 weeks and $RvD5_{n\text{-}3\ DPA}$ (100 ng/mouse; i.v.) was administered on alternative days for a two-week period. $RvD5_{n\text{-}3\ DPA}$ administration reduced circulating platelet-monocyte aggregates, as measured by a decrease in both CD41 and CD62P expression on CD115 positive cells, and monocyte activation with a decrease in CD11b expression (FIG. 10A). A significant reduction in platelet-neutrophil aggregates and neutrophil activation was found, with a >60% reduction in CD11b expression in mice given $RvD5_{n\text{-}3\ DPA}$ when compared with mice given vehicle alone (FIG. 10B).

Since platelet-leukocyte aggregates are involved in the pathogenesis of atherosclerosis (Huo Y et al. 2003), it was investigated whether $RvD5_{n\text{-}3\ DPA}$ also protected against vascular disease. Oil red-O staining demonstrated a significant reduction in aortic lesions in mice given $RvD5_{n\text{-}3\ DPA}$ when compared to mice given vehicle (FIG. 10C). Furthermore, LC/MS-MS analysis of aortic sections demonstrated significant reductions in aortic prostanoids, with concentrations of $TxB_2$ being reduced by ~35% in mice given $RvD5_{n\text{-}3\ DPA}$ (FIG. 10D and Table 10 below). Together these findings demonstrate that the protective actions of $RvD5_{n\text{-}3\ DPA}$ on platelets and leukocytes are also retained in vivo leading to reduced vascular disease.

TABLE 10

Reduced eicosanoids in aortic tissues from Apo $E^{-/-}$ mice given $RvD5_{n\text{-}3\ DPA}$.

| | | | Lipid mediators concentration (pg/10 mg tissue) | | | | | |
|---|---|---|---|---|---|---|---|---|
| | Q1 | Q3 | Apo $E^{-/-}$ + Vehicle | | | Apo $E^{-/-}$ + $RvD5_{n\text{-}3\ DPA}$ | | |
| $PGD_2$ | 351 | 189 | 18.5 | ± | 2.8 | 15.0 | ± | 2.2 |
| $PGE_2$ | 351 | 189 | 21.5 | ± | 3.2 | 16.2 | ± | 2.7 |
| $PGF_{2a}$ | 353 | 193 | 10.8 | ± | 0.7 | 9.1 | ± | 2.2 |
| $TxB_2$ | 369 | 169 | 46.9 | ± | 6.5 | 30.7 | ± | 2.0* |

Descending aortas were placed in ice-cold methanol containing internal standards. Lipid mediators (LM) were extracted, identified and quantified using LM-profiling (see methods described above for details). Q1, M-H (parent ion) and Q3, diagnostic ion in the MS-MS (daughter ion). Results are mean ± s.e.m. and expressed as pg/10 mg tissue. n = 4 mice per group. * $p < 0.05$ vs Vehicle mice.

The above examples demonstrate a diurnal regulation of $RvD_{n\text{-}3\ DPA}$ in the vasculature of healthy volunteers. This upregulation in $RvD_{n\text{-}3\ DPA}$ coincides with an increase in platelet, monocyte and neutrophil activation during the morning hours. Circadian regulation of these pro-resolving mediators is controlled by the neurotransmitter ACh that is, in turn, also diurnally regulated in plasma of healthy volunteers. In CVD patients, significantly lower $RvD_{n\text{-}3\ DPA}$ was found as compared with healthy volunteers. A failure in the upregulation of these molecules during the early morning hours was also found that was linked with a decrease in plasma ACh concentrations and increased peripheral blood leukocyte activation. Incubation of whole blood from both patients and healthy volunteers with $RvD2_{n\text{-}3\ DPA}$ or $RvD5_{n\text{-}3\ DPA}$ significantly reversed leukocyte and platelet activation. In addition, administration of $RvD5_{n\text{-}3\ DPA}$ to Apo $E^{-/-}$ mice using a therapeutic paradigm reduced systemic platelet and leukocyte activation and vascular disease. Together these findings indicate that disruption in the ACh-$RvD_{n\text{-}3\ DPA}$ axis may result in CVD.

Figure 1:
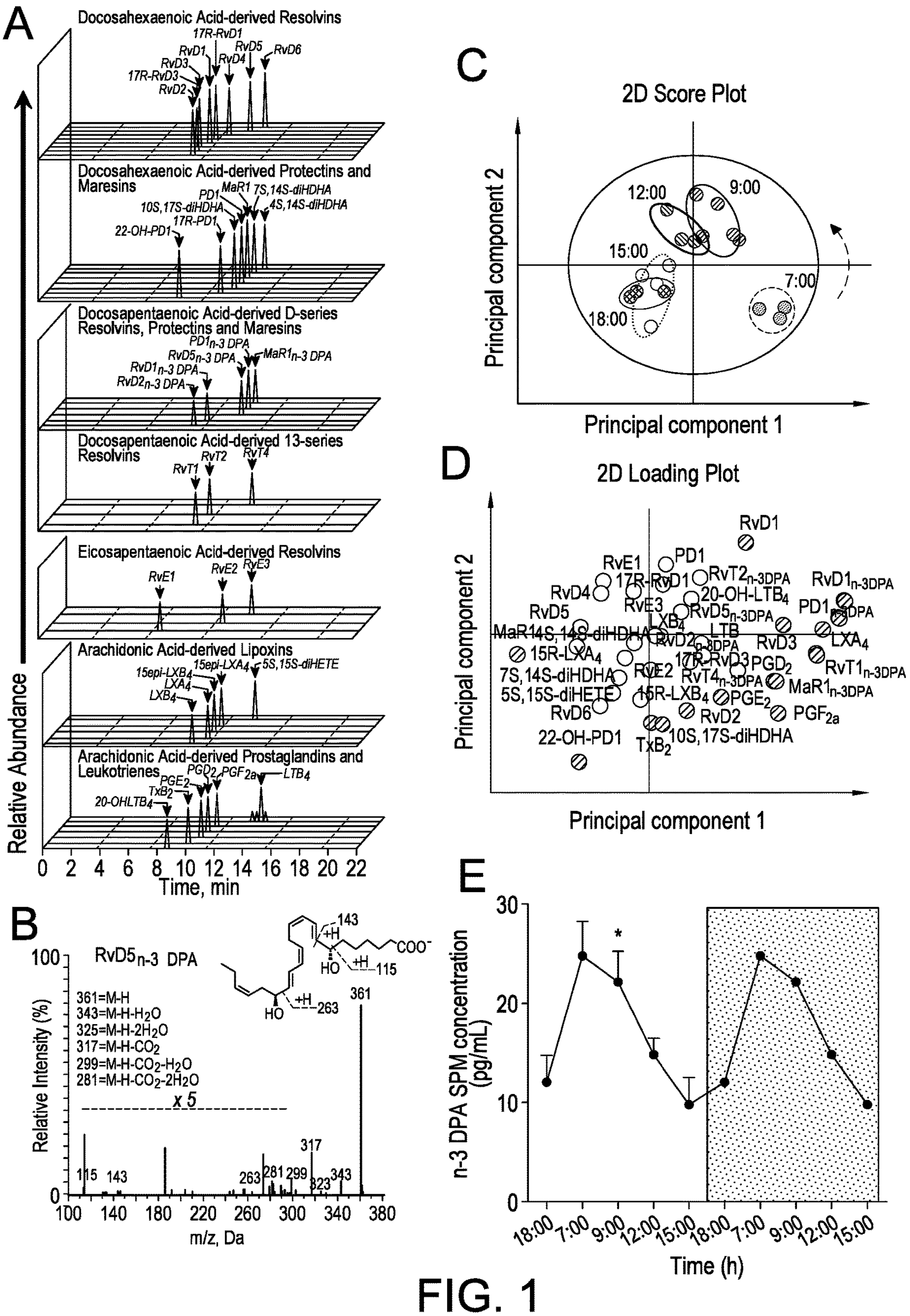
FIG. 1: Vascular n-3 DPA-derived SPM are diurnally regulated in human healthy volunteers. Peripheral blood was collected from healthy volunteers at the indicated intervals and plasma placed in ice-cold methanol containing deuterium labelled internal standards. Lipid mediators (LM) were extracted, identified and quantified using LM profiling (see the Materials and Methods section below for details). (A) Representative MRM for identified LM, (B) MS-MS spectra used for the identification of $RvD5_{n\text{-}3\ DPA}$. Results are representative of n=7 healthy volunteers. (C) PLS-DA 2-dimensional score plot of the distinct LM-SPM profiles identified human plasma at the indicated intervals and (D) corresponding 2-dimensional loading plot. Grey ellipse in the score plots denotes 95% confidence regions. Grey circles represent LM with a variable in importance score ≥1; n=4 healthy volunteers per interval. (E) n-3 DPA concentrations identified and quantified at each of the time intervals. Results are mean±s.e.m, n=7 per time point and expressed as pg/mL. *, p≤0.05 vs amounts at the 18 h interval. Statistical analysis was conducted on the results in the white portion of the panel. Results in the grey panel are re-plotted from the white portion to aid in visualization of rhythmicity.

Plasma $RvD_{n\text{-}3\ DPA}$ concentrations were found to increase during the early morning hours (FIG. 1 and Table 6 above). These molecules were reduced in peripheral blood from patients at risk of myocardial infarct that correlated with an increased leukocyte and platelet activation. Furthermore, $RvD_{n\text{-}3\ DPA}$ regulated reduced leukocyte and platelet responses in peripheral blood from both healthy volunteers and patients, and $RvD5_{n\text{-}3\ DPA}$ protected against vascular disease in Apo $E^{-/-}$ mice (FIG. 10). These findings indicate that alterations in the diurnal regulation of these molecules may represent a key aspect in the pathogenesis of cardiovascular diseases.

Plasma concentrations of the $RvD_{n\text{-}3\ DPA}$ pathway marker, and 5-LOX product (Dalli et al. 2013), 7-HDPA were significantly reduced (FIG. 7). These finding are in line with published findings implicating the 5-LOX pathway as a risk factor in developing cardiovascular disease (see Helgadottir A et al. Association between the gene encoding 5-lipoxygenase-activating protein and stroke replicated in a Scottish population. *Am J Hum Genet.* 2005; 76(3):505-509).

Results from the above examples demonstrate that the vascular levels of this neurotransmitter in healthy volunteers are diurnally regulated and increase during the early morning hours (FIG. 3), a mechanism that was dysregulated in patients with CVD (FIG. 8). Thus, these results point to an uncoupling of plasma ACh regulation that leads to a reduction in the biosynthesis of $RvD_{n\text{-}3\ DPA}$ in CVD patients.

In summary, the above examples demonstrate a protective pathway that is centered on the diurnal regulation of vascular n-3 DPA-derived pro-resolving mediators. Increases in these molecules during the morning hours counter-regulate physiological platelet and leukocyte activation limiting systemic inflammation and potentially vascular disease. In patients with cardiovascular disease, there is a significant loss in the production of these molecules with an increase in peripheral blood cell activation leading to increased systemic inflammation and CVD, including risk of myocardial infarct. In line with this notion, $RvD_{n\text{-}3\ DPA}$ reprogrammed circulating leukocyte and platelet activation, which in mice resulted in a significant reduction in vascular disease. Thereby, strategies to restore peripheral blood $RvD_{n\text{-}3\ DPA}$, including n-3 DPA supplementation that was recently shown to increase plasma $RvD5_{n\text{-}3\ DPA}$ in healthy volunteers (Markworth J F et al. Divergent shifts in lipid mediator profile following supplementation with n-3 docosapentaenoic acid and eicosapentaenoic acid. *FASEB J.* 2016; 30(11):3714-3725) may present possible therapeutic options. In addition, therapeutics based on the $RvD_{n\text{-}3\ DPA}$ may provide new opportunities for fine-tuning the increased inflammatory status present in these patients, dampening systemic inflammation and reducing vascular disease.

Example 7: Assessment of the Efficacy of a Medicament for the Treatment or Prevention of Cardiovascular Disease A method of assessing the efficacy of a medicament for use in the treatment or prevention of cardiovascular disease in an individual patient in accordance with the present invention is illustrated in FIG. 11. Typically, the individual patient is a person who has been diagnosed with cardiovascular disease and may be at risk of suffering myocardial infarction or another kind of adverse acute cardiovascular event.

Step 10 indicates the start of the method. First, before the start of treatment with the medicament, a first biological sample is taken from the patient (step 20). In the present example, the biological sample is a plasma sample, but in other embodiments, the sample may be whole blood or serum taken from the patient. The sample is taken from the patient in the early hours of the morning between 7 AM and 9 AM. In the present example, the sample is taken from the patient at 8 AM.

The patient is then started on a course of treatment with the medicament (step 30).

The medicament may be any suitable medicament for the treatment or prevention of cardiovascular disease. In particular, the medicament may be a statin, a fibrate, a calcium channel blocker or combinations of medicaments such, for example, as a combination of a statin and calcium channel blocker. Other suitable cardiovascular treatments will be known to those skilled in the art. A suitable medicament is selected by a medical practitioner based on the patient's medical history and symptoms.

Suitable statins include simvastatin, fluvastatin, atorvastatin, rosuvastatin, pravastatin, lovastatin.

Suitable fibrates include gemfibrozil, fenofibrate, clofibrate, bezafibrate, ciprofibrate, clinofibrate, clofibride, ronifibrate and simfibrate.

Suitable calcium channel blockers include amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine and pranidipine.

The medicament is administered (including self-administration) to the patient in accordance with the medical practitioner's prescription. Typically, the medicament may be administered one or more times per day.

After a prescribed period of time after commencing treatment with the medicament, a second biological sample is taken from the patient (step 40). In the present example, the prescribed period of time is 24 hours, but other time periods may be used in different embodiments. Typically, the prescribed period of time may between 1 and 14 or 30 days. In any event, the period of time should be sufficiently long to allow the pharmacological effects of the medicament to manifest themselves in the patient.

The second sample is also taken from the patient in the early hours of morning at the same time of day as the first sample, i.e. 8 AM in the present example.

In step 50, the first and second samples taken from the patient in steps 20 and 40, before and after commencing treatment with the medicament, are analysed to quantify the levels of at least one n-3 DPA-derived resolvin ($RvD_{n\text{-}3\ DPA}$) in the samples.

In the present example, the levels of three n-3 DPA-derived resolvins ($RvD1_{n\text{-}3\ DPA}$, $RvD2_{n\text{-}3\ DPA}$ and $RvD5_{n\text{-}3\ DPA}$) are measured in the first and second samples by reverse phase liquid chromatography electrospray tandem mass spectrometry (LC-MS/MS). In different embodiments of the invention, fewer than three of the n-3 DPA-derived resolvins may be analysed, i.e. one or two of the n-3 DPA-derived resolvins. Details of this method of quantitating the levels of the n-3 DPA-derived resolvins in the first and second samples are disclosed in Colas R A et al. 2014 and Dalli et al. 2015, the contents of which are incorporated herein by reference.

For each of the first and second plasma samples, venous blood (10 mL) is collected in heparin from the patient. Plasma is obtained by centrifugation of heparinised blood (2000 g, 10 minutes) and placed in 4 volumes of methanol before solid-phase extraction as described below.

Internal labelled standards 5S-HETE-$d_8$, $LTB_4$-$d_4$, $LXA_4$-$d_5$, RvD2-$d_5$ and $PGE_2$-$d_4$ (500 pg each) in 4 mL of ice-cold methanol are added to each sample to facilitate quantification and sample recovery. Next, samples are held at −20° C. For 45 minutes to allow protein precipitation and then centrifuged (2000 g, 4° C., 10 minutes). Supernatants are collected and brought to less than 1 mL of methanol content in a gentle stream of nitrogen onto an automated evaporation system with the water bath set to 37° C. and a nitrogen feed with a flow rate of no more than 15 psi. The samples are then centrifuged (2000 g, 4° C., 10 minutes). Samples are then placed in an automated extraction system with the water bath set to 37° C. and a nitrogen feed with a flow rate of no more than 15 psi and products extracted as follows.

Solid-phase C18 cartridges are washed with 3 mL of methanol and 6 mL of $H_2O$. 9 mL $H_2O$ (pH 3.5, HCl) is then added to the samples, and the acidified solutions are rapidly loaded onto the conditioned C18 columns that are washed with 4 mL of $H_2O$ to neutralise the acid. Next, 5 mL of hexane are added and the products are eluted with 9 mL methyl formate. Products are brought to dryness using the automated evaporation system and immediately suspended in methanol-water (50:50 vol/vol) for LC-MS/MS automated injections.

In the present example, for LC-MS/MS, an HPLC and autoinjector, paired with a triple quadrupole mass spectrometer fitted with a high dynamic range pulse counting system, is employed. Alternative suitable LC-MS/MS equipment is available to those skilled in the art. A C18 column is kept in a column oven maintained at 50° C., and the RvD lipid mediators are eluted with a mobile phase consisting of water containing 0.01% acetic acid as a solvent A and methanol containing 0.01% acetic acid as solvent B. The column is equilibrated with mobile phase at 80:20 (A:B) which is ramped to 50:50 (A:B) over 12 seconds. This gradient is maintained for two minutes and then ramped to 80:20 (A:B) over the next 9 minutes. This gradient is then maintained for the next 3.5 minutes, before ramping to 98:2 (A:B). Finally, this gradient is maintained for 5.4 minutes to wash the column. The flow rate is maintained at 0.5 mL/min throughout the process.

The mass spectrometer is operated in negative ionisation mode using scheduled multiple reaction monitoring (MRM) coupled with information-dependent acquisition and an enhanced product line scan. The scheduled MRM window is 90 seconds, and each lipid mediator parameter is optimised individually.

The identity of each $RvD_{n\text{-}3\ DPA}$ (n-3 DPA-derived resolvin) is confirmed by matching its retention time ($R_T$) to synthetic and authentic materials (FIGS. 3B and 6A) and at least six diagnostic ions for each RvD (FIGS. 3C and 6B) and quantified using multiple reaction monitoring of the parent ion (Q1) and characteristic daughter ion (Q3) as described in Table 11 below.

TABLE 11

| Diagnostic ions for $RvD_{n\text{-}3\ DPA}$ | | |
|---|---|---|
| RvD | Q1 | Q3 |
| $RvD1_{n\text{-}3\ DPA}$ | 377 | 215 |
| $RvD2_{n\text{-}3\ DPA}$ | 377 | 261 |
| $RvD5_{n\text{-}3\ DPA}$ | 361 | 263 |

Calibration curves are obtained for each using authentic compound mixtures and deuterium labelled lipid mediators at 3.12, 6.25, 12.5, 25, 50, 100 and 200 pg. Linear calibration curves are obtained for each LM, which gives $r^2$ values of 0.98-0.99. Internal standard recoveries, interference of the matrix, and limit of detection are determined.

Following quantitation of the levels of the RvDs in each of the first and second samples, the levels are compared (step 60).

A significant increase in the levels of the RvDs in the second sample as compared to the first sample indicates that the medicament administered to the patient may be effective in treating or preventing cardiovascular disease, particularly cardiovascular disease that is mediated by vascular inflammation as a result of dysfunctional diurnal control over pro-inflammatory mediators. On the other hand, no increase in the levels of the RvDs in the second sample as compared with the first sample may indicate that the administered medicament is ineffective in the individual patient.

Based on these results, the medicament may be prescribed to the patient if it is indicated as being effective (step 80). Alternatively, the method may be repeated using a different medicament.

Step 90 indicates the end of the method.

Example 8

Further examples of different aspects of the present invention are described below with reference to FIGS. 12 and 13 in which an immunoassay incorporated into a microfluidic device 110 is used for measuring the level of at least one n-3 DPA-derived resolvin ($RvD_{n\text{-}3\ DPA}$) in a sample of blood B obtained from a patient P.

As best shown in FIG. 12, the microfluidic device 110 has a general construction of the kind known to those skilled in the art. Specifically, the microfluidic device 110 comprises at least one layer of polydimethylsiloxane (PDMS) 112, a transparent, biocompatible elastomer that allows for channel inspection and optical signal acquisition, bonded to a glass slide 114.

The PDMS layer is moulded with a plurality of micro-channels 120*a-c* which terminate at one end at a sample collector port 125 and at another end at a waste drain 130. In the present example, the microfluidic device 110 has three micro-channels 120*a-c*, one for measuring the level of a different respective n-3 DPA-derived resolvin ($RvD1_{n\text{-}3\ DPA}$, $RvD2_{n\text{-}3\ DPA}$, $RvD5_{n\text{-}3\ DPA}$) in the blood sample B. In variants of the present example, the microfluidic device may have fewer than three micro-channels, for instance one or two micro-channels for measuring the levels of a corresponding number of $RvD_{n\text{-}3\ DPA}$.

Between the sample collector port 125 and the waste drain 130, each of the micro-channels 120*a-c* comprises a reaction zone 150*a-c*. Suitably, the micro-channels 120*a-c* may be serpentine in the reaction zone 150*a-c* to promote mixing of the sample B and reagents added to the device as described below.

Intermediate the sample collection port 125 and its reaction zone 150*a-c*, each microchannel 120 *a-c* is provided with a respective reagent inlet port 140*a-c* for admitting a series of different reagents into the channels 120*a-c* for mixing with the sample B. The micro-channels 120*a-c* and inlet ports 140*a-c* are provided with suitable micro-valves or the like for controlling the flow of the sample and reagents.

In each reaction zone 150*a-c*, a surface of each micro-channel 120*a-c* is coated with a monoclonal antibody to a different respective one of $RvD_{n\text{-}3\ DPA}$ to be quantitated in the sample B.

Adjacent each reaction zone 150*a-c*, the device 110 incorporates hydrogenated amorphous silicon (a-Si:H) photodiodes 175*a-c* on the glass slide 114. The photodiodes 175*a-c* are connected to a suitable interface 120, which is connected to a first computer 200 as shown in FIG. 13.

The interface 120 is arranged to receive signals from the photodiodes 175*a-c* and to transmit computer-readable data to the first computer 200 representing those signals. The interface 120 may be physically connected to the first computer 200 by a suitable data cable. Alternatively, the interface 120 may be connected wirelessly to the first computer 200 by any suitable wireless data transfer method such, for example, as Bluetooth®. In some embodiments, the first computer may comprise a handheld device.

The first computer 200 comprises a microprocessor, a memory and a storage device, and is arranged to execute software for storing data representing the signals received from the photodiodes 175*a-c* in association with patient identity data. Where the first computer 200 is a handheld device, the software may be an App.

The first computer 200 is connected via a suitable data communication channel 300 to a remote second computer 400. In the present embodiment, the data communication channel 300 comprises the Internet, but in other embodiments, the first and second computers 200, 400 may be interconnected on a local or wide area network (not shown). The first and second computers 200, 400 may be physically to each other connected via data communication cables, or they may be interconnected wirelessly using a suitable wireless data communication technology such, example, as IEEE 802.11 a,b,g,n or Bluetooth®. Suitably, each of the first and second computers 200, 400 is connected to the Internet 300 through a suitable modem.

In use, a sample of blood B is obtained from a patient, for example using a conventional lancet. The sample B is placed on the microfluidic device 110 at the sample inlet port 125. The sample is drawn into the micro-channels 120*a*-*c* by capillary action. In alternative embodiments, the sample B may be actively drawn into the micro-channels 120*a*-*c* using a micro-pump or under reduced pressure, etc.

In the reaction zones 150*a*-*c*, $RvD_{n\text{-}3\ DPA}$ in the samples react with the antibodies coated on the surface of the micro-channels 120*a*-*c*. A different $RvD_{n\text{-}3\ DPA}$ is captured in each reaction zone 150*a*-*c*. The sample B is incubated with the antibodies in the reaction zone for a suitable period of time. A wash solution is then introduced into the micro-channels 120*a*-*c* to remove unbound sample. Discarded material from the micro-channels 120*a*-*c* is removed from the device 110 via the drain 130.

After removing unbound sample from the reaction zone 150*a*-*c*, a second monoclonal antibody is introduced into each of the micro-channels 120*a*-*c* with specificity for the respective $RvD_{n\text{-}3\ DPA}$. Each of the second antibodies is tagged with horseradish peroxidase in the manner well known to those skilled in the art. The second monoclonal antibodies are allowed to incubate with the surface-captured $RvD_{n\text{-}3\ DPA}$ in the reaction zones 150*a*-*c*. The micro-channels 120*a*-*c* are then washed again.

Next, a substrate for horseradish peroxidase is introduced into each of the micro-channels 120*a*-*c* via the inlet ports 140*a*-*c*. Suitable substrates are known to those skilled in the art, but in the present example luminol is used, which fluoresces when acted on by horseradish peroxidase. The fluorescence is detected by the photodiodes 175 giving rise to signals that are received by the interface 180. The intensity of the fluorescence is indicative of the amount of second antibody that is bound to the immobilised $RvD_{n\text{-}3\ DPA}$ in each of the channels 120*a*-*c*. The microfluidic device 110 may be calibrated in a manner known to those skilled in the art so that the level of $RvD_{n\text{-}3\ DPA}$ in each of the micro-channels 120*a*-*c* can be quantitated.

Data representing the intensity of fluorescence in each microchannel 120*a*-*c* is transmitted from the interface 180 to the first computer 200 as described above. The computer 200 executes the aforementioned software to calculate the level of each $RvD_{n\text{-}3\ DPA}$ in the sample B from the intensity of fluorescence measured by the photodiodes 175.

The microfluidic device is then washed through again with a suitable washing agent.

In the present example, a first blood sample $B^1$ is taken from the patient in the evening, for example between about 4 PM and 6 PM, and the levels of the $B^1$ are measured using the microfluidic device 110 as described above.

A second sample $B^2$ is taken from the patient in the early hours of the following morning, for example between about 7 AM and 9 AM. The levels of the one or more $RvD_{n\text{-}3\ DPA}$ in the sample $B^2$ are measured using the same or a similar microfluidic device 110 as described above.

Data representing the levels of the one or more $RvD_{n\text{-}3\ DPA}$ in the samples $B^1$ and $B^2$ are calculated and stored by the first computer 200.

Data representing the levels of the one or more $RvD_{n\text{-}3\ DPA}$ in the first and second samples are then transmitted by the first computer 200 to the second computer 400 in association with information identifying the patient P.

The second computer 400 includes a microprocessor, memory and a storage device and is arranged to execute software for calculating the difference between the levels of the one or more $RvD_{n\text{-}3\ DPA}$ in the first and second samples $B^1$, $B^2$.

Since, in a healthy individual, one would normally expect the plasma level of $RvD_{n\text{-}3\ DPA}$ to be in the range 10-25 pg/mL in the early morning, with a minimum of around 5 pg/mL in the evening, if the difference in the levels of the $RvD_{n\text{-}3\ DPA}$ between the first and second samples $B^1$, $B^2$ is less than about 5 pg/mL, the patient may be assessed to be at risk of cardiovascular disease, and data indicating this is transmitted from the second computer back to the first computer 200 where it is saved and/or displayed to a person carrying out the test.

Similarly, if the level of $RvD_{n\text{-}3\ DPA}$ in the patient's blood in the sample $B^2$ taken early in the morning is less than around 10 pg/mL, particularly if it is less than around 5 pg/mL, this may indicate that the patient is at risk of cardiovascular disease or myocardial infarction.

On the basis of the comparison of the $RvD_{n\text{-}3\ DPA}$ levels in the first and second samples $B^1$, $B^2$, the patient may be prescribed a suitable medicament for the treatment or prevention of cardiovascular disease.

In the present example, the microfluidic device 110 is arranged to carry out a non-competitive, heterogeneous ELISA sandwich immunoassay. However, in variants of the invention, a microfluidic device may be arranged to carry out a homogeneous immunoassay and/or a competitive immunoassay.

For example, in one variant, each microchannel 120*a*-*c* may be coated on a surface within its respective reaction zone 150*a*-*c* with a respective $RvD_{n\text{-}3\ DPA}$ (e.g. $RvD1_{n\text{-}3\ DPA}$, $RvD2_{n\text{-}3\ DPA}$ or $RvD5_{n\text{-}3\ DPA}$) which is the same as the one in the sample B that is to be analysed in the respective reaction zone 150*a*-*c*. Intermediate the reaction zone 150*a*-*c* and the sample collection port 125, in each microchannel 120*a*-*c* the sample B may be mixed with a known amount of a primary antibody to the respective $RvD_{n\text{-}3\ DPA}$. The primary antibody is provided in excess, and remaining antibody will then subsequently react with the surface-bound $RvD_{n\text{-}3\ DPA}$ in the reaction zone 150*a*-*c*, effectively in competition with the corresponding $RvD_{n\text{-}3\ DPA}$ in the sample. After washing, a labelled secondary antibody is introduced into each reaction zone 150*a*-*c* through the inlet ports 140*a*-*c* which is specific for the respective primary antibody. As described above, the secondary antibody is tagged with an enzyme suitable for use in EIA such, for example, as horseradish peroxidase. The amount of secondary antibody remaining after reaction with the sample can then be measured by admitting a suitable substrate for horseradish peroxidase into the reaction zones 150*a*-*c* and measuring the intensity of the fluorescence or colour as described above.

A microfluidic device in accordance with the invention such, for example, as microfluidic device 110 described above provides a convenient device for performing the methods of the present invention in a point of care setting such, for example, as a healthcare clinic where there is no access to more sophisticated equipment such as LC-MS/MS which may only be found in large laboratories.

Example 9: Diurnal Changes in Peripheral Blood n-3 DPA-Derived SPM are Regulated by Acetylcholine To investigate whether peripheral blood SPM concentrations are diurnally regulated we obtained plasma from healthy volunteers at distinct intervals during a 24 h period, with demographics as set out in Table 12 below:

TABLE 12

| Healthy volunteers demographics | | | |
|---|---|---|---|
| Sex | Age (years) | Weight (Kg) | BMI (Kg/$m^2$) |
| 3M/4F | 34 ± 4.1 | 65.6 ± 11.3 | 23.2 ± 3.0 |

In plasma from healthy volunteers we identified mediators from all four major essential fatty acid metabolomes, including the EPA derived E-series resolvins, n-3 DPA-derived resolvins and protectins, DHA-derived protectins and maresins and the arachidonic acid (AA)-derived prostaglandins and leukotrienes. These mediators were identified in accordance with published criteria (Dalli J, Colas R A, Serhan C N. Novel n-3 immunoresolvents: structures and actions. Sci Rep. 2013; 3:1940) as illustrated for $RvD5_{n\text{-}3\ DPA}$ (FIG. 14). Multivariate analysis of plasma lipid mediator profiles demonstrated a diurnal shift in plasma LM-SPM concentrations with a leftward shift in LM-SPM clusters from morning to evening profiles (FIG. 20 A,B). This shift was associated with an increase in the amounts of n-3 DPA derived mediators, including $RvD1_{n\text{-}3\ DPA}$ and $RvD5_{n\text{-}3\ DPA}$ from the evening (18:00 h) to morning intervals (7:00 and 9:00 h; FIG. 20C). We also found diurnal changes in plasma Thromboxane $(Tx)B_2$, the inactive further metabolite of the potent platelet agonist $TxA_2$ (see Samuelsson B. Role of basic science in the development of new medicines: examples from the eicosanoid field. *J Biol Chem.* 2012; 287(13):10070-10080), as summarised in Table 13 below:

TABLE 13

Diurnal lipid mediator profiles in healthy volunteer peripheral blood.

| DHA bioactive metabolome | Q1 | Q3 | Healthy volunteer plasma Lipid mediators concentration (pg/mL) 18:00 | 7:00 | 9:00 | 12:00 | 15:00 |
|---|---|---|---|---|---|---|---|
| RvD1 | 375 | 141 | 0.8 ± 0.4 | 0.8 ± 0.3 | 1.4 ± 0.4 | 0.8 ± 0.3 | 0.8 ± 0.2 |
| RvD2 | 375 | 141 | 0.9 ± 0.4 | 0.9 ± 0.2 | 0.6 ± 0.3 | 0.3 ± 0.2 | 0.3 ± 0.2 |
| RvD3 | 375 | 147 | 0.1 ± 0.0 | 0.6 ± 0.4 | 0.4 ± 0.2 | 0.2 ± 0.1 | 0.1 ± 0.0 |
| RvD4 | 375 | 101 | 0.3 ± 0.2 | 0.3 ± 0.2 | 0.3 ± 0.2 | 1.3 ± 0.8 | 0.8 ± 0.6 |
| RvD5 | 359 | 199 | 0.6 ± 0.2 | 0.3 ± 0.2 | 0.3 ± 0.1 | 0.5 ± 0.2 | 0.5 ± 0.1 |
| RvD6 | 359 | 101 | 0.6 ± 0.2 | 0.4 ± 0.1 | 0.7 ± 0.4 | 0.7 ± 0.2 | 0.8 ± 0.3 |
| 17R-RvD1 | 375 | 141 | 0.2 ± 0.1 | 0.4 ± 0.2 | 0.3 ± 0.2 | 0.4 ± 0.2 | 0.4 ± 0.1 |
| 17R-RvD3 | 375 | 147 | 0.1 ± 0.1 | 0.2 ± 0.1 | 0.1 ± 0.1 | 0.1 ± 0.1 | 0.2 ± 0.1 |
| PD1 | 359 | 153 | 0.6 ± 0.2 | 0.7 ± 0.4 | 0.8 ± 0.3 | 1.0 ± 0.4 | 1.0 ± 0.6 |
| 17R-PD1 | 359 | 153 | 0.6 ± 0.3 | 0.4 ± 0.3 | 0.4 ± 0.2 | 0.3 ± 0.2 | 0.3 ± 0.2 |
| 10S,17S-diHDHA | 359 | 153 | 0.6 ± 0.2 | 1.4 ± 0.4 | 1.1 ± 0.6 | 0.7 ± 0.4 | 0.7 ± 0.2 |
| 22-OH-PD1 | 375 | 153 | 0.8 ± 0.4 | 1.3 ± 0.7 | 1.1 ± 0.5 | 1.4 ± 0.7 | 2.7 ± 2.1 |
| MaR1 | 359 | 221 | 1.0 ± 0.3 | 0.6 ± 0.2 | 1.2 ± 0.2 | 1.1 ± 0.4 | 1.0 ± 0.4 |
| 7S,14S-diHDHA | 359 | 221 | 1.1 ± 0.4 | 1.0 ± 0.3 | 0.6 ± 0.4 | 1.0 ± 0.3 | 0.8 ± 0.4 |
| 4S,14S-diHDHA | 359 | 101 | 11.3 ± 8.5 | 8.5 ± 5.7 | 7.8 ± 4.8 | 9.1 ± 5.6 | 8.1 ± 5.5 |
| n-3 DPA bioactive metabolome | | | | | | | |
| $RvD1_{n\text{-}3\ DPA}$ | 377 | 143 | 1.9 ± 0.4 | 10.9 ± 4.2* | 7.5 ± 2.3* | 6.0 ± 1.8 | 1.6 ± 0.3 |
| $RvD2_{n\text{-}3\ DPA}$ | 377 | 261 | 2.3 ± 1.3 | 1.8 ± 1.0 | 2.5 ± 1.1 | 1.7 ± 1.2 | 1.1 ± 0.7 |
| $RvD5_{n\text{-}3\ DPA}$ | 361 | 263 | 2.6 ± 1.2 | 2.6 ± 1.2 | 4.5 ± 0.3* | 2.3 ± 1.2 | 3.2 ± 2.2 |
| $PD1_{n\text{-}3\ DPA}$ | 361 | 183 | 1.1 ± 0.3 | 2.3 ± 0.5 | 1.6 ± 0.3 | 1.6 ± 0.3 | 1.1 ± 0.3 |
| $MaR1_{n\text{-}3\ DPA}$ | 361 | 249 | 1.7 ± 0.7 | 3.5 ± 1.9 | 3.2 ± 1.4 | 0.9 ± 1.0 | 1.3 ± 0.6 |
| RvT1 | 377 | 193 | 0.1 ± 0.1 | 0.6 ± 0.2 | 0.3 ± 0.1 | 0.4 ± 0.2 | – |
| RvT2 | 377 | 143 | 0.3 ± 0.2 | 0.5 ± 0.3 | 0.5 ± 0.3 | 0.5 ± 0.3 | 0.3 ± 0.2 |
| RvT3 | 377 | 255 | – | – | – | – | – |
| RvT4 | 359 | 193 | 2.0 ± 0.8 | 2.6 ± 1.4 | 3.0 ± 1.3 | 1.4 ± 0.6 | 1.4 ± 0.6 |
| EPA bioactive metabolome | | | | | | | |
| RvE1 | 349 | 195 | 3.9 ± 1.5 | 3.7 ± 1.5 | 4.5 ± 1.5 | 4.9 ± 1.9 | 4.9 ± 2.0 |
| RvE2 | 333 | 199 | 2.3 ± 0.6 | 1.9 ± 0.7 | 2.5 ± 0.8 | 2.3 ± 0.8 | 2.7 ± 1.1 |
| RvE3 | 333 | 201 | 1.2 ± 0.3 | 1.4 ± 0.5 | 1.6 ± 0.4 | 1.4 ± 0.6 | 1.3 ± 0.6 |

TABLE 13-continued

Diurnal lipid mediator profiles in healthy volunteer peripheral blood.

| DHA bioactive metabolome | Q1 | Q3 | 18:00 | 7:00 | 9:00 | 12:00 | 15:00 |
|---|---|---|---|---|---|---|---|
| | | | Healthy volunteer plasma Lipid mediators concentration (pg/mL) | | | | |
| AA bioactive metabolome | | | | | | | |
| $LXA_4$ | 351 | 217 | 0.3 ± 0.1 | 0.8 ± 0.4 | 0.7 ± 0.3 | 0.6 ± 0.2 | 0.6 ± 0.2 |
| $LXB_4$ | 351 | 221 | 0.9 ± 0.4 | 0.8 ± 0.3 | 0.2 ± 0.2 | 0.5 ± 0.2 | 0.6 ± 0.2 |
| 5S,15S-diHETE | 335 | 235 | 11.7 ± 3.6 | 9.2 ± 3.5 | 19.0 ± 11.2 | 8.9 ± 2.4 | 8.5 ± 3.0 |
| 15epi-LXA4 | 351 | 217 | 7.0 ± 3.1 | 8.3 ± 5.5 | 4.2 ± 1.2 | 4.6 ± 1.2 | 4.2 ± 1.1 |
| 15epi-LXB4 | 351 | 221 | 1.7 ± 0.9 | 1.0 ± 0.2 | 1.5 ± 0.4 | 0.5 ± 0.2 | 2.3 ± 1.0 |
| $LTB_4$ | 335 | 195 | 2.0 ± 0.5 | 2.5 ± 0.7 | 2.6 ± 1.2 | 1.8 ± 0.6 | 1.9 ± 0.5 |
| 5S,12S-diHETE | 335 | 195 | 0.1 ± 0.1 | 0.1 ± 0.1 | 0.1 ± 0.1 | 0.1 ± 0.1 | 0.1 ± 0.1 |
| 20-OH-$LTB_4$ | 351 | 195 | 0.1 ± 0.0 | 0.3 ± 0.2 | 0.3 ± 0.1 | 0.1 ± 0.1 | 0.2 ± 0.1 |
| $PGD_2$ | 351 | 189 | 5.8 ± 1.7 | 7.5 ± 1.5 | 4.7 ± 0.4 | 6.6 ± 1.8 | 7.6 ± 1.6 |
| $PGE_2$ | 351 | 189 | 5.9 ± 0.8 | 8.7 ± 3.6 | 4.4 ± 1.2 | 5.3 ± 1.2 | 6.5 ± 1.5 |
| $PGF_{2\alpha}$ | 353 | 193 | 6.1 ± 1.5 | 11.8 ± 2.5 | 7.0 ± 1.3 | 6.3 ± 0.9 | 8.9 ± 0.7 |
| $TxB_2$ | 369 | 169 | 233.6 ± 149.7 | 364.5 ± 176.9 | 92.3 ± 34.2 | 183.6 ± 100.0 | 415.8 ± 305.8 |

Peripheral blood was collected from healthy volunteers at the indicated intervals. Plasma was placed in ice-cold methanol and lipid mediators (LM) were assessed using LM-profiling (see methods for details). Q1, M-H (parent ion) and Q3, diagnostic ion in the MS-MS (daughter ion). Results are mean ± s.e.m. and expressed as pg/mL. n = 7 volunteers per interval. The detection limit was ~0.1 pg. –, Below limits of detection * P < 0.05 vs 18:00 h values using paired Mann-Whitney test.

These diurnal changes in $RvD_n$-3 DPA were also associated with a circadian regulation of leukocyte and platelet activation that reaches a maximum between 7:00 and 9:00 h coincident with an increase in $RvD_n$-3 DPA concentrations (FIG. 20 D-F, FIG. 15A). Of note, we also found a significant association between peripheral blood $RvD_n$-3 DPA concentrations and morning leukocyte activation, where lower $RvD_n$-3 DPA were associated with increased peripheral blood leukocyte and platelet activation (FIG. 20 G,H and FIG. 15 B,C).

We next investigated the mechanism(s) by which peripheral blood n-3 DPA derived SPM may be regulated. Here we found that plasma ACh concentrations mirrored those of the $RvD_n$-3 DPA reaching a maximum at 7:00 h (FIG. 16A), suggesting that ACh may regulate the $RvD_n$-3 DPA in peripheral blood given its role in SPM biosynthesis (Dalli J, Colas RA, Amardottir H, Serhan CN. Vagal Regulation of Group 3 Innate Lymphoid Cells and the Immunoresolvent PCTRI Controls Infection Resolution. Immunity. 2017;46 (1):92-105). Incubation of whole blood with ACh increased $RvD_n$-3 DPA concentrations, including RvD2$_n$-3 DPA, under both static and flow conditions, as shown in FIG. 16 B-E and in Table 14 below.

Table 14: ACh regulation of n-3 DPA metabolome in human whole blood. Peripheral blood from healthy volunteers was collected and incubated with ACh (0.1 μM; 45 min; 37 oC). Incubations were quenched with ice-cold methanol and n-3 DPA-derived LM identified and quantified using LM-profiling (see methods for details). Q1, M-H (parent ion) and Q3, diagnostic ion in the MS-MS (daughter ion). Results are expressed as pg/mL, mean±s.e.m, n=9 donors per group. * p<0.05 vs Vehicle group using paired Mann-Whitney test.

TABLE 14

ACh regulation of n-3 DPA metabolome in human whole blood.

| n-3 DPA bioactive metabolome | Q1 | Q3 | Vehicle | ACh 0.1 μM |
|---|---|---|---|---|
| | | | Lipid mediators concentration (pg/mL) | |
| $RvD1_{n\text{-}3\ DPA}$ | 377 | 143 | 3.4 ± 1.8 | 4.9 ± 2.8 |
| $RvD2_{n\text{-}3\ DPA}$ | 377 | 261 | 2.8 ± 1.2 | 7.4 ± 2.6* |
| $RvD5_{n\text{-}3\ DPA}$ | 361 | 201 | 0.8 ± 0.7 | 1.5 ± 0.6 |
| $PD1_{n\text{-}3\ DPA}$ | 361 | 155 | 0.4 ± 0.2 | 0.5 ± 0.1 |
| $MaR1_{n\text{-}3\ DPA}$ | 361 | 223 | 0.3 ± 0.2 | 0.9 ± 0.3* |
| RvT1 | 377 | 211 | 0.3 ± 0.3 | 2.0 ± 1.3 |
| RvT2 | 377 | 197 | 1.2 ± 0.8 | 1.6 ± 0.9 |
| RvT3 | 377 | 255 | 1.2 ± 0.9 | 1.4 ± 0.9 |
| RvT4 | 359 | 211 | 0.5 ± 0.3 | 1.0 ± 0.4 |

Peripheral blood from healthy volunteers was collected and incubated with ACh (0.1 μM; 45 min; 37oC). Incubations were quenched with ice-cold methanol and n-3 DPA-derived LM identified and quantified using LM-profiling (see methods for details). Q1, M-H (parent ion) and Q3, diagnostic ion in the MS-MS (daughter ion). Results are expressed as pg/mL, mean ± s.e.m, n = 9 donors per group. * p < 0.05 vs Vehicle group using paired Mann-Whitney test.

Of note, this increase was not linked with a selective mobilization of n-3 DPA in peripheral blood, see Table 15:

TABLE 15

Peripheral blood SPM substrate and precursor concentrations.

| n-3 DPA bioactive metabolome | Q1 | Q3 | Lipid mediators precursors concentration (pg/mL) Vehicle | ACh 0.1 μM |
|---|---|---|---|---|
| 17HDHA | 343 | 245 | 101.9 ± 26.7 | 103.6 ± 25.9 |
| 14HDHA | 343 | 205 | 205.8 ± 47.3 | 229.2 ± 41.2 |
| 7HDHA | 343 | 141 | 9.1 ± 3.3 | 8.6 ± 3.7 |
| 4HDHA | 343 | 101 | 20.4 ± 5.47 | 19.9 ± 5.1 |
| DHA | 327 | 283 | 23117.7 ± 7852.2 | 28104.0 ± 10103.4 |
| 18HEPE | 317 | 259 | 33.8 ± 11.3 | 36.2 ± 12.2 |
| 15HEPE | 317 | 219 | 35.3 ± 13.6 | 31.3 ± 8.7 |
| 12HEPE | 317 | 179 | 382.6 ± 116.1 | 402.4 ± 106.0 |
| 5HEPE | 317 | 115 | 45.5 ± 11.7 | 42.7 ± 11.3 |
| EPA | 301 | 257 | 5371.5 ± 514.6 | 5867.2 ± 713.2 |
| 15HETE | 319 | 219 | 287.6 ± 88.1 | 336.4 ± 95.2 |
| 12HETE | 319 | 179 | 4751.4 ± 1271.4 | 5148.0 ± 1153.2 |
| 5HETE | 319 | 115 | 61.2 ± 5.5 | 69.9 ± 13.5 |
| AA | 303 | 259 | 20584.4 ± 4222.3 | 24205.0 ± 4783.4* |
| 17-HDPA | 345 | 247 | 64.4 ± 14.9 | 58.9 ± 13.2 |
| 14-HDPA | 345 | 207 | 112.6 ± 25.5 | 137.2 ± 25.8* |
| 13-HDPA | 345 | 193 | 1.4 ± 0.4 | 1.9 ± 0.6 |

TABLE 15-continued

Peripheral blood SPM substrate and precursor concentrations.

| n-3 DPA bioactive metabolome | Q1 | Q3 | Lipid mediators precursors concentration (pg/mL) Vehicle | ACh 0.1 μM |
|---|---|---|---|---|
| 7-HDPA | 345 | 143 | 56.4 ± 19.3 | 44.9 ± 10.7 |
| DPA | 327 | 283 | 3703.3 ± 703.0 | 3873.1 ± 706.3 |

Peripheral blood from healthy volunteers was collected and incubated with acetylcholine (ACh) at 0.1 μM for 45 min. Plasma was isolated, placed in ice cold methanol containing deuterium labelled internal standards and SPM precursors together with their pathway markers were extracted, identified and quantified using lipid mediator (see methods for details). Q1, M-H (parent ion) and Q3, diagnostic ion in the MS-MS (daughter ion). Results are expressed as pg/mL. Mean ± SEM of n = 9 per condition.
*$p < 0.05$ vs Vehicle group using paired Mann-Whitney test.

We next investigated whether changes in sheer rate, associated with an increase in blood pressure may also regulate $RvD_{n\text{-}3\ DPA}$ production. Blood perfusion at 0.3 pascals (Pa), which is associated with an increase in platelet leukocyte aggregates (n=4 donors), led to a significant increase in plasma $RvD_{n\text{-}3\ DPA}$ when compared with blood perfused at a sheer rate of 0.1 Pa (FIG. 17). Of note, incubation of peripheral blood with norepinephrine (n=6 donors; 0.1-10 μM) (see Shea S A, Hilton M F, Hu K, Scheer F A. Existence of an endogenous circadian blood pressure rhythm in humans that peaks in the evening. Circ Res. 2011; 108(8):980-984) or cortisol (see Nomura S, Fujitaka M, Sakura N, Ueda K. Circadian rhythms in plasma cortisone and cortisol and the cortisone/cortisol ratio. Clin Chim Acta. 1997; 266(2):83-91) (1-10 μM), which are both diurnally regulated in the circulation, did not significantly augment the production of n-3 DPA derived mediators in peripheral blood from healthy volunteers. See Table 16 below.

TABLE 16

SPM concentrations in peripheral blood incubations with cortisol.

| n-3 DPA bioactive metabolome | Q1 | Q3 | Lipid mediators concentration (pg/mL) Vehicle | Cortisol 1 μM | Cortisol 10 μM |
|---|---|---|---|---|---|
| $RvD1_{n\text{-}3\ DPA}$ | 377 | 143 | 1.4 ± 1.1 | 1.9 ± 1.2 | 1.7 ± 1.5 |
| $RvD2_{n\text{-}3\ DPA}$ | 377 | 261 | 1.8 ± 1.3 | 1.0 ± 0.9 | 1.2 ± 0.8 |
| $RvD5_{n\text{-}3\ DPA}$ | 361 | 201 | 1.9 ± 0.3 | 1.1 ± 0.6 | 1.7 ± 0.3 |
| $PD1_{n\text{-}3\ DPA}$ | 361 | 155 | 0.9 ± 0.2 | 1.5 ± 1.1 | 2.5 ± 1.5 |
| $MaR1_{n\text{-}3\ DPA}$ | 361 | 223 | 0.9 ± 0.5 | 0.3 ± 0.2 | 0.2 ± 0.2 |
| RvT1 | 377 | 211 | 0.7 ± 0.3 | 0.5 ± 0.2 | 0.6 ± 0.2 |
| RvT2 | 377 | 197 | 0.1 ± 0.1 | 0.1 ± 0.1 | 0.1 ± 0.0 |
| RvT3 | 377 | 255 | 3.9 ± 2.5 | 1.6 ± 0.5 | 2.2 ± 1.5 |
| RvT4 | 359 | 211 | 2.1 ± 1.3 | 2.7 ± 1.5 | 3.0 ± 1.8 |
| 17-HDPA | 345 | 247 | 73.3 ± 20.8 | 74.9 ± 18.2 | 71.5 ± 17.5 |
| 14-HDPA | 345 | 207 | 282.0 ± 39.0 | 286.2 ± 91.0 | 241.0 ± 40.9 |
| 13-HDPA | 345 | 193 | 3.3 ± 0.7 | 3.2 ± 0.7 | 3.0 ± 0.6 |
| 7-HDPA | 345 | 143 | 239.7 ± 95.6 | 268.9 ± 83.5 | 257.8 ± 109.6 |
| DPA | 327 | 283 | 21213.7 ± 7408.2 | 24568.2 ± 6300.4 | 28823.5 ± 8019.0 |

Peripheral blood from healthy volunteers was collected and incubated with cortisol (1-10 μM) or vehicle for 45 min. Plasma was obtained, placed in ice cold methanol containing deuterium labelled internal standards and lipid mediators were extracted, identified and quantified using lipid mediator profiling (see methods for details). Q1, M-H (parent ion) and Q3, diagnostic ion in the MS-MS (daughter ion). Results are expressed as pg/mL. Mean ± SEM of n = 5 per condition.

Example 10: $RvD_{n\text{-}3\ DPA}$ Reduce Leukocyte and Platelet Activation in Peripheral Blood We next investigated the actions of $RvD_{n\text{-}3\ DPA}$ in regulating monocyte, neutrophil and platelet activation as well as platelet-leukocyte aggregates in light of the pathogenic roles played by cellular activation in cardiovascular disease (Furman M I, Barnard M R, Krueger L A, et al. Circulating monocyte-platelet aggregates are an early marker of acute myocardial infarction. J Am Coll Cardiol. 2001; 38(4):1002-1006; Pfluecke C, Tarnowski D, Plichta L, et al. Monocyte-platelet aggregates and CD11b expression as markers for thrombogenicity in atrial fibrillation. Clin Res Cardiol. 2016; 105(4):314-322; Huo Y, Schober A, Forlow S B, et al. Circulating activated platelets exacerbate atherosclerosis in mice deficient in apolipoprotein E. Nat Med. 2003; 9(1):61-67). Incubation of human peripheral blood with $RvD2_{n\text{-}3\ DPA}$ led to dose dependent decreases in neutrophil CD11b expression and in neutrophil-platelet aggregates measured as decreases in neutrophil CD62P (FIG. 21) and CD41 expression (n=5 donors; ~20% decrease at 10 nM) when compared with cells incubated with platelet activating factor (PAF) alone. In these incubations we also found a significant reduction in monocyte activation where $RvD2_{n\text{-}3\ DPA}$, gave dose dependent decreases in monocyte expression of CD11b, and the platelet markers CD62P (FIG. 21A, E, F) and CD41 (n=5 donors; ~29% decreased at 10 nM). Similar findings were also made when healthy volunteer whole blood was incubated with $RvD5_{n\text{-}3\ DPA}$ that resulted in dose-dependent decreases in neutrophil and monocyte CD11b expression as well as in leukocyte-platelet aggregates (FIG. 21). Of note, in these incubations $RvD1_{n\text{-}3\ DPA}$ only partially regulate neutrophil, monocyte and platelet responses (n=5 donors) suggesting that each of the $RvD_{n\text{-}3\ DPA}$ displays specific biological actions in regulating vascular leukocyte and platelet responses. We next investigated whether $RvD_{n\text{-}3\ DPA}$ displayed direct anti-platelet actions. Incubation of $RvD5_{n\text{-}3\ DPA}$ with platelet rich plasma (PRP) led to a dose dependent reduction in PAF mediated upregulation of CD62P, CD63 and CD41 expression (FIG. 21G).

Example 11: Reduced $RvD_{n\text{-}3\ DPA}$ Correlate with Peripheral Blood Cell Activation in Patients with Cardiovascular Disease We next investigated whether results obtained with healthy volunteers were translatable to the clinical setting. Given that $RvD_{n\text{-}3\ DPA}$ increased during the early morning hours, a time window associated with higher incidence of myocardial infarct (Nakashima H, Mashimo Y, Kurobe M, Muto S, Furudono S, Maemura K. Impact of Morning Onset on the Incidence of Recurrent Acute Coronary Syndrome and Progression of Coronary Atherosclerosis in Acute Myocardial Infarction. Circ J. 2017; 81(3):361-367; Muller J E, Stone P H, Turi Z G, et al. Circadian variation in the frequency of onset of acute myocardial infarction. N Engl J Med. 1985; 313(21):1315-1322), we next investigated the peripheral blood levels of $RvD_{n\text{-}3\ DPA}$ in patients with cardiovascular diseases (CVD) that were also at an increased risk of myocardial infarct. Details and methods for risk criteria are set out in Table 17 below:

TABLE 17

| CVD-demographics and clinical data | |
|---|---|
| Participants | 9 |
| Age (years) | 65.2 ± 8.6 |
| Sex | 7 Male, 2 Female |
| CRP mg/L | 35.4 ± 42.2 |
| IL-6 pg/ml | 2.5 ± 1.0 |
| TNF-α pg/ml | 108.2 ± 74.9 |
| Creatine μmol/L | 119.1 ± 90.5 |
| LDL mmol/L | 3.0 ± 0.2 |
| HDL mmol/L | 0.5 ± 0.1 |
| Type II Diabetes | 3 |
| Hypertension | 9 |
| Current Smoking | 0 |
| Obese n | 4 |
| Previous AMI | 1 |
| Previous PCI | 4 |
| LVEF ≤ 50% | 4 |
| Aspirin (n) | 9 |
| Statins (n) | Atorvastatin (4), Simvastatin (3) and Rosuvastatin (1) |
| Other medications (n) | Allopurinol (1), Amitriptyline (2), Amlodipine (2), Apixaban (1), Bisoprolol (6), Candesartan (1), Citalopram (1), Clopidogrel (2), Codeine (1), Cyanacobalamin (1), Dorzolamide (1), Doxazosin (2), Enoxaparin (1), Fentanyl (1), Finasteride (1), Flucloxacillin (1), Fluoxetine (2), Furosemide (2), Isosorbide mononitrate (1), Lansoprazole (4), Lantus Insulin (1), Lisinopril (1), Metformin (1), Nicorandil (1), NoroRapid Insulin (1), Omeprazole (3), Paracetamol (1), Phyllocontine (1), Priadel (1), Ramipril (5), Salbutamol (1), Salmeterol (1), Sertraline (1), Setagliptin (1), Tamoxifen (1), Tamsulosin (2) Temazepam (1), Thiamine (1), Tildiem (1), Timolol (1), Tioropium bromide (1), Warfarin (1), Xalatan (1). |

Using lipid mediator profiling we found significant decreases in morning (9:00 h), midday (12:00 h) and evening (16:00-18:00 h) plasma RvD$_{n-3\ DPA}$ concentrations in CVD patients when compared to the respective values in healthy volunteers (FIG. 22A and Table 18).

TABLE 18

Peripheral blood LM profiles in patients with CVD.

| | | | Plasma from CVD patients Lipid mediators concentration (pg/mL) | | |
|---|---|---|---|---|---|
| | Q1 | Q3 | PM | AM | Midday |
| DHA bioactive metabolome | | | | | |
| RvD1 | 375 | 141 | 1.0 ± 0.5 | 0.6 ± 0.5 | 0.5 ± 0.2 |
| RvD2 | 375 | 141 | 0.3 ± 0.1 | 0.2 ± 0.2 | 0.2 ± 0.1* |
| RvD3 | 375 | 147 | 0.2 ± 0.1 | 0.4 ± 0.2 | 0.1 ± 0.1 |
| RvD4 | 375 | 101 | 1.8 ± 0.5 | 2.5 ± 1.2 | 2.3 ± 1.6 |
| RvD5 | 359 | 199 | 1.8 ± 0.4 | 2.1 ± 0.9 | 0.7 ± 1.3 |
| RvD6 | 359 | 101 | 0.3 ± 0.2 | 0.3 ± 0.1 | 0.2 ± 0.2 |
| 17R-RvD1 | 375 | 141 | 0.5 ± 0.3 | 0.5 ± 0.2 | 1.2 ± 0.9 |
| 17R-RvD3 | 375 | 147 | 0.3 ± 0.3 | 0.3 ± 0.2 | 1.2 ± 0.8 |
| PD1 | 359 | 153 | 0.3 ± 0.1 | 0.8 ± 0.2* | 0.5 ± 0.5 |
| 17R-PD1 | 359 | 153 | 0.4 ± 0.3 | | 0.2 ± 0.1 |
| 10S,17S-diHDHA | 359 | 153 | 0.3 ± 0.2 | 0.1 ± 0.1 | |
| 22-OH-PD1 | 375 | 153 | 2.4 ± 2.3 | 0.1 ± 0.1 | 0.4 ± 0.3 |
| MaR1 | 359 | 221 | 0.8 ± 0.4 | 0.9 ± 0.5 | 1.0 ± 0.7 |
| 7S,14S-diHDHA | 359 | 221 | 0.2 ± 0.2 | 0.8 ± 0.5 | — |
| 4S,14S-diHDHA | 359 | 101 | 0.6 ± 0.3 | 0.4 ± 0.2 | 0.1 ± 0.1* |
| n-3 DPA bioactive metabolome | | | | | |
| RvD1$_{n-3\ DPA}$ | 377 | 143 | 1.1 ± 0.2 | 1.4 ± 0.4 | 0.5 ± 0.3* |
| RvD2$_{n-3\ DPA}$ | 377 | 261 | 1.0 ± 0.4 | 1.7 ± 0.6 | 0.5 ± 0.2 |
| RvD5$_{n-3\ DPA}$ | 361 | 263 | 0.9 ± 0.3 | 0.9 ± 0.4 | 1.0 ± 0.6 |
| PD1$_{n-3\ DPA}$ | 361 | 183 | 0.3 ± 0.1 | 0.2 ± 0.1 | 0.7 ± 0.2 |
| MaR1$_{n-3\ DPA}$ | 361 | 249 | 0.3 ± 0.2 | — | 0.6 ± 0.7 |
| RvT1 | 377 | 193 | 0.1 ± 0.1 | 0.3 ± 0.2 | — |
| RvT2 | 377 | 143 | — | 0.3 ± 0.2 | — |
| RvT3 | 377 | 255 | 0.2 ± 0.1 | 0.9 ± 0.3 | 0.2 ± 0.2 |
| RvT4 | 359 | 193 | 0.4 ± 0.2 | 0.3 ± 0.1 | — |
| EPA bioactive metabolome | | | | | |
| RvE1 | 349 | 195 | 2.5 ± 2.2 | 1.8 ± 1.2 | 0.4 ± 0.2 |
| RvE2 | 333 | 199 | 0.5 ± 0.4 | 0.2 ± 0.1 | 0.1 ± 0.0 |
| RvE3 | 333 | 201 | 1.5 ± 0.9 | 2.1 ± 0.8 | 1.7 ± 1.9 |
| AA bioactive metabolome | | | | | |
| $LXA_4$ | 351 | 217 | — | 0.1 ± 0.1 | 0.4 ± 0.3 |
| $LXB_4$ | 351 | 221 | 1.1 ± 0.4 | 1.1 ± 0.6 | 0.5 ± 0.4* |
| 5S,15S-diHETE | 335 | 235 | 18.4 ± 5.6 | 15.8 ± 7.9 | 8.1 ± 3.0 |
| 15epi-$LXA_4$ | 351 | 217 | 4.6 ± 2.6 | 1.6 ± 0.6 | 2.3 ± 1.6 |
| 15epi-$LXB_4$ | 351 | 221 | 13.5 ± 5.3 | 20.5 ± 7.6 | 5.5 ± 2.6 |
| $LTB_4$ | 335 | 195 | 2.2 ± 0.4 | 2.1 ± 0.6 | 1.1 ± 0.6 |
| 5S,12S-diHETE | 335 | 195 | 0.3 ± 0.1 | 0.8 ± 0.5 | 0.2 ± 0.2 |
| 20-OH-$LTB_4$ | 351 | 195 | 0.4 ± 0.2 | 0.2 ± 0.1 | 0.1 ± 0.1 |
| $PGD_2$ | 351 | 189 | 5.7 ± 2.5 | 2.6 ± 0.6 | 5.5 ± 2.4 |
| $PGE_2$ | 351 | 189 | 13.3 ± 3.6 | 9.6 ± 2.4* | 20.3 ± 9.2 |
| $PGF_{2\alpha}$ | 353 | 193 | 9.1 ± 4.0 | 7.4 ± 1.9 | 14.1 ± 13.7 |
| $TxB_2$ | 369 | 169 | 36.2 ± 23.9 | 26.6 ± 20.0 | 86.1 ± 93.5 |

Peripheral blood from CVD patients was collected at 9:00 h (AM) 12:00 h (Midday) and between 16:00-18:00 h (PM). Plasma was placed in ice-cold methanol containing internal standards. Lipid mediators (LM) were extracted, identified and quantified using LM-profiling (see methods for details). Q1, M-H (parent ion) and Q3, diagnostic ion in the MS-MS (daughter ion). Results are mean ± s.e.m. and expressed as pg/mL. n = 9 paired patients. The detection limit was ~0.1 pg.

—, Below limits of detection

*$p < 0.05$ vs PM values using paired Mann-Whitney test.

Furthermore, there was a marked impairment in the diurnal regulation of these mediators in CVD patients, where morning RvD$_{n-3\ DPA}$ concentrations were only slightly but not significantly elevated compared with evening values (FIG. 22A). In these patients we also found significant reductions in plasma concentrations of the RvD$_{n-3\ DPA}$ biosynthetic marker 7-HDPA (FIG. 18; Dalli J, Colas R A, Serhan C N. Novel n-3 immunoresolvents: structures and actions. *Sci Rep.* 2013; 3:1940).

Flow cytometric analysis of peripheral blood leukocyte from these patients demonstrated increases in the expression of CD11b on both neutrophils and monocytes from CVD patients when compared with healthy volunteers (FIG. 22B-E). This was coupled with increases in platelet-neutrophil and platelet-monocyte aggregates in peripheral blood from CVD patients when compared with peripheral blood from healthy volunteers (FIG. 22B-E). In addition, we found a significant correlation between peripheral blood RvD$_{n-3\ DPA}$ concentration and leukocyte and platelet activation as demonstrated by a negative correlation between RvD$_{n-3\ DPA}$ and neutrophil CD41 expression, monocyte CD41, and platelet CD63 and CD42b expression (FIG. 22F-J).

In order to establish the mechanisms leading to the downregulation of RvD$_{n-3\ DPA}$ biosynthesis we next assessed the expression of the RvD$_{n-3\ DPA}$ biosynthetic enzymes in peripheral blood leukocytes. Flow cytometric assessment of peripheral blood myeloid cells from both healthy volunteers demonstrated that myeloid cell expression of both 15-LOX and 5-LOX was upregulated early in the morning (FIG. 23A-C), an increase that was primarily contributed by an increase in the expression of these enzymes in neutrophils in healthy volunteers (FIG. 23C). Of note, the diurnal regulation in both of these biosynthetic enzymes was lost in peripheral blood leukocytes from CVD patients (FIG. 23). These findings suggest that an impaired expression of these enzymes may contribute to altered RvD$_{n-3\ DPA}$ biosynthesis.

Example 12: Elevated Plasma Adenosine Reduces RvD$_{n-3\ DPA}$ Biosynthesis in CVD Patients Given that we found a significant reduction in 7-HDPA concentrations in peripheral blood from CVD patients (FIG. 18A) we investigated whether adenosine, which is known to regulate 5-LOX activity (Krump E, Picard S, Mancini J, Borgeat P. Suppression of leukotriene B4 biosynthesis by endogenous adenosine in ligand-activated human neutrophils. J Exp Med. 1997; 186(8):1401-1406) was elevated in plasma from these patients. LC/MS-MS analysis demonstrated an increase in the peripheral blood adenosine levels at all intervals tested when compared with healthy volunteers (FIG. 24A). We next assessed whether this increase in peripheral blood adenosine concentrations was responsible for the observed reduction in circulating RvD$_{n-3\ DPA}$ concentrations in patients. Here we incubated peripheral blood from CVD patients with adenosine deaminase (ADA), the enzyme that degrades adenosine (Norris P C, Libreros S, Chiang N, Serhan C N. A cluster of immunoresolvents links coagulation to innate host defense in human blood. Sci Signal. 2017; 10(490)), and assessed RvD$_{n-3\ DPA}$ levels. ADA incubation led to an increase in the concentrations of RvD$_{n-3\ DPA}$ (FIG. 24B). Of note, we also found significant increases in peripheral blood ACh levels, and an impairment in the diurnal regulation of this neurotransmitter in CVD patients that was not associated with an alteration in 15-LOX activity as measured by plasma 17-HDPA concentrations (FIG. 18B). These results suggest that upregulation of this neurotransmitter counteracted the downregulation of 15-LOX expression observed in peripheral blood leukocytes (FIG. 23).

Example 13: Reduced Leukocyte Activation by RvD2$_{n-3\ DPA}$ and RvD5$_{n-3\ DPA}$ in Patient Peripheral Blood In order to test whether there was a relationship between the increased systemic inflammation and reduced n-3 DPA derived SPM we next investigated whether $RvD_{n\text{-}3\ DPA}$ regulated patient peripheral blood leukocyte responses. $RvD2_{n\text{-}3\ DPA}$ dose-dependently decreased platelet-neutrophil and platelet-monocyte aggregates without significantly regulating CD11b expression (FIG. 24C,D). Incubation of whole blood with $RvD5_{n\text{-}3\ DPA}$ also led to a reduction in neutrophil platelet and monocyte-platelet aggregates with higher potency than $RvD2_{n\text{-}3\ DPA}$ (FIG. 24C,D). $RvD5_{n\text{-}3\ DPA}$ significantly reduced neutrophil and monocyte CD11b expression (FIG. 24C,D). In addition to displaying actions on leukocytes, $RvD2_{n\text{-}3\ DPA}$ and $RvD5_{n\text{-}3\ DPA}$ also down-regulated platelet CD63 and CD62P expression in peripheral blood from CVD patients. (FIG. 24E).

We next tested whether the actions of these two mediators were also retained in the presence of PAF (Shinohara M, Kibi M, Riley I R, et al. Cell-cell interactions and broncho-constrictor eicosanoid reduction with inhaled carbon monoxide and resolvin D1. Am J Physiol Lung Cell Mol Physiol. 2014; 307(10):L746-757; Palur Ramakrishnan A V, Varghese T P, Vanapalli S, Nair N K, Mingate M D. Platelet activating factor: A potential biomarker in acute coronary syndrome? Cardiovasc Ther. 2017; 35(1):64-70). Incubation of patient whole blood with either $RvD2_{n\text{-}3\ DPA}$ or $RvD5_{n\text{-}3\ DPA}$ led to decreases in platelet-neutrophil and platelet-monocyte aggregates measured as decreases in CD62P (FIG. 19A,B) and CD41 expression (n=9 patients) on both leukocyte subsets. We also found that $RvD5_{n\text{-}3\ DPA}$ decreased the expression of CD11b on neutrophils and monocytes, an action that was only in part shared with $RvD2_{n\text{-}3\ DPA}$ (FIG. 19C,D). Both of these SPM also dose-dependently regulated the expression for CD62P and CD63 on peripheral blood platelets (FIG. 19E, F). These results suggest that reductions in circulating $RvD_{n\text{-}3\ DPA}$ lead to increased peripheral blood leukocyte and platelet activation in CVD patients.

Example 14: $RvD5_{n\text{-}3\ DPA}$ Reduces Systemic Leukocyte and Platelet Activation and Protects Against Vascular Disease in ApoE−/− Mice We next investigated whether the protective actions of $RvD5_{n\text{-}3\ DPA}$ observed with peripheral blood cells from both healthy volunteers and CVD patients were also retained in vivo. For this purpose $ApoE^{-/-}$ mice were fed western diet for 6 weeks and $RvD5_{n\text{-}3\ DPA}$ (100 ng/mouse; i.v.) was administered on alternative days for a two-week period. $RvD5_{n\text{-}3\ DPA}$ administration reduced circulating platelet monocyte-aggregates, as measured by a decrease in both CD41 and CD62P expression on CD115 positive cells, and monocyte activation with a decrease in CD11b expression (FIG. 25A). We also found a significant reduction in platelet-neutrophil aggregates and neutrophil activation with a >60% reduction in CD11b expression in mice given $RvD5_{n\text{-}3\ DPA}$ when compared with mice given vehicle alone (FIG. 25B).

Since platelet-leukocyte aggregates are involved in the pathogenesis of atherosclerosis (Huo Y, Schober A, Forlow S B, et al. Circulating activated platelets exacerbate atherosclerosis in mice deficient in apolipoprotein E. *Nat Med.* 2003; 9(1):61-67) we next investigated whether $RvD5_{n\text{-}3\ DPA}$ also protected against vascular disease. LC/MS-MS analysis of aortic sections from mice given $RvD5_{n\text{-}3\ DPA}$ demonstrated distinct lipid mediator profiles when compared with mice given vehicle. This was characterized by a significant upregulation of DHA and AA derived SPM including MaR1 and 15-epi-LXA4 (FIG. 25C and Table 19).

TABLE 19

$RyD5_{n\text{-}3\ DPA}$ administration upregulated SPM and reduced pro-inflammatory eicosanoids in aortic tissues from $ApoE^{-/-}$.

| DHA Bioactive Metabolome | Q1 | Q3 | $ApoE^{-/-}$ WD (pg/10 mg aorta) | $ApoE^{-/-}$ WD + $RvD5_{n\text{-}3\ DPA}$ (pg/10 mg aorta) |
|---|---|---|---|---|
| RvD1 | 375 | 233 | 3.7 ± 1.1 | 1.7 ± 0.9* |
| RvD2 | 375 | 215 | 0.7 ± 0.7 | 0.4 ± 0.4 |
| RvD3 | 375 | 147 | 5.7 ± 3.9 | 2.4 ± 0.6 |
| RvD4 | 375 | 225 | 0.2 ± 0.1 | — |
| RvD5 | 359 | 199 | 0.3 ± 0.1 | 0.4 ± 0.2 |
| RvD6 | 359 | 159 | 1.0 ± 0.8 | 1.5 ± 1.1 |
| 17R-RvD1 | 375 | 215 | 0.6 ± 0.1 | 1.6 ± 0.9 |
| 17R-RvD3 | 375 | 147 | 1.2 ± 0.7 | 1.3 ± 0.3 |
| PD1 | 359 | 153 | 2.1 ± 0.7 | 2.6 ± 0.7 |
| 10S,17S-diHDHA | 359 | 153 | 32.2 ± 6.0 | 66.0 ± 35.4 |
| 17R-PD1 | 359 | 137 | 0.8 ± 0.4 | 0.3 ± 0.2 |
| 22-OH-PD1 | 375 | 153 | 7.2 ± 1.7 | 6.0 ± 1.0 |
| MaR1 | 359 | 177 | 17.7 ± 2.3 | 35.4 ± 22.7* |
| 7S,14S-diHDHA | 359 | 177 | 0.3 ± 0.3 | 1.8 ± 0.3* |
| 4,14-diHDHA | 359 | 159 | 3.5 ± 2.1 | 4.9 ± 2.0 |
| n-3 DPA Bioactive Metabolome | | | | |
| RvT1 | 377 | 211 | — | — |
| RvT2 | 377 | 255 | — | — |
| RvT3 | 377 | 173 | — | — |
| RvT4 | 361 | 193 | — | — |
| $RvD1_{n\text{-}3\ DPA}$ | 377 | 215 | 0.1 ± 0.1 | 0.1 ± 0.1 |
| $RvD2_{n\text{-}3\ DPA}$ | 377 | 261 | — | 0.1 ± 0.1 |
| $RvD5_{n\text{-}3\ DPA}$ | 361 | 263 | 0.1 ± 0.1 | 0.1 ± 0.1 |
| $PD1_{n\text{-}3\ DPA}$ | 361 | 183 | 0.1 ± 0.1 | 0.0 ± 0.0 |
| $MaR1_{n\text{-}3\ DPA}$ | 361 | 223 | — | — |
| EPA Bioactive Metabolome | | | | |
| RvEl | 349 | 161 | 1.8 ± 0.6 | 1.8 ± 0.5 |
| RvE2 | 333 | 159 | 1.2 ± 1.3 | 0.1 ± 0.1 |
| RvE3 | 333 | 201 | 0.3 ± 0.2 | 0.7 ± 0.1 |

TABLE 19-continued

RyD5$_{n\text{-}3\ DPA}$ administration upregulated SPM and reduced pro-inflammatory eicosanoids in aortic tissues from ApoE$^{-/-}$.

| DHA Bioactive Metabolome | Q1 | Q3 | ApoE$^{-/-}$ WD (pg/10 mg aorta) | ApoE$^{-/-}$ WD + RvD5$_{n\text{-}3\ DPA}$ (pg/10 mg aorta) |
|---|---|---|---|---|
| AA Bioactive Metabolome | | | | |
| $LXA_4$ | 351 | 115 | 0.4 ± 0.2 | 0.3 ± 0.0 |
| $LXB_4$ | 351 | 221 | 1.3 ± 0.8 | 0.6 ± 0.4 |
| 5S,15S-diHETE | 335 | 235 | 35.6 ± 24.0 | 51.9 ± 15.3 |
| 15-epi-$LXA_4$ | 351 | 115 | 6.2 ± 2.2 | 9.6 ± 1.9* |
| 15-epi-$LXB_4$ | 351 | 221 | 4.6 ± 4.3 | 1.4 ± 0.5 |
| $LTB_4$ | 335 | 195 | 1.4 ± 0.3 | 1.7 ± 0.3 |
| 5S,12S-diHETE | 335 | 195 | 1.3 ± 0.4 | 0.6 ± 0.2 |
| 20-OH-$LTB_4$ | 351 | 195 | — | — |
| $PGE_2$ | 351 | 189 | 24.1 ± 2.2 | 20.5 ± 4.5* |
| $PGD_2$ | 351 | 189 | 18.5 ± 2.9 | 14.9 ± 3.5 |
| $PGF_{2\alpha}$ | 353 | 193 | 10.8 ± 0.7 | 10.0 ± 1.7 |
| $TxB_2$ | 369 | 169 | 46.9 ± 6.5 | 34.5 ± 4.1* |

ApoE$^{-/-}$ mice were fed a Western diet (WD) for 6 weeks. On week 4 mice were administered vehicle or 100 ng/mouse RvD5n-3 DPA (via i.v. injection) on alternative days. Descending aortas were harvested and placed in ice-cold methanol containing internal standards. Lipid mediators (LM) were extracted, identified and quantified using LM-profiling (see methods for details). Q1, M-H (parent ion) and Q3, diagnostic ion in the MS-MS (daughter ion). Results are mean ± s.e.m. and expressed as pg/10 mg tissue. n = 4 mice per group. *$p < 0.05$ vs Vehicle mice using Mann-Whitney test.

We also found significant reductions in aortic prostanoids with concentrations of TxB2 being reduced by >35% in mice given RvD5$_{n\text{-}3\ DPA}$ (FIG. 25C and Table 19). Oil red-O staining demonstrated a significant reduction in aortic lesions in mice given RvD5$_{n\text{-}3\ DPA}$ when compared to mice given vehicle (FIG. 25D). Together these findings demonstrate that the protective actions of RvD5$_{n\text{-}3\ DPA}$ on platelets and leukocytes are also retained in vivo leading to reduced vascular disease.

In the present studies we uncovered a novel host protective mechanism centered on the diurnal regulation of systemic RvD$_{n\text{-}3\ DPA}$ in healthy volunteers. Disruption in the production of these mediators correlated with increased peripheral blood leukocyte and platelet activation in patients with CVD. It is now widely appreciated that physiological processes including cardiovascular function and the immune system are under the control of a molecular clock that oscillates following a diurnal pattern (Ingle K A, Kain V, Goel M, Prabhu S D, Young M E, Halade G V. Cardiomyocyte-specific Bmal1 deletion in mice triggers diastolic dysfunction, extracellular matrix response, and impaired resolution of inflammation. Am J Physiol Heart Circ Physiol. 2015; 309(11):H1827-1836; McAlpine C S, Swirski F K. Circadian Influence on Metabolism and Inflammation in Atherosclerosis. Circ Res. 2016; 119(1):131-141). In the vasculature, platelet activation is at a maximum during the early hours of the day with the upregulation of several activation markers including CD62P (Scheer F A, Michelson A D, Frelinger A L, 3rd, et al. The human endogenous circadian system causes greatest platelet activation during the biological morning independent of behaviors. *PLoS One.* 2011; 6(9):e24549). Of note, this increase in platelet activation is coincident with an increase in plasma plasminogen activator inhibitor-1, a serine protease inhibitor that functions as the principal inhibitor of tissue plasminogen activator and urokinase, thereby increasing the risk of thrombosis (Sakata K, Hoshino T, Yoshida H, et al. Circadian fluctuations of tissue plasminogen activator antigen and plasminogen activator inhibitor-1 antigens in vasospastic angina. Am Heart J. 1992; 124(4):854-860).

Platelet CD62P mediates platelet-leukocyte interactions, a process that in addition to facilitating leukocyte recruitment to the vascular endothelium is also involved in leukocyte activation and the production of inflammatory mediators including cysteinyl leukotrienes (Shinohara M, Kibi M, Riley I R, et al. Cell-cell interactions and bronchoconstrictor eicosanoid reduction with inhaled carbon monoxide and resolvin D1. Am J Physiol Lung Cell Mol Physiol. 2014; 307(10):L746-757), tumor necrosis factor-α and C—C motif ligand-2 (Furman M I, Barnard M R, Krueger L A, et al. Circulating monocyte-platelet aggregates are an early marker of acute myocardial infarction. J Am Coll Cardiol. 2001; 38(4):1002-1006; Pfluecke C, Tarnowski D, Plichta L, et al. Monocyte-platelet aggregates and CD11b expression as markers for thrombogenicity in atrial fibrillation. Clin Res Cardiol. 2016; 105(4):314-322). CD62P enhances platelet adhesion to endothelial cells expressing fratelkine, and triggers the release of Weibel-Palade-bodies in endothelial cells, thus perpetuating the pro-inflammatory and pro-thrombotic status during the early hours of the day. In addition, platelet-leukocyte aggregates are implicated in vascular disease pathogenesis, including atherosclerosis (Huo Y, Schober A, Forlow S B, et al. Circulating activated platelets exacerbate atherosclerosis in mice deficient in apolipoprotein E. Nat Med. 2003; 9(1):61-67). Thus, these observations suggest that in healthy individuals endogenous, diurnally regulated, protective mechanisms are engaged that counterregulate this physiological inflammation to prevent vascular inflammation and thrombus formation. In the present study, we found that plasma RvD$_{n\text{-}3\ DPA}$ concentrations increase during the early morning hours (FIG. 20 and Table 13). Results from in vitro experiments (Table 15) suggest that the selective upregulation of these SPM results from a preferential utilization of n-3 DPA by the leukocyte biosynthetic enzymes in peripheral blood when compared to other fatty acids that are substrate for SPM biosynthesis. The precise mechanisms leading to this preferential utilization remain subject to future investigations.

In patients with CVD we found a significant decrease (~3 fold lower) in peripheral blood RvD$_{n\text{-}3\ DPA}$ during the early morning hours that was also observed at other intervals during the day. This reduction in RvD$_{n\text{-}3\ DPA}$ concentrations was associated with an increased leukocyte and platelet activation suggesting that RvD$_{n\text{-}3\ DPA}$ are endogenous protective signals that control physiological platelet and leukocyte activation. This is further supported by the observation that $RvD_{n\text{-}3\ DPA}$ reduced leukocyte and platelet activation in peripheral blood from both healthy volunteers and patients. $RvD5_{n\text{-}3\ DPA}$ reduced platelet-leukocytes aggregates in vivo and modulated vascular lipid mediator profiles reducing concentrations of the pro-thrombogenic mediator $TxA_2$ (measured as its metabolite$TxB_2$) and upregulating the formation of pro-resolving mediators including MaR1 and 15-epi-$LXA_4$. Furthermore $RvD5_{n\text{-}3\ DPA}$ also decreased early aortic lesions in $ApoE^{-/-}$ mice (FIG. 25). The present findings are in line with published findings demonstrating an altered production of vascular DHA-derived SPM including RvD1, RvD2 and MaR1 and impaired resolution responses in the pathogenesis of atherosclerosis. Together these findings demonstrate that alterations in the diurnal regulation of vascular $RvD_{n\text{-}3\ DPA}$ may occur early on in the pathogenesis of cardiovascular diseases that results in vascular inflammation and impaired biosynthesis of DHA derived SPM. This is supported by the recent observation that deletion of BMAL1, that plays a key role in the mammalian autoregulatory transcription translation negative feedback loop responsible for generating molecular circadian rhythms, leads to increased severity of atherosclerosis in $ApoE^{-/-}$ mice (Huo M, Huang Y, Qu D, et al. Myeloid Bmal1 deletion increases monocyte recruitment and worsens atherosclerosis. FASEB J. 2017; 31(3):1097-1106).

Tissue pro-resolving mediator biosynthesis is also regulated by the vagus nerve via release of the neurotransmitter ACh, a mechanism that is central in maintaining tissue resolution tone (Dalli J, Colas R A, Arnardottir H, Serhan C N. Vagal Regulation of Group 3 Innate Lymphoid Cells and the Immunoresolvent PCTR1 Controls Infection Resolution. Immunity 2017; 46(1):92-105). Results from the present study demonstrate that the vascular levels of this neurotransmitter in healthy volunteers are diurnally regulated and increase during the early morning hours (FIG. 16). Incubation of peripheral blood from healthy volunteers with ACh increased $RvD_{n\text{-}3\ DPA}$ via upregulating 15-LOX activity, indicating that this neurotransmitter was also involved in controlling the production of these molecules in peripheral blood. We also found that increases in sheer rate lead to increased platelet leukocyte aggregates as well as $RvD_{n\text{-}3\ DPA}$ (FIG. 17). This is in line with previous findings that demonstrate a role for platelet-leukocyte heterotypic aggregates in SPM biosynthesis (Abdulnour R E, Sham H P, Douda D N, et al. Aspirin-triggered resolvin D1 is produced during self-resolving gram-negative bacterial pneumonia and regulates host immune responses for the resolution of lung inflammation. Mucosal Immunol 2016; 9(5):1278-1287; Brancaleone V, Gobbetti T, Cenac N, et al. A vasculo-protective circuit centered on lipoxin A4 and aspirin-triggered 15-epi-lipoxin A4 operative in murine microcirculation. Blood. 2013; 122(4):608-617). Of note in CVD patients we found a significant reduction in both the expression and activity of 5-LOX as demonstrated by a reduction in 7-HDPA (FIG. 18 and FIG. 23). This was linked with a significant increase in adenosine, a known regulator of 5-LOX activity. Incubation of peripheral blood from CVD patients with ADA upregulated plasma $RvD_{n\text{-}3\ DPA}$ (FIG. 24) suggesting this increase in circulating adenosine is responsible for altered peripheral blood levels of these SPM in CVD patients. These findings are also in line with findings made with peripheral blood from healthy volunteers demonstrating that reducing adenosine concentration during coagulation upregulates SPM biosynthesis.

In summation, the present findings uncover a novel protective pathway centered on the diurnal regulation of vascular n-3 DPA-derived resolvins. Increases in these molecules during the morning hours counterregulate physiological platelet and leukocyte activation limiting systemic inflammation and potentially vascular disease thereby ensuring vascular homeostasis. In patients with cardiovascular disease, there is a significant loss in both production and circadian regulation of these molecules that is associated with an increase in peripheral blood cell activation leading to increased systemic inflammation and susceptibility to myocardial infarct. In line with this notion, $RvD_{n\text{-}3\ DPA}$ reprogrammed circulating leukocyte and platelet activation, which in mice resulted in a significant reduction in vascular disease. Thereby, strategies to restore peripheral blood $RvD_{n\text{-}3\ DPA}$, including n-3 DPA supplementation that was recently shown to increase plasma $RvD5_{n\text{-}3\ DPA}$ in healthy volunteers, may be a useful therapeutic option. In addition, therapeutics based on the $RvD_{n\text{-}3\ DPA}$ may also provide new opportunities for fine-tuning the increased inflammatory status present in these patients, dampening systemic inflammation and reducing vascular disease.

The invention claimed is:

1. A method of treating or reducing the risk of developing cardiovascular disease, vascular inflammation, or myocardial infarction, or treating dysfunctional diurnal regulation of one or more n-3 DPA-derived resolvins, or attenuating activation of platelets, or reducing formation of platelet-leukocytes aggregates in a human subject in need thereof, which comprises administering a therapeutically effective amount of at least one n-3 DPA-derived resolvin to a subject in need thereof such that $t_{max}$ occurs between 7 am and 9 am and/or increasing the biosynthesis, activity or expression levels of at least one n-3 DPA-derived resolvin in a subject in need thereof such that $t_{max}$ occurs between 7 am and 9 am, wherein the at least one n-3 DPA-derived resolvin is formulated for immediate or delayed and/or controlled release wherein the at least one n-3 DPA-derived resolvin is $RVD1_{n\text{-}3\ DPA}$, $RVD2_{n\text{-}3\ DPA}$ and/or $RvD5_{n\text{-}3\ DPA}$.

2. A method as claimed in claim 1, wherein the at least one n-3 DPA-derived resolvin is administered in a dosage that is calculated to achieve a peak plasma concentration of n-3 DPA-derived resolvin of at least 10 pg/mL.

3. A method as claimed in claim 1, which comprises the simultaneous, sequential or separate administration of a combination of two or more n-3 DPA-derived resolvins to the subject.

4. A method as claimed in claim 1, wherein the at least one n-3 DPA-derived resolvin is administered orally.

5. A method as claimed in claim 1, which comprises reducing the activity or expression levels of adenosine and/or increasing the activity or expression levels of 5-LOX and/or 15-LOX in the subject.

6. The method as claimed in claim 2, wherein the at least one n-3 DPA-derived resolvin is administered in a dosage that is calculated to achieve a peak plasma concentration of n-3 DPA-derived resolvin of 15-25 pg/mL.

* * * * *